(12) United States Patent
Liu et al.

(10) Patent No.: US 12,103,974 B2
(45) Date of Patent: Oct. 1, 2024

(54) ANTI-OX40 ANTIBODIES AND METHODS OF USE

(71) Applicant: BEIGENE, LTD., Grand Cayman (KY)

(72) Inventors: Ye Liu, Beijing (CN); Tong Zhang, Beijing (CN); Zuobai Wang, Beijing (CN); Kang Li, Beijing (CN)

(73) Assignee: BEIGENE, LTD., Grand Cayman (KY)

( * ) Notice: Subject to any disclaimer, the term of this patent is extended or adjusted under 35 U.S.C. 154(b) by 863 days.

(21) Appl. No.: 17/055,267

(22) PCT Filed: May 22, 2019

(86) PCT No.: PCT/CN2019/088013
§ 371 (c)(1),
(2) Date: Nov. 13, 2020

(87) PCT Pub. No.: WO2019/223733
PCT Pub. Date: Nov. 28, 2019

(65) Prior Publication Data
US 2021/0214452 A1   Jul. 15, 2021

(30) Foreign Application Priority Data

May 23, 2018 (WO) ................ PCT/CN2018/088101

(51) Int. Cl.
| | | |
|---|---|---|
| A61K 39/00 | (2006.01) | |
| A61K 31/337 | (2006.01) | |
| A61K 31/454 | (2006.01) | |
| A61K 31/706 | (2006.01) | |
| A61K 39/395 | (2006.01) | |
| C07K 16/28 | (2006.01) | |

(52) U.S. Cl.
CPC ........ *C07K 16/2878* (2013.01); *A61K 31/337* (2013.01); *A61K 31/454* (2013.01); *A61K 31/706* (2013.01); *A61K 39/3955* (2013.01); *A61K 2039/505* (2013.01); *C07K 2317/24* (2013.01); *C07K 2317/33* (2013.01); *C07K 2317/34* (2013.01); *C07K 2317/41* (2013.01); *C07K 2317/56* (2013.01); *C07K 2317/565* (2013.01); *C07K 2317/732* (2013.01); *C07K 2317/75* (2013.01); *C07K 2317/92* (2013.01)

(58) Field of Classification Search
CPC ................................................ A61K 2039/505
See application file for complete search history.

(56) References Cited

U.S. PATENT DOCUMENTS

| | | | |
|---|---|---|---|
| 5,624,821 A | 4/1997 | Winter et al. | |
| 5,648,260 A | 7/1997 | Winter et al. | |
| 6,194,551 B1 | 2/2001 | Idusogie et al. | |
| 8,735,553 B1 | 5/2014 | Li et al. | |
| 9,006,399 B2 * | 4/2015 | Liu ........................ | A61P 35/00 |
| | | | 424/154.1 |
| 10,544,225 B2 | 1/2020 | Li et al. | |
| 2010/0172900 A1 | 7/2010 | Korman et al. | |
| 2017/0015755 A1 | 1/2017 | Walsh et al. | |
| 2018/0215825 A1 | 8/2018 | Li et al. | |
| 2019/0100591 A1 | 4/2019 | Cooper et al. | |
| 2020/0157214 A1 | 5/2020 | Willuda et al. | |
| 2023/0002499 A1 | 1/2023 | Jiang et al. | |
| 2023/0002500 A1 | 1/2023 | Jiang | |
| 2023/0002501 A1 | 1/2023 | Jiang | |
| 2023/0011916 A1 | 1/2023 | Jiang et al. | |
| 2023/0022859 A1 | 1/2023 | Jiang et al. | |

FOREIGN PATENT DOCUMENTS

| | | |
|---|---|---|
| CN | 101578296 A | 11/2009 |
| CN | 102010407 A | 4/2011 |
| CN | 102057272 B | 2/2015 |
| CN | 105777776 A | 7/2016 |
| CN | 106103486 A | 11/2016 |
| CN | 106132991 A | 11/2016 |
| CN | 106604742 A | 4/2017 |
| CN | 107722123 A | 2/2018 |
| CN | 107743495 A | 2/2018 |
| CN | 107810011 A | 3/2018 |
| CN | 109790218 A | 5/2019 |
| CN | 110092832 A | 8/2019 |
| CN | 110467674 A | 11/2019 |
| JP | 2016-515544 A | 5/2016 |
| WO | WO-9429351 A2 | 12/1994 |
| WO | WO-0042072 A2 | 7/2000 |
| WO | WO-2013038191 A2 | 3/2013 |
| WO | WO-2013173223 A1 | 11/2013 |
| WO | WO-2014148895 A1 | 9/2014 |

(Continued)

OTHER PUBLICATIONS

Rudikoff et al. (Proc. Natl. Acad. Sci. USA. 1982; 79: 1979-1983).*
Mariuzza et al. (Annu. Rev. Biophys. Biophys. Chem. 1987; 16: 139-159).*
Gussow et al. (Methods in Enzymology. 1991; 203: 99-121).*
Giusti et al. (Proc. Natl. Acad. Sci. USA. May 1987; 84 (9): 2926-2930).*
Chien et al. (Proc. Natl. Acad. Sci. USA. Jul. 1989; 86 (14): 5532-5536).*
Winkler et al. (J. Immunol. Oct. 15, 2000; 165 (8): 4505-4514).*
Caldas et al. (Mol. Immunol. May 2003; 39 (15): 941-952).*
Vajdos et al. (J. Mol. Biol. Jul. 5, 2002; 320 (2): 415-428).*
De Pascalis et al. (J. Immunol. 2002; 169 (6): 3076-3084).*
Casset et al. (Biochem. Biophys. Res. Commun. Jul. 18, 2003; 307 (1): 198-205).*

(Continued)

*Primary Examiner* — Stephen L Rawlings
(74) *Attorney, Agent, or Firm* — FOLEY & LARDNER LLP

(57) ABSTRACT

The present disclosure provides antibodies and antigen-binding fragments thereof that bind to human OX40 (ACT35, CD134, or TNFRSF4), a pharmaceutical composition comprising said antibody, and use of the antibody or the composition for treating a disease, such as cancer. In particular, the anti-OX40 antibody of the present invention does not interfere with the binding of OX40-ligand to its receptor.

17 Claims, 16 Drawing Sheets

Specification includes a Sequence Listing.

(56) References Cited

FOREIGN PATENT DOCUMENTS

| WO | WO-2015153513 A1 | 10/2015 | |
|---|---|---|---|
| WO | WO-2016054555 A2 | 4/2016 | |
| WO | WO-2016057667 A1 | 4/2016 | |
| WO | WO-2016073282 A1 | 5/2016 | |
| WO | WO-2016081384 A1 | 5/2016 | |
| WO | WO 2016/139482 | 9/2016 | |
| WO | WO-2016/139482 A1 | 9/2016 | |
| WO | WO 2016/196228 | 12/2016 | |
| WO | WO-2016200836 A1 | 12/2016 | |
| WO | WO 2017/063162 | 4/2017 | |
| WO | WO-2017077085 A2 | 5/2017 | |
| WO | WO 2018/031490 | 2/2018 | |
| WO | WO-2018/031490 A2 | 2/2018 | |
| WO | WO-2019100320 A1 | 5/2019 | |
| WO | WO 2019/223733 | 11/2019 | |
| WO | WO-2019223733 A1 * | 11/2019 | ........... A61K 31/337 |
| WO | WO-2021098748 A1 | 5/2021 | |
| WO | WO-2021098757 A1 | 5/2021 | |
| WO | WO-2021098758 A1 | 5/2021 | |
| WO | WO-2021098769 A1 | 5/2021 | |
| WO | WO-2021098774 A1 | 5/2021 | |
| WO | WO-2021098777 A1 | 5/2021 | |

OTHER PUBLICATIONS

MacCallum et al. (J. Mol. Biol. Oct. 11, 1996; 262 (5): 732-745).*
Holm et al. (Mol. Immunol. Feb. 2007; 44 (6): 1075-1084).*
Zhang et al. (J. Biol. Chem. Dec. 30, 2016; 291 (53): 27134-46).*
Yang et al. (FEBS Lett. Jun. 2021; 595 (11): 1587-1603).*
Willoughby et al. (Mol. Immunol. Mar. 2017; 83: 13-22).*
Zhang et al. (Biomolecules. Aug. 31, 2022; 12 (9): 1209).*
Byun et al. (J. Exp. Med. Aug. 26, 2013; 210 (9): 1743-59).*
Aalberse, R.C. et al. (2002). "IgG4 breaking the rules," Immunology 105:9-19.
Angal S., et al., "A Single Amino Acid Substitution Abolishes the Heterogeneity of Chimeric Mouse/human (IgG4) Antibody," Molecular Immunology, Jan. 1993, vol. 30, pp. 105-108.
Armour, K.L. et al. (1999). "Recombinant human IgG molecules lacking Fc receptor I binding and monocyte triggering activities," Eur. J. Immunol. 29:2613-2624.
Arnold, James N. et al., "The Impact of Glycosylation on the Biological Function and Structure of Human Immunoglobulins," Annu. Rev. Immunol., 2007, vol. 25, pp. 21-50.
Brusco, A. et al., "Molecular characterization of immunoglobulin G4 gene isoallotypes," European Journal of Immunogenetics, 1998, vol. 25, pp. 349-355.
Chappel, et al., "Identification of the Fc receptor class I binding site in human IgG through the use of recombinant IgG1/IgG2 hybrid and point-mutated antibodies." Proc. Natl. Acad. Sci. USA (1991); 88: 9036-9040.
Chen, M.S. et al., "Effect of PLGA nanoparticles conjugated with anti-OX40/anti-AFP mAbs on cytotoxicity of CTL cells against hepatocellular carcinoma," Chinese Journal of Cellular and Molecular Immunology, Dec. 31, 2014, vol. 30, No. 4, pp. 337-341.
Clynes, R. A. et al., "Inhibitory Fc receptors modulate in vivo cytoxicity against tumor targets," Nat. Med. 6(4):443-446 (Apr. 2000).
Colombo, M.P., "On OX40 and PD-1 Combination: Why Should OX40 Be the First in Sequence?" Clin Cancer Res., Oct. 15, 2017, vol. 23, No. 20, pp. 5999-6001.
Extended Supplementary Search Report and Opinion in EP Application No. 19806419.8, dated Feb. 1, 2022, 9 pages.
Glanville, J. et al., "Precise determination of the diversity of a combinatorial antibody library gives insight into the human immunoglobulin repertoire," PNAS, 106(48):20216-20221 (Dec. 2009).
Guo, Z.Q. et al., "PD-1 blockade and OX40 triggering synergestically protects against tumor growth in a murine model of ovarian cancer," PLOS ONE, Feb. 27, 2014, vol. 9, No. 2, e89350, 10 pages.

International Search Report and Written Opinion for International Application No. PCT/CN2020/129964, mailed Feb. 19, 2021, 14 pages.
International Search Report and Written Opinion for International Application No. PCT/CN2020/129992, mailed May 27, 2021, 12 pages.
International Search Report and Written Opinion for International Application No. PCT/CN2020/130003, mailed Feb. 19, 2021, 14 pages.
International Search Report and Written Opinion for International Application No. PCT/CN2020/130059, mailed May 27, 2021, 9 pages.
International Search Report and Written Opinion for International Application No. PCT/CN2020/130075, mailed May 27, 2021, 16 pages.
International Search Report and Written Opinion for International Application No. PCT/CN2020/130103, mailed May 27, 2021, 13 pages.
Jefferis, Roy et al., "Human immunoglobulin allotypes," mAbs, 2009, vol. 1, Issue 4, pp. 332-338.
Linch, S.N. et al., "OX40 Agonists and Combination Immunotherapy: Putting the Pedal to the Metal," Frontiers in Oncology, vol. 5, Feb. 16, 2015, Article 34, pp. 1-14.
Lund et al., "Oligosaccharide-protein interactions in IgG can modulate recognition by Fcγ receptors," Research Communications, the FASEB Journal, Feb. 1995, vol. 9, Issue 1, p. 116-119.
Moore et al., "Engineered Fc variant antibodies with enhanced ability to recruit complement and mediate effector functions," Landes Biosciences, mAbs 2(2): 181-189, Mar./Apr. 2010.
Pachter, J.A. et al., "The Dual PI3K-b, y inhibitor Duvelisib stimulates anti-tumor immunity and enhances efficacy of immune checkpoint and co-stimulatory antibodies in a B cell lymphoma model," Blood, Dec. 7, 2017, vol. 130, No. Supplement 1, p. 1541-42.
Pachter, J.A. et al., "Synergistic efficacy of duvelisib with checkpoint or co-stimulatory antibodies in a B cell lymphoma model: advantages of dual inhibition of PI3K-b and PI3K-y," the 33rd Annual meeting of the society for immunotherapy of cancer, 2018, pp. 533-534.
Shields, et al., "High Resolution Mapping of the Binding Site on Human IgG1 for FcRI, FcrII, FcrIII, and FcRn and Design of IgG1 Variants with Improved Binding to the FcR*," J. Biol. Chem. (2001); 276: 6591-6604.
Yang, Y. et al., "Antitumor T-cell responses contribute to the effects of dasatinib on c-KIT mutant murine mastocytoma and are potentiated by anti-OX40," Blood, Nov. 29, 2012, vol. 120, No. 23, 11 pages.
Zhang, P. et al., "Ligand-blocking and membrane-proximal domain targeting anti-OX40 antibodies mediated potent T cell-stimulatory and anti-Tumor activity," Cell Reports, Jun. 11, 2019, vol. 27, pp. 3117-3123.
Office Action with Search Report for Chinese Patent Application No. 201980034638.8 dated Sep. 9, 2023.
International Search Report and Written Opinion for International Application No. PCT/CN2019/088013, mailed Aug. 21, 2019, 9 pages.
Al-Shamkhani, A. et al. (1996). OX40 is differentially expressed on activated rat and mouse T cells and is the sole receptor for the OX40 ligand. European Journal of Immunology 26, 1695-1699.
An, Z. et al. (2009). IgG2m4, an engineered antibody isotype with reduced Fc function. mAbs, 1:6, 572-579, DOI: 10.4161/mabs.1.6. 10185.
Arch, R. H. et al. (1998). 4-1BB and Ox40 are members of a tumor necrosis factor (TNF)-nerve growth factor receptor subfamily that bind TNF receptor-associated factors and activate nuclear factor kappaB. Molecular and Cellular Biology 18(1):558-565.
Aspeslagh, S. et al. (2016). Rationale for anti-OX40 cancer immunotherapy. Eur J Cancer 52, 50-66.
Brocks, B. et al. (2001). Species-crossreactive scFv against the tumor stroma marker "fibroblast activation protein" selected by phage display from an immunized FAP-/- knock-out mouse, Mol Med. 7(7):461469.

(56) References Cited

OTHER PUBLICATIONS

Bulliard, Y. et al. (2014). OX40 engagement depletes intratumoral Tregs via activating FcgammaRs, leading to antitumor efficacy. Immunology and Cell Biology 92, 475-480.
Calderhead, D.M. et al. (1993). Cloning of mouse Ox40: a T cell activation marker that may mediate T-B cell interactions. J Immunol 151, 5261-5271.
Carboni, S. et al. (2003). CD134 plays a crucial role in the pathogenesis of EAE and is upregulated in the CNS of patients with multiple sclerosis. Journal of Neuroimmunology 145, 1-11.
Compaan, D.M. et al. (2006). The crystal structure of the costimulatory OX40-OX40L complex. Structure 14, 1321-1330.
Croft, M. (2010). Control of immunity by the TNFR-related molecule OX40 (CD134). Annual Review of Immunology 28, 57-78.
Croft, M. et al. (2009). The significance of OX40 and OX40L to T-cell biology and immune disease. Immunological Reviews 229, 173-191.
Curti, B.D. et al. (2013). OX40 is a potent immune-stimulating target in late-stage cancer patients. Cancer Research 73, 7189-7198.
Durkop, H. et al. (1995). Expression of the human OX40 (hOX40) antigen in normal and neoplastic tissues. British Journal of Haematology 91, 927-931.
Gough, M.J. et al. (2009). OX40 (CD134) and OX40L. Advances in Experimental Medicine and Biology 647, 94-107.
Gramaglia, I. et al. (1998). Ox-40 ligand: a potent costimulatory molecule for sustaining primary CD4 T cell responses. J Immunol 161, 6510-6517.
Guo, Z. et al. (2013). Combined TIM-3 blockade and CD137 activation affords the long-term protection in a murine model of ovarian cancer. Journal of Translational Medicine 11, 215.
Hori, S. et al. (2003). Control of regulatory T cell development by the transcription factor Foxp3. Science 299, 1057-1061.
Huddleston, C.A. et al. (2006). OX40 (CD134) engagement drives differentiation of CD4+ T cells to effector cells. European Journal of Immunology 36, 1093-1103.
Ito, T. et al. (2004). Plasmacytoid dendritic cells regulate Th cell responses through OX40 ligand and type I IFNs. J Immunol 172, 4253-4259.
Ito, T. et al. (2006). OX40 ligand shuts down IL-10-producing regulatory T cells. Proceedings of the National Academy of Sciences of the United States of America 103, 13138-13143.
Jacquemin, C. et al. (2015). OX40 Ligand Contributes to Human Lupus Pathogenesis by Promoting T Follicular Helper Response. Immunity 42, 1159-1170.
Kjaergaard, J. et al. (2000). Therapeutic efficacy of OX-40 receptor antibody depends on tumor immunogenicity and anatomic site of tumor growth. Cancer Research 60, 5514-5521.
Ladanyi, A. et al. (2004). T-cell activation marker expression on tumor-infiltrating lymphocytes as prognostic factor in cutaneous malignant melanoma. Clinical cancer research : an official journal of the American Association for Cancer Research 10, 521-530.
Lai, C. et al. (2016). OX40+ Regulatory T Cells in Cutaneous Squamous Cell Carcinoma Suppress Effector T-Cell Responses and Associate with Metastatic Potential. Clinical cancer research : an official journal of the American Association for Cancer Research 22, 4236-4248.
Marabelle, A. et al. (2013). Intratumoral anti-CTLA-4 therapy: enhancing efficacy while avoiding toxicity. Clinical cancer research : an official journal of the American Association for Cancer Research 19, 5261-5263.
Marabelle, A. et al. (2013). Depleting tumor-specific Tregs at a single site eradicates disseminated tumors. The Journal of Clinical Investigation 123, 2447-2463.
Montler, R. et al. (2016). OX40, PD-1 and CTLA-4 are selectively expressed on tumor-infiltrating T cells in head and neck cancer. Clinical & Translational Immunology 5, e70; doi: 10.1038/cti.2016.16, 8 pages.
Morris, N.P. et al. (2007). Development and characterization of recombinant human Fc:OX40L fusion protein linked via a coiled-coil trimerization domain. Molecular Immunology 44, 3112-3121.
Ohshima, Y. et al. (1997). Expression and function of OX40 ligand on human dendritic cells. J Immunol 159, 3838-3848.
Petty, J. K. et al. (2002). Survival in human colorectal cancer correlates with expression of the T-cell costimulatory molecule OX-40 (CD134). American Journal of Surgery 183, 512-518.
Redmond, W. L. (2007). Targeting OX40 and OX40L for the treatment of autoimmunity and cancer. Critical Reviews in Immunology, 27(5):415-436.
Rogers, P. R. et al. (2001). OX40 promotes Bcl-xL and Bcl-2 expression and is essential for long-term survival of CD4 T cells. Immunity 15, 445-455.
Ruby, C. E. et al. (2009). OX40-enhanced tumor rejection and effector T cell differentiation decreases with age. J Immunol 182, 1481-1489.
Sarff, M. et al. (2008). OX40 (CD134) expression in sentinel lymph nodes correlates with prognostic features of primary melanomas. American Journal of Surgery 195, 621-625.
Sato, T. et al. (2002). Consequences of OX40-OX40 ligand interactions in langerhans cell function: enhanced contact hypersensitivity responses in OX40L-transgenic mice. European Journal of Immunology 32, 3326-3335.
Smyth, M. J. et al. (2014). Targeting regulatory T cells in tumor immunotherapy. Immunology and Cell Biology 92, 473-474.
Song, A. et al. (2005a). OX40 and Bcl-xL promote the persistence of CD8 T cells to recall tumor-associated antigen. J Immunol 175, 3534-3541.
Song, J. et al. (2005). Sustained survivin expression from OX40 costimulatory signals drives T cell clonal expansion. Immunity 22, 621-631.
Song, J. et al. (2008). Activation of NF-kappaB1 by OX40 contributes to antigen-driven T Cell expansion and survival. J Immunol 180, 7240-7248.
Soroosh, P. et al. (2007). Differential requirements for OX40 signals on generation of effector and central memory CD4+ T cells. J Immunol 179, 5014-5023.
St. Rose, M. C. et al. (2013). CD134/CD137 dual costimulation-elicited IFN-gamma maximizes effector T-cell function but limits Treg expansion. Immunology and Cell Biology 91, 173-183.
Stuber, E. et al. (1995). Cross-linking of OX40 ligand, a member of the TNF/NGF cytokine family, induces proliferation and differentiation in murine splenic B cells. Immunity 2, 507-521.
Szypowska, A. et al. (2014). High expression of OX40 (CD134) and 4-1BB (CD137) molecules on CD4(+)CD25(high) cells in children with type 1 diabetes. Advances in Medical Sciences 59, 39-43.
Timperi, E. et al. (2016). Regulatory T cells with multiple suppressive and potentially pro-tumor activities accumulate in human colorectal cancer. OncoImmunology 5:7, e1175800, DOI: 10.1080/2162402X.2016.1175800.
Tourkova, I. L. et al. (2001). Mechanisms of dendritic cell-induced T cell proliferation in the primary MLR assay. Immunology Letters 78, 75-82.
Vetto, J. T. et al. (1997). Presence of the T-cell activation marker OX-40 on tumor infiltrating lymphocytes and draining lymph node cells from patients with melanoma and head and neck cancers. American Journal of Surgery 174, 258-265.
Voo, K. S. et al. (2013). Antibodies targeting human OX40 expand effector T cells and block inducible and natural regulatory T cell function. J Immunol 191, 3641-3650.
Weinberg, A. D. et al. (2000). Engagement of the OX-40 receptor in vivo enhances antitumor immunity. J Immunol 164, 2160-2169.
Weinberg, A. D. et al. (1999). Blocking OX-40/OX-40 ligand interaction in vitro and in vivo leads to decreased T cell function and amelioration of experimental allergic encephalomyelitis. J Immunol 162, 1818-1826.
Willoughby, J. et al. (2017). OX40: Structure and function—What questions remain? Molecular Immunology 83, 13-22.
Zander, R. A. et al. (2015). PD-1 Co-inhibitory and OX40 Co-stimulatory Crosstalk Regulates Helper T Cell Differentiation and Anti-Plasmodium Humoral Immunity. Cell Host & Microbe 17, 628-641.
Zhang, T. (2005). Chimeric NK-receptor-bearing T cells mediate antitumor immunotherapy. Blood 106, 1544-1551.

(56) References Cited

OTHER PUBLICATIONS

Notice of Reasons for Rejection issued in co-pending Japanese Patent Application No. 2020-565492, dated Oct. 24, 2023.
Official Action issued in Mexican Patent Application No. MX/a/2020/012567, dated May 24, 2024. [Translation p. 9-13).
Turaj, et al., "Augmentation of CD134 (OX40)-dependent NK antitumor activity is dependent on antibody cross-linking," Sci. Rep 8, 2278, 12 pages (2018).

* cited by examiner

| Heavy chain | | Light chain | | Co-transfection with heavy chain and light chain | FACS | | | Biacore | | |
|---|---|---|---|---|---|---|---|---|---|---|
| ID | CDR/FR | ID | CDR/FR | Ab ID | EC50(ng/ml) | Top(MFI) | | ka (M⁻¹s⁻¹) | kd (s⁻¹) | $K_D$ (M) |
| 445-1VH | - | 445-1VL | - | 445-1 | 336 | 500 | | 2.37E+05 | 3.89E-03 | 1.64E-08 |
| 445-1VH-M48I | FR2 | 445-1VL | - | 445-2(M48I)-1 (445-1 with M48I mutation on Vh) | 353 | 480 | | 2.30E+05 | 3.56E-03 | 1.55E-08 |
| 445-1VH | - | 445-1VL-S24G | CDR1 | 445-1-2(S24G) (445-1 with S24G mutation on VL) | 307 | 470 | | 2.22E+05 | 3.60E-03 | 1.62E-08 |
| 445-1VH | - | 445-1VL-S10T/E81D/D70E | FR1/FR3 | 445-1-2(S10T/E81D/D70E) (445-1 with S10T, E81D and D70E mutations on VL) | 280 | 510 | | 2.28E+05 | 3.40E-03 | 1.49E-08 |

Figure 14B

| Heavy chain | | Light chain | | | Co-transfection with heavy chain and light chain | FACS | | Biacore | | |
|---|---|---|---|---|---|---|---|---|---|---|
| ID | CDR/FR | ID | CDR/FR | CDR/FR | Ab ID | EC$_{50}$(ng/ml) | Top(MFI) | ka (M$^{-1}$s$^{-1}$) | kd (s$^{-1}$) | K$_D$ (M) |
| 445-2VH | - | 445-2VL | - | - | 445-2 | 397 | 760 | 2.06E+05 | 2.64E-03 | 1.28E-08 |
| 445-2VH-Q62E-Q65K | CDR2 | 445-2VL-S24R | CDR2 | CDR1 | 445-3(Q62E-Q65K)-3(S24R) (445-2 with Q62E and Q65K mutations on VH and S24R mutation on VL) | 318 | 790 | 1.87E+05 | 2.32E-03 | 1.24E-08 |
| 445-2VH-Q62E | CDR2 | 445-2VL-S24R | CDR2 | CDR1 | 445-3(Q62E)-3(S24R) (445-2 with Q62E mutation on VH and S24R mutation on VL) | 363 | 760 | 1.94E+05 | 2.27E-03 | 1.17E-08 |
| 445-2VH-K28T | CDR1 | 445-2VL-S24R | FR1 | CDR1 | 445-3(K28T)-3(S24R) (445-2 with K28T mutation on VH and S24R mutation on VL) | 660 | 750 | 4.44E+05 | 5.74E-03 | 1.29E-08 |
| 445-2VH-Y27G | CDR1 | 445-2VL-S24R | FR1 | CDR1 | 445-3(Y27G)-3(S24R) (445-2 with Y27G mutation on VH and S24R mutation on VL) | 755 | 630 | 6.25E+04 | 1.35E-03 | 2.15E-08 |
| 445-2VH-T30S | CDR1 | 445-2VL-S24R | FR1 | CDR1 | 445-3(T30S)-3(S24R) (445-2 with T30S mutation on VH and S24R mutation on VL) | 405 | 800 | 2.91E+05 | 3.81E-03 | 1.31E-08 |
| 445-3VH | - | 445-3VL | - | - | 445-3 | 462 | 990 | 1.74E+05 | 1.48E-03 | 8.51E-09 |
| 445-2VH-A61N-K28R | CDR2/FR1 | 445-3VL | - | - | 445-3(A61N-K28R)-3 (445-2 VH with A61N and K28R mutations and 445-3 VL) | 369 | 1080 | 1.57E+05 | 1.15E-03 | 7.35E-09 |
| 445-2VH-A61N-K63R | CDR2 | 445-3VL | - | - | 445-3(A61N-K63R)-3 (445-2 VH with A61N and K63R mutations and 445-3 VL) | 483 | 1100 | 1.61E+05 | 1.55E-03 | 9.65E-09 |
| 445-3VH | - | 445-2VL-G41D-K42G-S24R-K93R | - | FR2/CDR1/CDR3 | 445-3-3(G41D-K42G-S24R-K93R) (445-3 VH and 445-2 VL with G41D, K42G, S24R and K93R mutations) | 337 | 1050 | 2.12E+05 | 1.68E-03 | 7.90E-09 |

SEQUENCE LISTING

<160> NUMBER OF SEQ ID NOS: 31

<210> SEQ ID NO 1
<211> LENGTH: 277
<212> TYPE: PRT
<213> ORGANISM: Homo sapiens

<400> SEQUENCE: 1

```
Met Cys Val Gly Ala Arg Arg Leu Gly Arg Gly Pro Cys Ala Ala Leu
1               5                   10                  15

Leu Leu Leu Gly Leu Gly Leu Ser Thr Val Thr Gly Leu His Cys Val
            20                  25                  30

Gly Asp Thr Tyr Pro Ser Asn Asp Arg Cys Cys His Glu Cys Arg Pro
        35                  40                  45

Gly Asn Gly Met Val Ser Arg Cys Ser Arg Ser Gln Asn Thr Val Cys
    50                  55                  60

Arg Pro Cys Gly Pro Gly Phe Tyr Asn Asp Val Val Ser Ser Lys Pro
65                  70                  75                  80

Cys Lys Pro Cys Thr Trp Cys Asn Leu Arg Ser Gly Ser Glu Arg Lys
                85                  90                  95

Gln Leu Cys Thr Ala Thr Gln Asp Thr Val Cys Arg Cys Arg Ala Gly
            100                 105                 110

Thr Gln Pro Leu Asp Ser Tyr Lys Pro Gly Val Asp Cys Ala Pro Cys
        115                 120                 125

Pro Pro Gly His Phe Ser Pro Gly Asp Asn Gln Ala Cys Lys Pro Trp
    130                 135                 140
```

```
Thr Asn Cys Thr Leu Ala Gly Lys His Thr Leu Gln Pro Ala Ser Asn
145                 150                 155                 160

Ser Ser Asp Ala Ile Cys Glu Asp Arg Asp Pro Pro Ala Thr Gln Pro
                165                 170                 175

Gln Glu Thr Gln Gly Pro Pro Ala Arg Pro Ile Thr Val Gln Pro Thr
            180                 185                 190

Glu Ala Trp Pro Arg Thr Ser Gln Gly Pro Ser Thr Arg Pro Val Glu
        195                 200                 205

Val Pro Gly Gly Arg Ala Val Ala Ala Ile Leu Gly Leu Gly Leu Val
    210                 215                 220

Leu Gly Leu Leu Gly Pro Leu Ala Ile Leu Leu Ala Leu Tyr Leu Leu
225                 230                 235                 240

Arg Arg Asp Gln Arg Leu Pro Pro Asp Ala His Lys Pro Pro Gly Gly
                245                 250                 255

Gly Ser Phe Arg Thr Pro Ile Gln Glu Glu Gln Ala Asp Ala His Ser
            260                 265                 270

Thr Leu Ala Lys Ile
        275

<210> SEQ ID NO 2
<211> LENGTH: 216
<212> TYPE: PRT
<213> ORGANISM: Homo sapiens

<400> SEQUENCE: 2

Met Cys Val Gly Ala Arg Arg Leu Gly Arg Gly Pro Cys Ala Ala Leu
1               5                   10                  15

Leu Leu Leu Gly Leu Gly Leu Ser Thr Val Thr Gly Leu His Cys Val
            20                  25                  30

Gly Asp Thr Tyr Pro Ser Asn Asp Arg Cys Cys His Glu Cys Arg Pro
        35                  40                  45

Gly Asn Gly Met Val Ser Arg Cys Ser Arg Ser Gln Asn Thr Val Cys
    50                  55                  60

Arg Pro Cys Gly Pro Gly Phe Tyr Asn Asp Val Val Ser Ser Lys Pro
65                  70                  75                  80

Cys Lys Pro Cys Thr Trp Cys Asn Leu Arg Ser Gly Ser Glu Arg Lys
                85                  90                  95

Gln Leu Cys Thr Ala Thr Gln Asp Thr Val Cys Arg Cys Arg Ala Gly
            100                 105                 110

Thr Gln Pro Leu Asp Ser Tyr Lys Pro Gly Val Asp Cys Ala Pro Cys
        115                 120                 125

Pro Pro Gly His Phe Ser Pro Gly Asp Asn Gln Ala Cys Lys Pro Trp
    130                 135                 140

Thr Asn Cys Thr Leu Ala Gly Lys His Thr Leu Gln Pro Ala Ser Asn
145                 150                 155                 160

Ser Ser Asp Ala Ile Cys Glu Asp Arg Asp Pro Pro Ala Thr Gln Pro
                165                 170                 175

Gln Glu Thr Gln Gly Pro Pro Ala Arg Pro Ile Thr Val Gln Pro Thr
            180                 185                 190

Glu Ala Trp Pro Arg Thr Ser Gln Gly Pro Ser Thr Arg Pro Val Glu
        195                 200                 205

Val Pro Gly Gly Arg Ala Val Ala
    210                 215

<210> SEQ ID NO 3
```

```
<211> LENGTH: 5
<212> TYPE: PRT
<213> ORGANISM: Mus musculus

<400> SEQUENCE: 3

Ser Tyr Ile Ile His
1               5

<210> SEQ ID NO 4
<211> LENGTH: 17
<212> TYPE: PRT
<213> ORGANISM: Mus musculus

<400> SEQUENCE: 4

Tyr Ile Asn Pro Tyr Asn Asp Gly Thr Arg Tyr Asn Glu Lys Phe Lys
1               5                   10                  15

Gly

<210> SEQ ID NO 5
<211> LENGTH: 11
<212> TYPE: PRT
<213> ORGANISM: Mus musculus

<400> SEQUENCE: 5

Gly Tyr Tyr Gly Ser Ser Tyr Ala Met Asp Tyr
1               5                   10

<210> SEQ ID NO 6
<211> LENGTH: 11
<212> TYPE: PRT
<213> ORGANISM: Mus musculus

<400> SEQUENCE: 6

Ser Ala Ser Gln Gly Ile Ser Asn Tyr Leu Asn
1               5                   10

<210> SEQ ID NO 7
<211> LENGTH: 7
<212> TYPE: PRT
<213> ORGANISM: Mus musculus

<400> SEQUENCE: 7

Asp Thr Ser Thr Leu Tyr Ser
1               5

<210> SEQ ID NO 8
<211> LENGTH: 9
<212> TYPE: PRT
<213> ORGANISM: Mus musculus

<400> SEQUENCE: 8

Gln Gln Tyr Ser Lys Leu Pro Tyr Thr
1               5

<210> SEQ ID NO 9
<211> LENGTH: 120
<212> TYPE: PRT
<213> ORGANISM: Mus musculus

<400> SEQUENCE: 9

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Lys Phe Thr Ser Tyr
            20                  25                  30
```

Ile Ile His Trp Val Lys Gln Lys Pro Gly Gln Gly Leu Glu Trp Ile
            35                  40                  45

Gly Tyr Ile Asn Pro Tyr Asn Asp Gly Thr Arg Tyr Asn Glu Lys Phe
        50                  55                  60

Lys Gly Lys Ala Thr Leu Thr Ser Asp Lys Ser Ser Thr Ala Tyr
65                  70                  75                  80

Met Glu Tyr Ser Ser Leu Thr Ser Glu Asp Ser Ala Val Tyr Tyr Cys
                85                  90                  95

Ala Arg Gly Tyr Tyr Gly Ser Ser Tyr Ala Met Asp Tyr Trp Gly Gln
                100                 105                 110

Gly Thr Ser Val Thr Val Ser Ser
            115                 120

<210> SEQ ID NO 10
<211> LENGTH: 360
<212> TYPE: DNA
<213> ORGANISM: Mus musculus

<400> SEQUENCE: 10
gaggtccagc tgcagcagtc tggacctgaa ctggtaaagc ctggggcttc agtgaagatg      60
tcctgcaagg cttctggata taaattcact agctatatta tacactgggt gaagcagaag     120
cctgggcagg gccttgagtg gattggatat attaatcctt acaatgatgg tactaggtac     180
aatgagaagt tcaaaggcaa ggccacactg acttcagaca atcctccag cacagcctac     240 atggagtaca gcagcctgac ctctgaggac tctgcggtct attactgtgc aaggggttac     300
tacggtagta gctatgctat ggactactgg ggtcaaggaa cctcagtcac cgtctcctca     360

<210> SEQ ID NO 11
<211> LENGTH: 107
<212> TYPE: PRT
<213> ORGANISM: Mus musculus

<400> SEQUENCE: 11

Asp Ile Gln Met Thr Gln Thr Thr Ser Ser Leu Ser Ala Ser Leu Gly
1               5                   10                  15

Asp Arg Val Thr Ile Ser Cys Ser Ala Ser Gln Gly Ile Ser Asn Tyr
                20                  25                  30

Leu Asn Trp Tyr Gln Gln Lys Pro Asp Gly Thr Ile Lys Leu Leu Ile
            35                  40                  45

Tyr Asp Thr Ser Thr Leu Tyr Ser Gly Val Pro Ser Arg Phe Ser Gly
        50                  55                  60

Ser Gly Ser Gly Thr Asp Tyr Phe Leu Thr Ile Ser Asn Leu Glu Pro
65                  70                  75                  80

Glu Asp Ile Ala Thr Tyr Tyr Cys Gln Gln Tyr Ser Lys Leu Pro Tyr
                85                  90                  95

Thr Phe Gly Gly Gly Thr Lys Leu Glu Lys Lys
            100                 105

<210> SEQ ID NO 12
<211> LENGTH: 321
<212> TYPE: DNA
<213> ORGANISM: Mus musculus

<400> SEQUENCE: 12
gatatccaga tgacacagac tacatcctcc ctgtctgcct ctctgggaga cagagtcacc      60
atcagttgca gtgcaagtca gggcattagc aattatttaa actggtatca gcagaaacca     120

```
gatggaacta ttaaactcct gatctatgac acatcaacct tatactcagg agtcccatca    180
aggttcagtg gcagtgggtc tgggacagat tattttctca ccatcagcaa cctggaacct    240
gaagatattg ccacttacta ttgtcagcag tatagtaagc ttccgtacac gttcggaggg    300
gggaccaagc tggaaaaaaa a                                              321
```

<210> SEQ ID NO 13
<211> LENGTH: 17
<212> TYPE: PRT
<213> ORGANISM: Artificial Sequence
<220> FEATURE:
<223> OTHER INFORMATION: 445-1 HCDR2

<400> SEQUENCE: 13

```
Tyr Ile Asn Pro Tyr Asn Asp Gly Thr Arg Tyr Asn Gln Lys Phe Gln
1               5                   10                  15

Gly
```

<210> SEQ ID NO 14
<211> LENGTH: 120
<212> TYPE: PRT
<213> ORGANISM: Artificial Sequence
<220> FEATURE:
<223> OTHER INFORMATION: 445-1 VH pro

<400> SEQUENCE: 14

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Lys Phe Thr Ser Tyr
                20                  25                  30

Ile Ile His Trp Val Arg Gln Ala Pro Gly Gln Gly Leu Glu Trp Met
            35                  40                  45

Gly Tyr Ile Asn Pro Tyr Asn Asp Gly Thr Arg Tyr Asn Gln Lys Phe
        50                  55                  60

Gln Gly Arg Val Thr Leu Thr Ser Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Tyr Tyr Gly Ser Ser Tyr Ala Met Asp Tyr Trp Gly Gln
            100                 105                 110

Gly Thr Thr Val Thr Val Ser Ser
        115                 120
```

<210> SEQ ID NO 15
<211> LENGTH: 360
<212> TYPE: DNA
<213> ORGANISM: Artificial Sequence
<220> FEATURE:
<223> OTHER INFORMATION: 445-1 VH DNA

<400> SEQUENCE: 15

```
caggtgcagc tggtgcagtc tggagcagag gtgaagaagc caggcagctc cgtgaaggtg     60
tcctgcaagg cctctggcta caagttcacc tcctatatca tccactgggt gcggcaggca    120
ccaggacagg gactggagtg gatgggctac atcaacccct ataatgacgg cacacggtac    180
aaccagaagt tcagggcag agtgaccctg acaagcgata gtctaccag cacagcctat     240 atggagctgt ctagcctgag gtccgaggac accgccgtgt actattgtgc cagaggctac    300
tatggctcct cttacgccat ggattattgg ggccagggca ccacagtgac agtgagctcc    360
```

```
<210> SEQ ID NO 16
<211> LENGTH: 107
<212> TYPE: PRT
<213> ORGANISM: Artificial Sequence
<220> FEATURE:
<223> OTHER INFORMATION: 445-1 VK pro

<400> SEQUENCE: 16
```

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Gly Ile Ser Asn Tyr
            20                  25                  30

Leu Asn Trp Tyr Gln Gln Lys Pro Gly Lys Ala Ile Lys Leu Leu Ile
        35                  40                  45

Tyr Asp Thr Ser Thr Leu Tyr Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Tyr Ser Lys Leu Pro Tyr
                85                  90                  95

Thr Phe Gly Gly Gly Thr Lys Val Glu Ile Lys
            100                 105

```
<210> SEQ ID NO 17
<211> LENGTH: 321
<212> TYPE: DNA
<213> ORGANISM: Artificial Sequence
<220> FEATURE:
<223> OTHER INFORMATION: 445-1 VK DNA

<400> SEQUENCE: 17
```
gacatccaga tgacccagtc tcccagctcc ctgtccgcct ctgtgggcga tagggtgacc    60
atcacatgca gcgcctccca gggcatctcc aactacctga attggtatca gcagaagcca   120
ggcaaggcca tcaagctgct gatctacgac acctctacac tgtatagcgg cgtgccctcc   180
agattctctg gcagcggctc cggaaccgac tacaccctga caatctctag cctgcagccc   240
gaggatttcg ccacatacta ttgtcagcag tacagcaagc tgccttatac ctttggcggc   300
ggcacaaagg tggagatcaa g                                             321

```
<210> SEQ ID NO 18
<211> LENGTH: 17
<212> TYPE: PRT
<213> ORGANISM: Artificial Sequence
<220> FEATURE:
<223> OTHER INFORMATION: 445-2 HCDR2

<400> SEQUENCE: 18
```

Tyr Ile Asn Pro Tyr Asn Glu Gly Thr Arg Tyr Ala Gln Lys Phe Gln
1               5                   10                  15

Gly

```
<210> SEQ ID NO 19
<211> LENGTH: 7
<212> TYPE: PRT
<213> ORGANISM: Artificial Sequence
<220> FEATURE:
<223> OTHER INFORMATION: 445-2 LCDR2
```

<400> SEQUENCE: 19

Asp Ala Ser Thr Leu Tyr Ser
1               5

<210> SEQ ID NO 20
<211> LENGTH: 120
<212> TYPE: PRT
<213> ORGANISM: Artificial Sequence
<220> FEATURE:
<223> OTHER INFORMATION: 445-2 VH pro

<400> SEQUENCE: 20

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Lys Phe Thr Ser Tyr
            20                  25                  30

Ile Ile His Trp Val Arg Gln Ala Pro Gly Gln Gly Leu Glu Trp Met
        35                  40                  45

Gly Tyr Ile Asn Pro Tyr Asn Glu Gly Thr Arg Tyr Ala Gln Lys Phe
    50                  55                  60

Gln Gly Arg Val Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Tyr Tyr Gly Ser Ser Tyr Ala Met Asp Tyr Trp Gly Gln
            100                 105                 110

Gly Thr Thr Val Thr Val Ser Ser
        115                 120

<210> SEQ ID NO 21
<211> LENGTH: 360
<212> TYPE: DNA
<213> ORGANISM: Artificial Sequence
<220> FEATURE:
<223> OTHER INFORMATION: 445-2 VH DNA

<400> SEQUENCE: 21
caggtgcagc tggtgcagtc tggagcagag gtgaagaagc caggcagctc cgtgaaggtg     60
tcctgcaagg cctctggcta caagttcacc tcctatatca tccactgggt gcggcaggca    120
ccaggacagg gactggagtg gatgggctac atcaacccct ataatgaggg cacacggtac    180
gcccagaagt tcagggcag agtgaccctg acagccgata agtctaccag cacagcctat    240
atggagctgt ctagcctgag gtccgaggac accgccgtgt actattgtgc cagaggctac    300
tatggctcct cttacgccat ggattattgg ggccagggca ccacagtgac agtgagctcc    360

<210> SEQ ID NO 22
<211> LENGTH: 107
<212> TYPE: PRT
<213> ORGANISM: Artificial Sequence
<220> FEATURE:
<223> OTHER INFORMATION: 445-2 VK pro

<400> SEQUENCE: 22

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Gly Ile Ser Asn Tyr
            20                  25                  30

```
Leu Asn Trp Tyr Gln Gln Lys Pro Gly Lys Ala Ile Lys Leu Leu Ile
         35                  40                  45

Tyr Asp Ala Ser Thr Leu Tyr Ser Gly Val Pro Ser Arg Phe Ser Gly
         50                  55                  60

Ser Gly Ser Gly Thr Asp Phe Thr Leu Thr Ile Ser Ser Leu Gln Pro
 65              70                  75                  80

Glu Asp Phe Ala Thr Tyr Tyr Cys Gln Gln Tyr Ser Lys Leu Pro Tyr
                 85                  90                  95

Thr Phe Gly Gly Gly Thr Lys Val Glu Ile Lys
            100                 105
```

```
<210> SEQ ID NO 23
<211> LENGTH: 321
<212> TYPE: DNA
<213> ORGANISM: Artificial Sequence
<220> FEATURE:
<223> OTHER INFORMATION: 445-2 VK DNA

<400> SEQUENCE: 23
gacatccaga tgacccagtc tcccagctcc ctgtccgcct ctgtgggcga tagggtgacc      60
atcacatgca gcgcctccca gggcatctcc aactacctga attggtatca gcagaagcca    120
ggcaaggcca tcaagctgct gatctacgac gcctctacac tgtatagcgg cgtgccctcc    180
agattctctg gcagcggctc cggaaccgac ttcaccctga caatctctag cctgcagccc    240
gaggatttcg ccacatacta ttgtcagcag tacagcaagc tgccttatac ctttggcggc    300
ggcacaaagg tggagatcaa g                                               321
```

```
<210> SEQ ID NO 24
<211> LENGTH: 17
<212> TYPE: PRT
<213> ORGANISM: Artificial Sequence
<220> FEATURE:
<223> OTHER INFORMATION: 445-3 HCDR2

<400> SEQUENCE: 24

Tyr Ile Asn Pro Tyr Asn Glu Gly Thr Arg Tyr Asn Gln Lys Phe Gln
1               5                   10                  15

Gly
```

```
<210> SEQ ID NO 25
<211> LENGTH: 11
<212> TYPE: PRT
<213> ORGANISM: Artificial Sequence
<220> FEATURE:
<223> OTHER INFORMATION: 445-3 LCDR1

<400> SEQUENCE: 25

Arg Ala Ser Gln Gly Ile Ser Asn Tyr Leu Asn
1               5                   10
```

```
<210> SEQ ID NO 26
<211> LENGTH: 120
<212> TYPE: PRT
<213> ORGANISM: Artificial Sequence
<220> FEATURE:
<223> OTHER INFORMATION: 445-3 VH pro

<400> SEQUENCE: 26

Gln Val Gln Leu Val Gln Ser Gly Ala Glu Val Lys Lys Pro Gly Ser
1               5                   10                  15
```

-continued

```
Ser Val Lys Val Ser Cys Lys Ala Ser Gly Tyr Lys Phe Thr Ser Tyr
            20                  25                  30

Ile Ile His Trp Val Arg Gln Ala Pro Gly Gln Gly Leu Glu Trp Met
        35                  40                  45

Gly Tyr Ile Asn Pro Tyr Asn Glu Gly Thr Arg Tyr Asn Gln Lys Phe
    50                  55                  60

Gln Gly Arg Val Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Tyr Tyr Gly Ser Ser Tyr Ala Met Asp Tyr Trp Gly Gln
            100                 105                 110

Gly Thr Thr Val Thr Val Ser Ser
            115                 120
```

<210> SEQ ID NO 27
<211> LENGTH: 360
<212> TYPE: DNA
<213> ORGANISM: Artificial Sequence
<220> FEATURE:
<223> OTHER INFORMATION: 445-3 VH DNA

<400> SEQUENCE: 27

```
caggtgcagc tggtgcagtc tggagcagag gtgaagaagc caggcagctc cgtgaaggtg      60
tcctgcaagg cctctggcta caagttcacc tcctatatca tccactgggt gcggcaggca     120
ccaggacagg gactggagtg gatgggctac atcaacccct ataatgaggg cacacgtac      180
aaccagaagt ttcagggcag agtgaccctg acagccgata gtctaccag cacagcctat     240
atggagctgt ctagcctgag gtccgaggac accgccgtgt actattgtgc cagaggctac     300
tatggctcct cttacgccat ggattattgg ggccagggca ccacagtgac agtgagctcc     360
```

<210> SEQ ID NO 28
<211> LENGTH: 107
<212> TYPE: PRT
<213> ORGANISM: Artificial Sequence
<220> FEATURE:
<223> OTHER INFORMATION: 445-3 VK pro

<400> SEQUENCE: 28

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Asn Trp Tyr Gln Gln Lys Pro Asp Gly Ala Ile Lys Leu Leu Ile
        35                  40                  45

Tyr Asp Ala Ser Thr Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Lys Leu Pro Tyr
                85                  90                  95

Thr Phe Gly Gly Gly Thr Lys Val Glu Ile Lys
            100                 105
```

<210> SEQ ID NO 29
<211> LENGTH: 321
<212> TYPE: DNA
<213> ORGANISM: Artificial Sequence

```
<220> FEATURE:
<223> OTHER INFORMATION: 445-3 VK DNA

<400> SEQUENCE: 29
gacatccaga tgacccagtc tcccagctcc ctgtccgcct ctgtgggcga tagggtgacc      60
atcacatgcc gggcctccca gggcatctcc aactacctga attggtatca gcagaagcca     120
gacggcgcca tcaagctgct gatctacgac gcctctacac tgtatagcgg cgtgccctcc     180
agattctctg gcagcggctc cggaaccgac ttcaccctga caatctctag cctgcagccc     240
gaggatttcg ccacatacta ttgtcagcag tacagcaagc tgccttatac ctttggcggc     300
ggcacaaagg tggagatcaa g                                               321

<210> SEQ ID NO 30
<211> LENGTH: 18
<212> TYPE: PRT
<213> ORGANISM: Homo sapiens

<400> SEQUENCE: 30

His Thr Leu Gln Pro Ala Ser Asn Ser Ser Asp Ala Ile Cys Glu Asp
1               5                   10                  15

Arg Asp

<210> SEQ ID NO 31
<211> LENGTH: 41
<212> TYPE: PRT
<213> ORGANISM: Homo sapiens

<400> SEQUENCE: 31

Pro Cys Pro Pro Gly His Phe Ser Pro Gly Asp Asn Gln Ala Cys Lys
1               5                   10                  15

Pro Trp Thr Asn Cys Thr Leu Ala Gly Lys His Thr Leu Gln Pro Ala
            20                  25                  30

Ser Asn Ser Ser Asp Ala Ile Cys Glu
        35                  40
```

ANTI-OX40 ANTIBODIES AND METHODS OF USE

CROSS-REFERENCE TO RELATED APPLICATIONS

This application is a U.S. National Stage Application under 35 U.S.C. § 371 of International Application No. PCT/CN2019/088013, filed May 22, 2019, which claims the benefit of priority to International patent application number PCT/CN2018/088101, filed on May 23, 2018, the disclosures of which are incorporated herein by reference in their entireties for all purposes.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: BEIG 038_01US_SeqList_ST25.txt, date recorded Nov. 13, 2020, file size 19 kilobytes).

FIELD OF THE INVENTION

Disclosed herein are antibodies or antigen-binding fragments thereof that bind to human OX40, a composition comprising said antibody, as well as methods of use for the treatment of cancer.

BACKGROUND

OX40 (also known as ACT35, CD134, or TNFRSF4) is an approximately 50 KD type I transmembrane glycoprotein, and a member of the tumor necrosis factor receptor super family (TNFRSF) (Croft, 2010; Gough and Weinberg, 2009). Mature human OX40 is composed of 249 amino acid (AA) residues, with a 37 AA cytoplasmic tail and a 185 AA extracellular region. The extracellular domain of OX40 contains three complete and one incomplete cysteine-rich domains (CRDs). The intracellular domain of OX40 contains one conserved signaling-related QEE motif, which mediates binding to several TNFR-associated factors (TRAF) including TRAF2, TRAF3, and TRAF5, allowing OX40 to link to intracellular kinases (Arch and Thompson, 1998; Willoughby et al., 2017).

OX40 was initially discovered on activated rat $CD4^+$ T cells, and murine and human homologs were subsequently cloned from T cells (al-Shamkhani et al., 1996; Calderhead et al., 1993). In addition to expression on activated $CD4^+$ T cells, including T helper (Th) 1 cells, Th2 cells, Th17 cells, as well as regulatory T (Treg) cells, OX40 expression has also been found on the surface of activated $CD8^+$ T cells, natural killer (NK) T cells, neutrophils, and NK cells (Croft, 2010). In contrast, low OX40 expression is found on naïve CD4+ and $CD8^+$ T cells, as well as on most resting memory T cells (Croft, 2010; Soroosh et al., 2007). The surface expression of OX40 on naïve T cells is transient. After TCR activation, OX40 expression on T cells is greatly increased within 24 hours and with peaks in 2~3 days, persisting for 5~6 days (Gramaglia et al., 1998).

The ligand for OX40 (OX40L, also known as gp34, CD252 or TNFSF4) is the sole ligand for OX40. Similar to other TNFSF (tumor necrosis factor superfamily) members, OX40L is a type II glycoprotein, which contains 183 AA with a 23 AA intracellular domain and a 133 AA extracellular domain (Croft, 2010; Gough and Weinberg, 2009). OX40L naturally forms a homomeric trimer complex on the cell surface. The ligand trimer interacts with three copies of OX40 at the ligand monomer-monomer interface mostly through CRD1, CRD2, and partial CRD3 regions of the receptor but without the involvement of CRD4 (Compaan and Hymowitz, 2006). OX40L is primarily expressed on activated antigen presenting cells (APC), including activated B cells (Stuber et al., 1995), mature conventional dendritic cells (DCs) (Ohshima et al., 1997), plasmacytoid DCs (pDCs) (Ito et al., 2004), macrophages (Weinberg et al., 1999), and Langerhans cells (Sato et al., 2002). In addition, OX40L has been found to be expressed on other cells types, such as NK cells, mast cells, subsets of activated T cells, as well as vascular endothelial cells and smooth muscle cells (Croft, 2010; Croft et al., 2009).

OX40 trimerization via ligation by trimeric OX40L or dimerization by agonistic antibodies contribute to the recruitment and docking of adaptor molecules TRAF2, TRAF3, and/or TRAF5 to its intracellular QEE motif (Arch and Thompson, 1998; Willoughby et al., 2017). The recruitment and docking of TRAF2 and TRAF3 can further lead to activation of both the canonical NF-κB1 and non-canonical NF-κB2 pathways, which play key roles in regulation of the survival, differentiation, expansion, cytokine production and effector functions of T cells (Croft, 2010; Gramaglia et al., 1998; Huddleston et al., 2006; Rogers et al., 2001; Ruby and Weinberg, 2009; Song et al., 2005a; Song et al., 2005b; Song et al., 2008).

In normal tissues, OX40 expression is low and is mainly on lymphocytes in lymphoid organs (Durkop et al., 1995). However, upregulation of OX40 expression on immune cells have frequently been observed in both animal models and human patients with pathological conditions (Redmond and Weinberg, 2007), such as autoimmune diseases (Carboni et al., 2003; Jacquemin et al., 2015; Szypowska et al., 2014) and cancers (Kjaergaard et al., 2000; Vetto et al., 1997; Weinberg et al., 2000). Notably, the increased expression of OX40 is associated with longer survival in patients with colorectal cancer and cutaneous melanoma, and inversely correlates with the occurrence of distant metastases and more advanced tumor features (Ladanyi et al., 2004; Petty et al., 2002; Sarff et al., 2008). It has also been shown that anti-OX40 antibody treatment could elicit anti-tumor efficacy in various mouse models (Aspeslagh et al., 2016), indicating the potential of OX40 as an immunotherapeutic target. In the first clinical trial in cancer patients, conducted by Curti et al., evidence of anti-tumor efficacy and activation of tumor-specific T cells was observed with an agonistic anti-OX40 monoclonal antibody, indicating that OX40 antibodies have utility in boosting anti-tumor T-cell responses (Curti et al., 2013).

The mechanism of action of agonistic anti-OX40 antibodies in mediating anti-tumor efficacy have been studied primarily in mouse tumor models (Weinberg et al., 2000). Until recently, the mechanism of action of agonistic anti-OX40 antibodies in tumors was attributed to their ability to trigger a co-stimulatory signaling pathway in effector T cells, as well as the inhibitory effects on the differentiation and functions of Treg cells (Aspeslagh et al., 2016; Ito et al., 2006; St Rose et al., 2013; Voo et al., 2013). Recent studies have shown that in both animal tumor models and cancer patients, tumor infiltrating Tregs express higher levels of OX40 than effector T cells (both $CD4^+$ and $CD8^+$) and peripheral Tregs (Lai et al., 2016; Marabelle et al., 2013b; Montler et al., 2016; Soroosh et al., 2007; Timperi et al., 2016). Therefore, the secondary effects by which anti-OX40 antibodies trigger anti-tumor responses rely on their Fc-mediated effector functions in depleting intra-tumoral OX40+ Treg cells via antibody-dependent cytotoxicity (ADCC) and/or antibody-dependent cellular phagocytosis (ADCP) (Aspeslagh et al., 2016; Bulliard et al., 2014; Marabelle et al., 2013a; Marabelle et al., 2013b; Smyth et al., 2014). This work demonstrates that agonistic anti-OX40 antibodies with Fc-mediated effector function could preferentially deplete intra-tumoral Tregs and improve the ratios of CD8+ effector T cells to Tregs in the tumor microenvironment (TME), resulting in improved anti-tumor immune responses, increased tumor regression and improved survival (Bulliard et al., 2014; Carboni et al., 2003; Jacquemin et al., 2015; Marabelle et al., 2013b). Based on these findings, there is an unmet medical need to develop agonistic anti-OX40 antibodies with both agonistic activities and Fc-mediated effector functions.

To date the agonistic anti-OX40 antibodies in the clinic are mostly ligand-competitive antibodies which block the OX40-OX40L interaction (e.g. WO2016196228A1). Since OX40-OX40L interaction is essential for enhancing effective anti-tumor immunity, blockade of OX40-OX40L restricts the efficacy of these ligand-competitive antibodies. Therefore, OX40 agonist antibodies that specifically bind to OX40 while not interfering with OX40 interacting with OX40L have utility in the treatment of cancer and autoimmune disorders.

SUMMARY OF THE INVENTION

The present disclosure is directed to agonistic anti-OX40 antibodies and antigen-binding fragments thereof that activate OX40 and induce signaling in immune cells, thus promoting anti-tumor immunity.

In one embodiment, the disclosure provides for monoclonal antibodies that bind to human OX40, or antigen-binding fragments thereof. In one aspect, the antibody of the present disclosure does not compete with OX40L, or interfere with the binding of OX40 to its ligand OX40L.

The present disclosure encompasses the following embodiments.

An antibody or antigen-binding fragment thereof, which specifically binds to human OX40 and comprises: (i) a heavy chain variable region that comprises (a) a HCDR (Heavy Chain Complementarity Determining Region) 1 of SEQ ID NO: 3, (b) a HCDR2 of SEQ ID NO:24, (c) a HCDR3 of SEQ ID NO:5 and a light chain variable region that comprises: (d) a LCDR (Light Chain Complementarity Determining Region) 1 of SEQ ID NO:25, (e) a LCDR2 of SEQ ID NO: 19, and (f) a LCDR3 of SEQ ID NO:8; (ii) a heavy chain variable region that comprises (a) a HCDR1 of SEQ ID NO:3, (b) a HCDR2 of SEQ ID NO:18, (c) a HCDR3 of SEQ ID NO:5; and a light chain variable region that comprises: (d) a LCDR1 of SEQ ID NO:6, (e) a LCDR2 of SEQ ID NO:19, and (f) a LCDR3 of SEQ ID NO: 8; (iii) a heavy chain variable region that comprises (a) a HCDR1 of SEQ ID NO:3, (b) a HCDR2 of SEQ ID NO:13, (c) a HCDR3 of SEQ ID NO:5; and a light chain variable region that comprises: (d) a LCDR1 of SEQ ID NO:6, (e) a LCDR2 of SEQ ID NO:7, and (f) a LCDR3 of SEQ ID NO:8; or (iv) a heavy chain variable region that comprises (a) a HCDR1 of SEQ ID NO:3, (b) a HCDR2 of SEQ ID NO:4, (c) a HCDR3 of SEQ ID NO:5; and a light chain variable region that comprises: (d) a LCDR1 of SEQ ID NO:6, (e) a LCDR2 of SEQ ID NO:7, and (f) a LCDR3 of SEQ ID NO:8.

The antibody or antigen-binding fragment of claim 1, comprises: (i) a heavy chain variable region (VH) comprising an amino acid sequence at least 90, 91, 92, 93, 94, 95, 96, 97, 98 or 99% identical to SEQ ID NO:26, and a light chain variable region (VL) comprising an amino acid sequence at least 90, 91, 92, 93, 94, 95, 96, 97, 98 or 99% identical to SEQ ID NO: 28; (ii) a heavy chain variable region (VH) comprising an amino acid sequence at least 90, 91, 92, 93, 94, 95, 96, 97, 98 or 99% identical to SEQ ID NO: 20, and a light chain variable region (VL) comprising an amino acid sequence at least 90, 91, 92, 93, 94, 95, 96, 97, 98 or 99% identical to SEQ ID NO: 22; (iii) a heavy chain variable region (VH) comprising an amino acid sequence at least 90, 91, 92, 93, 94, 95, 96, 97, 98 or 99% identical to SEQ ID NO: 14, and a light chain variable region (VL) comprising an amino acid sequence at least 90, 91, 92, 93, 94, 95, 96, 97, 98 or 99% identical to SEQ ID NO: 16; or (iv) a heavy chain variable region (VH) comprising an amino acid sequence at least 91, 92, 93, 94, 95, 96, 97, 98 or 99% identical to SEQ ID NO:9, and a light chain variable region (VL) comprising an amino acid sequence at least 91, 92, 93, 94, 95, 96, 97, 98 or 99% identical to SEQ ID NO:11.

The antibody or antigen-binding fragment, wherein one, two, three, four, five, six, seven, eight, nine, or ten amino acids within SEQ ID NO:26, 28, 20, 22, 14, 16, 9, and/or 11 have been inserted, deleted or substituted.

The antibody or antigen-binding fragment, that comprises: (i) a heavy chain variable region (VH) that comprises SEQ ID NO:26, and a light chain variable region (VL) that comprises SEQ ID NO: 28; (ii) a heavy chain variable region (VH) that comprises SEQ ID NO: 20, and a light chain variable region (VL) that comprises SEQ ID NO: 22; (iii) a heavy chain variable region (VH) that comprises SEQ ID NO: 14, and a light chain variable region (VL) that comprises SEQ ID NO: 16; or (iv) a heavy chain variable region (VH) that comprises SEQ ID NO:9, and a light chain variable region (VL) that comprises SEQ ID NO:11.

The antibody or antigen-binding fragment, which is a monoclonal antibody, a chimeric antibody, a humanized antibody, a human engineered antibody, a single chain antibody (scFv), a Fab fragment, a Fab' fragment, or a F(ab')$_2$ fragment.

The antibody or antigen-binding fragment, which has OX40 agonist activity.

The antibody or antigen-binding fragment, which binds to human OX40 at an epitope comprising one or more amino acid residues selected from the group consisting of H153 to D170 of human OX40.

The antibody or antigen-binding fragment, which binds to human OX40 at an epitope comprising one or more amino acid residues selected from the group consisting of H153, T154, I165, E167 and D170 of human OX40.

The antibody or antigen-binding fragment, which binds to human OX40 at an epitope comprising one or more amino acid residues selected from the group consisting of H153, I165 and E167 of human OX40. The antibody or antigen-binding fragment, which binds to human OX40 at an epitope comprising one amino acid residue selected from the group consisting of H153, I165 and E167 of human OX40.

The antibody or antigen-binding fragment, which binds to human OX40 at or within SEQ ID NO.30.

The antibody or antigen-binding fragment, which binds to human OX40 at an equilibrium dissociation constant ($K_D$) equal to or higher than 7.28 nM, 9.47 nM, 13.5 nM, or 17.1 nM as measured by surface plasmon resonance (SPR).

The antibody or antigen-binding fragment, wherein the antibody or antigen-binding fragment thereof has antibody dependent cellular cytotoxicity (ADCC) or complement dependent cytotoxicity (CDC).

The antibody or antigen-binding fragment, wherein the antibody or antigen-binding fragment thereof has reduced glycosylation or no glycosylation or is hypofucosylated.

The antibody or antigen-binding fragment, wherein the antibody or antigen-binding fragment thereof comprises increased bisecting GlcNac structures.

The antibody or antigen-binding fragment, wherein the Fc domain is of an IgG1.

The antibody or antigen-binding fragment, wherein the Fc domain is of an IgG4.

The antibody or antigen-binding fragment, wherein the IgG4 has an S228P substitution (according to EU numbering system).

The antibody or antigen-binding fragment, wherein the IgG4 has S228P and R409K substitutions (according to EU numbering system).

The antibody or antigen-binding fragment, which has one or more of the following properties:
  (i) capable of cross-reacting with cyno OX40;
  (ii) does not interfere with OX40-OX40L interaction;
  (iii) capable of stimulating a T-cell, particularly at an $EC_{50}$ equal to or higher than 0.06 ng/ml; (iv) capable of activating $CD4^+$ T-cells, particularly as measured in a mixed lymphocyte reaction (MLR) assay;
  (v) capable of mediating ADCC, particularly as measured in a lactate dehydrogenase (LDH) release-based ADCC assay;
  (vi) capable of depleting $CD4^+$ Tregs;
  (vii) capable of increasing the $CD8^+$ Teff/Treg ratio; or
  (viii) capable of mediating partial regression of tumor in an animal tumor model.

A pharmaceutical composition comprising the antibody or antigen-binding fragment thereof, further comprising a pharmaceutically acceptable carrier.

A method of treating cancer comprising administering to a patient in need an effective amount of the antibody or antigen-binding fragment.

The method wherein the cancer includes, but not limited to, breast cancer, head and neck cancer, gastric cancer, kidney cancer, liver cancer, small cell lung cancer, non-small cell lung cancer, ovarian cancer, skin cancer, mesothelioma, lymphoma, leukemia, myeloma, sarcoma and etc.

The method wherein the antibody or the pharmaceutical composition is administered in combination with another therapeutic agent.

The method wherein the therapeutic agent is paclitaxel or a paclitaxel agent, docetaxel, carboplatin, topotecan, cisplatin, irinotecan, doxorubicin, lenalidomide, 5-azacytidine The method wherein the therapeutic agent is a paclitaxel agent, lenalidomide or 5-azacytidine.

An isolated nucleic acid that encodes the antibody or antigen-binding fragment.

A vector comprising the nucleic acid.

A host cell comprising the nucleic acid.

A process for producing an antibody or antigen-binding fragment thereof comprising cultivating the host cell and recovering the antibody or antigen-binding fragment from the culture.

The antibody or antigen-binding fragment thereof, for use in the treatment or reducing the likelihood of: breast cancer, head and neck cancer, gastric cancer, kidney cancer, liver cancer, small cell lung cancer, non-small cell lung cancer, ovarian cancer, skin cancer, mesothelioma, lymphoma, leukemia, myeloma and sarcoma.

A diagnostic reagent comprising the antibody or antigen-binding fragment thereof which is labeled.

The diagnostic reagent wherein the label is selected from the group consisting of a radiolabel, a fluorophore, a chromophore, an imaging agent, and a metal ion.

In one embodiment, the antibody or an antigen-binding fragment thereof comprises one or more complementarity determining regions (CDRs) having an amino acid sequence selected from a group consisting of SEQ ID NO: 3, SEQ ID NO: 4, SEQ ID NO: 5, SEQ ID NO: 6, SEQ ID NO: 7, SEQ ID NO: 8, SEQ ID NO: 13, SEQ ID NO: 18, SEQ ID NO: 19, SEQ ID NO: 24 and SEQ ID NO: 25.

In another embodiment, the antibody or an antigen-binding fragment thereof comprises: (a) a heavy chain variable region comprising one or more complementarity determining regions (HCDRs) having an amino acid sequence selected from the group consisting of SEQ ID NO: 3, SEQ ID NO: 4, SEQ ID NO: 13, SEQ ID NO: 18, SEQ ID NO: 24 and SEQ ID NO: 5; and/or (b) a light chain variable region comprising one or more complementarity determining regions (LCDRs) having an amino acid sequence selected from the group consisting of SEQ ID NO: 6, SEQ ID NO: 25, SEQ ID NO: 7, SEQ ID NO: 19 and SEQ ID NO: 8.

In another embodiment, the antibody or an antigen-binding fragment thereof comprises: (a) a heavy chain variable region comprising three complementarity determining regions (HCDRs) which are HCDR1 having an amino acid sequence of SEQ ID NO: 3; HCDR2 having an amino acid sequence of SEQ ID NO: 4, SEQ ID NO: 13, SEQ ID NO: 18, or SEQ ID NO: 24; and HCDR3 having an amino acid sequence of SEQ ID NO: 5; and/or (b) a light chain variable region comprising three complementarity determining regions (LCDRs) which are LCDR1 having an amino acid sequence of SEQ ID NO: 6 or SEQ ID NO: 25; LCDR2 having an amino acid sequence of SEQ ID NO: 7 or SEQ ID NO: 19; and LCDR3 having an amino acid sequence of SEQ ID NO: 8.

In another embodiment, the antibody or an antigen-binding fragment thereof comprises: (a) a heavy chain variable region comprising three complementarity determining regions (HCDRs) which are HCDR1 having an amino acid sequence of SEQ ID NO: 3, HCDR2 having an amino acid sequence of SEQ ID NO: 4, and HCDR3 having an amino acid sequence of SEQ ID NO: 5; or HCDR1 having an amino acid sequence of SEQ ID NO: 3, HCDR2 having an amino acid sequence of SEQ ID NO: 13, and HCDR3 having an amino acid sequence of SEQ ID NO: 5; or HCDR1 having an amino acid sequence of SEQ ID NO: 3, HCDR2 having an amino acid sequence of SEQ ID NO: 18, and HCDR3 having an amino acid sequence of SEQ ID NO: 5; or HCDR1 having an amino acid sequence of SEQ ID NO: 3, HCDR2 having an amino acid sequence of SEQ ID NO: 24, and HCDR3 having an amino acid sequence of SEQ ID NO: 5; and/or (b) a light chain variable region comprising three complementarity determining regions (LCDRs) which are LCDR1 having an amino acid sequence of SEQ ID NO: 6, LCDR2 having an amino acid sequence of SEQ ID NO: 7, and LCDR3 having an amino acid sequence of SEQ ID NO: 8; or LCDR1 having an amino acid sequence of SEQ ID NO: 6, LCDR2 having an amino acid sequence of SEQ ID NO: 19, and LCDR3 having an amino acid sequence of SEQ ID NO: 8; or LCDR1 having an amino acid sequence of SEQ ID NO: 25, LCDR2 having an amino acid sequence of SEQ ID NO: 19, and LCDR3 having an amino acid sequence of SEQ ID NO: 8.

In another embodiment, the antibody or the antigen-binding fragment of the present disclosure comprises: a heavy chain variable region comprising HCDR1 having an amino acid sequence SEQ ID NO: 3, HCDR2 having an amino acid sequence of SEQ ID NO: 4, and HCDR3 having an amino acid sequence of SEQ ID NO: 5; and a light chain variable region comprising LCDR1 having an amino acid sequence of SEQ ID NO: 6, LCDR2 having an amino acid sequence of SEQ ID NO: 7, and LCDR3 having an amino acid sequence of SEQ ID NO: 8.

In one embodiment, the antibody or the antigen-binding fragment of the present disclosure comprises: a heavy chain variable region comprising HCDR1 having an amino acid sequence SEQ ID NO: 3, HCDR2 having an amino acid sequence of SEQ ID NO: 13, and HCDR3 having an amino acid sequence of SEQ ID NO: 5; and a light chain variable region comprising LCDR1 having an amino acid sequence of SEQ ID NO: 6, LCDR2 having an amino acid sequence of SEQ ID NO: 7, and LCDR3 having an amino acid sequence of SEQ ID NO: 8.

In another embodiment, the antibody or the antigen-binding fragment of the present disclosure comprises: a heavy chain variable region comprising HCDR1 having an amino acid sequence SEQ ID NO: 3, HCDR2 having an amino acid sequence of SEQ ID NO: 18, and HCDR3 having an amino acid sequence of SEQ ID NO: 5; and a light chain variable region comprising LCDR1 having an amino acid sequence of SEQ ID NO: 6, LCDR2 having an amino acid sequence of SEQ ID NO: 19, and LCDR3 having an amino acid sequence of SEQ ID NO: 8.

In another embodiment, the antibody or the antigen-binding fragment of the present disclosure comprises: a heavy chain variable region comprising HCDR1 having an amino acid sequence SEQ ID NO: 3, HCDR2 having an amino acid sequence of SEQ ID NO: 24, and HCDR3 having an amino acid sequence of SEQ ID NO: 5; and a light chain variable region comprising LCDR1 having an amino acid sequence of SEQ ID NO: 25, LCDR2 having an amino acid sequence of SEQ ID NO: 19, and LCDR3 having an amino acid sequence of SEQ ID NO: 8.

In one embodiment, the antibody of the present disclosure or an antigen-binding fragment thereof comprises: (a) a heavy chain variable region having an amino acid sequence of SEQ ID NO: 9, SEQ ID NO: 14, SEQ ID NO: 20 or SEQ ID NO: 26, or an amino acid sequence at least 95%, 96%, 97%, 98% or 99% identical to any one of SEQ ID NO: 9, SEQ ID NO: 14, SEQ ID NO: 20 or SEQ ID NO: 26; and/or (b) a light chain variable region having an amino acid sequence of SEQ ID NO: 11, SEQ ID NO: 16, SEQ ID NO: 22 or SEQ ID NO: 28, or an amino acid sequence at least 95%, 96%, 97%, 98% or 99% identical to any one of SEQ ID NO: 11, SEQ ID NO: 16, SEQ ID NO: 22 or SEQ ID NO: 28.

In another embodiment, the antibody of the present disclosure or an antigen-binding fragment thereof comprises: (a) a heavy chain variable region having an amino acid sequence of SEQ ID NO: 9, SEQ ID NO: 14, SEQ ID NO: 20 or SEQ ID NO: 26, or an amino acid sequence having one, two, or three amino acid substitutions in the amino acid sequence of SEQ ID NO: 9, SEQ ID NO: 14, SEQ ID NO: 20 or SEQ ID NO: 26; and/or (b) a light chain variable region having an amino acid sequence of SEQ ID NO: 11, SEQ ID NO: 16, SEQ ID NO: 22 or SEQ ID NO: 28, or an amino acid sequence having one, two, three, four, or five amino acid substitutions in the amino acid of SEQ ID NO: 11, SEQ ID NO: 16, SEQ ID NO: 22 or SEQ ID NO: 28. In another embodiment, the amino acid substitutions are conservative amino acid substitutions.

In one embodiment, the antibody of the present disclosure or an antigen-binding fragment thereof comprises:
(a) a heavy chain variable region having an amino acid sequence of SEQ ID NO: 9, and a light chain variable region having an amino acid sequence of SEQ ID NO: 11; or
(b) a heavy chain variable region having an amino acid sequence of SEQ ID NO: 14, and a light chain variable region having an amino acid sequence of SEQ ID NO: 16; or
(c) a heavy chain variable region having an amino acid sequence of SEQ ID NO: 20, and a light chain variable region having an amino acid sequence of SEQ ID NO: 22; or
(d) a heavy chain variable region having an amino acid sequence of SEQ ID NO: 26, and a light chain variable region having an amino acid sequence of SEQ ID NO: 28.

In one embodiment, the antibody of the present disclosure is of IgG1, IgG2, IgG3, or IgG4 isotype. In a more specific embodiment, the antibody of the present disclosure comprises Fc domain of wild-type human IgG1 (also referred as human IgG1wt or huIgG1) or IgG2. In another embodiment, the antibody of the present disclosure comprises Fc domain of human IgG4 with S228P and/or R409K substitutions (according to EU numbering system).

In one embodiment, the antibody of the present disclosure binds to OX40 with a binding affinity ($K_D$) of from $1 \times 10^{-6}$ M to $1 \times 10^{-10}$ M. In another embodiment, the antibody of the present disclosure binds to OX40 with a binding affinity ($K_D$) of about $1 \times 10^{-6}$ M, about $1 \times 10^{-7}$ M, about $1 \times 10^{-8}$ M, about $1 \times 10^{-9}$ M or about $1 \times 10^{-10}$ M.

In another embodiment, the anti-human OX40 antibody of the present invention shows a cross-species binding activity to cynomolgus OX40.

In one embodiment, the anti-OX40 antibody of the present disclosure binds to an epitope of human OX40 outside of the OX40-OX40L interaction interface. In another embodiment, the anti-OX40 antibody of the present disclosure does not compete with OX40 ligand binding to OX40. In yet another embodiment, the anti-OX40 antibody of the present disclosure does not block the interaction between OX40 and its ligand OX40L.

Antibodies of the current disclosure are agonistic and significantly enhance the immune response. The invention provides a method for testing the agonistic ability of anti-OX40 antibodies. In an embodiment, the antibody of the present disclosure can significantly stimulate primary T cell to produce IL-2 in a mixed lymphocyte reaction (MLR) assay.

In one embodiment, antibodies of the present disclosure have strong Fc-mediated effector functions. The antibodies mediate antibody-dependent cellular cytotoxicity (ADCC) against OX40$^{Hi}$ target cells such as regulatory T cells (Treg cells) by NK cells. In one aspect, the disclosure provides a method of evaluating the anti-OX40 antibody-mediated in vitro depletion of specific T-cell subsets based on different OX40 expression levels.

Antibodies or antigen-binding fragments of the present disclosure do not block the OX40-OX40L interaction. In addition, the OX40 antibodies exhibit dose-dependent anti-tumor activity in vivo, as shown in animal models. The dose-dependent activity is differentiated from the activity profile of anti-OX40 antibodies that block OX40-OX40L interaction.

The present disclosure relates to isolated nucleic acids comprising nucleotide sequences encoding the amino acid sequence of the antibody or an antigen-binding fragment. In one embodiment, the isolated nucleic acid comprises a VH nucleotide sequence of SEQ ID NO: 10, SEQ ID NO: 15, SEQ ID NO: 21, or SEQ ID NO: 27, or a nucleotide sequence having at least 95%, 96%, 97%, 98% or 99% identity to SEQ ID NO: 10, SEQ ID NO: 15, SEQ ID NO: 21, or SEQ ID NO: 27, and encodes the VH region of the antibody or an antigen-binding fragment of the present disclosure. Alternatively or additionally, the isolated nucleic acid comprises a VL nucleotide sequence of SEQ ID NO: 12, SEQ ID NO: 17, SEQ ID NO: 23, or SEQ ID NO: 29, or a nucleotide sequence having at least 95%, 96%, 97%, 98% or 99% identity to SEQ ID NO: 12, SEQ ID NO: 17, SEQ ID NO: 23, or SEQ ID NO: 29, and encodes the VL region the antibody or an antigen-binding fragment of the present disclosure.

In another aspect, the present disclosure relates to a pharmaceutical composition comprising the OX40 antibody or antigen-binding fragment thereof, and optionally a pharmaceutically acceptable excipient.

In yet another aspect, the present disclosure relates to a method of treating a disease in a subject, which comprises administering the OX40 antibody or antigen-binding fragment thereof, or an OX40 antibody pharmaceutical composition in a therapeutically effective amount to a subject in need thereof. In another embodiment the disease to be treated by the antibody or the antigen-binding fragment is cancer or an autoimmune disease.

The current disclosure relates to use of the antibody or the antigen-binding fragment thereof, or an OX40 antibody pharmaceutical composition for treating a disease, such as cancer or autoimmune diseases.

BRIEF DESCRIPTION OF THE DRAWINGS

FIG. 12A show the ratio of CD8+/Total T cells. FIG. 12B is the Treg/Total T cell ratio. FIG. 12C shows the CD8+/Treg ratio. Data is shown as mean±SD of duplicates. Statistical significances between 445-3 and 1A7.gr1 at indicated concentrations are shown. *: P<0.05; **: P<0.01.

FIG. 13A compares increasing doses of the 445-3 antibody with increasing doses of 1A7.gr1 antibody and the reduction of tumor growth. FIG. 13B presents data for all mice treated with that specific dose. Data is presented as mean tumor volume±standard error of the mean (SEM) with 6 mice per group. Statistical significance: *: P<0.05 vs isotype control.

FIG. 14A-14B is a table of amino acid alterations that were made in the OX40 antibodies.

DEFINITIONS

Figure 1:
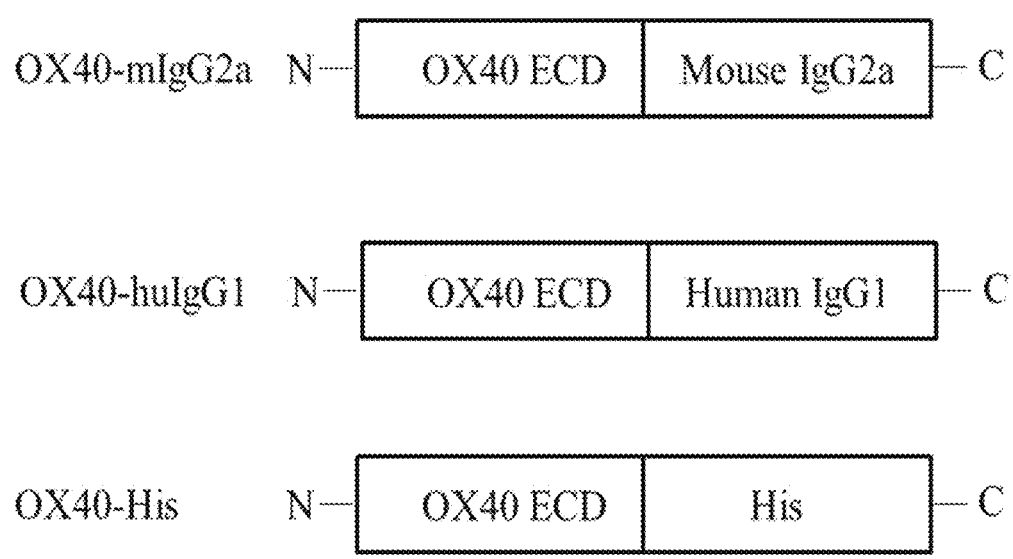
FIG. 1 is a schematic diagram of OX40-mIgG2a, OX40-huIgG1 and OX40-His constructs. OX40 ECD: OX40 extracellular domain. N: N-terminus. C: C-terminus.

Unless specifically defined elsewhere in this document, all other technical and scientific terms used herein have the meaning commonly understood by one of ordinary skill in the art.

As used herein, including the appended claims, the singular forms of words such as "a," "an," and "the," include their corresponding plural references unless the context clearly dictates otherwise.

The term "or" is used to mean, and is used interchangeably with, the term "and/or" unless the context clearly dictates otherwise.

The term "anti-cancer agent" as used herein refers to any agent that can be used to treat a cell proliferative disorder such as cancer, including but not limited to, cytotoxic agents, chemotherapeutic agents, radiotherapy and radiotherapeutic agents, targeted anti-cancer agents, and immunotherapeutic agents.

The term "OX40" refers to an approximately 50 KD type I transmembrane glycoprotein, a member of tumor necrosis factor receptor super family. OX40 is also known as ACT35, CD134, or TNFRSF4. The amino acid sequence of human OX40, (SEQ ID NO: 1) can also be found at accession number NP_003318 and the nucleotide sequence encoding the OX40 protein is accession number: X75962.1. The term "OX40 ligand" or "OX40L" refers to the sole ligand of OX40 and is interchangeable with gp34, CD252 or TNFSF4.

The terms "administration," "administering," "treating," and "treatment" herein, when applied to an animal, human, experimental subject, cell, tissue, organ, or biological fluid, means contact of an exogenous pharmaceutical, therapeutic, diagnostic agent, or composition to the animal, human, subject, cell, tissue, organ, or biological fluid. Treatment of a cell encompasses contact of a reagent to the cell, as well as contact of a reagent to a fluid, where the fluid is in contact with the cell. The term "administration" and "treatment" also means in vitro and ex vivo treatments, e.g., of a cell, by a reagent, diagnostic, binding compound, or by another cell. The term "subject" herein includes any organism, preferably an animal, more preferably a mammal (e.g., rat, mouse, dog, cat, rabbit) and most preferably a human. Treating any disease or disorder refer in one aspect, to ameliorating the disease or disorder (i.e., slowing or arresting or reducing the development of the disease or at least one of the clinical symptoms thereof). In another aspect, "treat," "treating," or "treatment" refers to alleviating or ameliorating at least one physical parameter including those which may not be discernible by the patient. In yet another aspect, "treat," "treating," or "treatment" refers to modulating the disease or disorder, either physically, (e.g., stabilization of a discernible symptom), physiologically, (e.g., stabilization of a physical parameter), or both. In yet another aspect, "treat," "treating," or "treatment" refers to preventing or delaying the onset or development or progression of the disease or disorder.

The term "subject" in the context of the present disclosure is a mammal, e.g., a primate, preferably a higher primate, e.g., a human (e.g., a patient having, or at risk of having, a disorder described herein).

The term "affinity" as used herein refers to the strength of interaction between antibody and antigen. Within the antigen, the variable region of the antibody "arm" interacts through non-covalent forces with the antigen at numerous sites; the more interactions, the stronger the affinity.

The term "antibody" as used herein refers to a polypeptide of the immunoglobulin family that can bind a corresponding antigen non-covalently, reversibly, and in a specific manner. For example, a naturally occurring IgG antibody is a tetramer comprising at least two heavy (H) chains and two light (L) chains inter-connected by disulfide bonds. Each heavy chain is comprised of a heavy chain variable region (abbreviated herein as VH) and a heavy chain constant region. The heavy chain constant region is comprised of three domains, CH1, CH2 and CH3. Each light chain is comprised of a light chain variable region (abbreviated herein as VL) and a light chain constant region. The light chain constant region is comprised of one domain, CL. The VH and VL regions can be further subdivided into regions of hypervariability, termed complementarity determining regions (CDRs), interspersed with regions that are more conserved, termed framework regions (FR). Each VH and VL is composed of three CDRs and four FRs arranged from amino-terminus to carboxyl-terminus in the following order: FR1, CDR1, FR2, CDR2, FR3, CDR3, and FR4. The variable regions of the heavy and light chains contain a binding domain that interacts with an antigen. The constant regions of the antibodies can mediate the binding of the immunoglobulin to host tissues or factors, including various cells of the immune system (e.g., effector cells) and the first component (C1q) of the classical complement system.

The term "antibody" includes, but is not limited to, monoclonal antibodies, human antibodies, humanized antibodies, chimeric antibodies, and anti-idiotypic (anti-Id) antibodies. The antibodies can be of any isotype/class (e.g., IgG, IgE, IgM, IgD, IgA and IgY), or subclass (e.g., IgG1, IgG2, IgG3, IgG4, IgA1 and IgA2).

In some embodiments, the anti-OX40 antibodies comprise at least one antigen-binding site, or at least a variable region. In some embodiments, the anti-OX40 antibodies comprise an antigen-binding fragment from an OX40 antibody described herein. In some embodiments, the anti-OX40 antibody is isolated or recombinant.

The term "monoclonal antibody" or "mAb" or "Mab" herein means a population of substantially homogeneous antibodies, i.e., the antibody molecules comprised in the population are identical in amino acid sequence except for possible naturally occurring mutations that can be present in minor amounts. In contrast, conventional (polyclonal) antibody preparations typically include a multitude of different antibodies having different amino acid sequences in their variable domains, particularly their complementarity determining regions (CDRs), which are often specific for different epitopes. The modifier "monoclonal" indicates the character of the antibody as being obtained from a substantially homogeneous population of antibodies and is not to be construed as requiring production of the antibody by any particular method. Monoclonal antibodies (mAbs) can be obtained by methods known to those skilled in the art. See, for example Kohler et al., Nature 1975 256:495-497; U.S. Pat. No. 4,376,110; Ausubel et al., CURRENT PROTOCOLS IN MOLECULAR BIOLOGY 1992; Harlow et al., ANTIBODIES: A LABORATORY MANUAL, Cold spring Harbor Laboratory 1988; and Colligan et al., CURRENT PROTOCOLS IN IMMUNOLOGY 1993. The antibodies disclosed herein can be of any immunoglobulin class including IgG, IgM, IgD, IgE, IgA, and any subclass thereof such as IgG1, IgG2, IgG3, IgG4. A hybridoma producing a monoclonal antibody can be cultivated in vitro or in vivo. High titers of monoclonal antibodies can be obtained in in vivo production where cells from the individual hybridomas are injected intraperitoneally into mice, such as pristine-primed Balb/c mice to produce ascites fluid containing high concentrations of the desired antibodies. Monoclonal antibodies of isotype IgM or IgG can be purified from such ascites fluids, or from culture supernatants, using column chromatography methods well known to those of skill in the art.

In general, the basic antibody structural unit comprises a tetramer. Each tetramer includes two identical pairs of polypeptide chains, each pair having one "light chain" (about 25 kDa) and one "heavy chain" (about 50-70 kDa). The amino-terminal portion of each chain includes a variable region of about 100 to 110 or more amino acids primarily responsible for antigen recognition. The carboxy-terminal portion of the heavy chain can define a constant region primarily responsible for effector function. Typically, human light chains are classified as kappa and lambda light chains. Furthermore, human heavy chains are typically classified as α, δ, ε, γ, or μ, and define the antibody's isotypes as IgA, IgD, IgE, IgG, and IgM, respectively. Within light and heavy chains, the variable and constant regions are joined by a "J" region of about 12 or more amino acids, with the heavy chain also including a "D" region of about 10 more amino acids.

The variable regions of each light/heavy chain (VL/VH) pair form the antibody binding site. Thus, in general, an intact antibody has two binding sites. Except in bifunctional or bispecific antibodies, the two binding sites are, in general, the same.

Typically, the variable domains of both the heavy and light chains comprise three hypervariable regions, also called "complementarity determining regions (CDRs)," which are located between relatively conserved framework regions (FR). The CDRs are usually aligned by the framework regions, enabling binding to a specific epitope. In general, from N-terminal to C-terminal, both light and heavy chain variable domains comprise FR-1 (or FR1), CDR-1 (or CDR1), FR-2 (FR2), CDR-2 (CDR2), FR-3 (or FR3), CDR-3 (CDR3), and FR-4 (or FR4). The positions of the CDRs and framework regions can be determined using various well known definitions in the art, e.g., Kabat, Chothia, and AbM (see, e.g., Johnson et al., Nucleic Acids Res., 29:205-206 (2001); Chothia and Lesk, J. Mol. Biol., 196:901-917 (1987); Chothia et al., Nature, 342:877-883 (1989); Chothia et al., J. Mol. Biol., 227:799-817 (1992); Al-Lazikani et al., J. Mol. Biol., 273:927-748 (1997)). Definitions of antigen combining sites are also described in the following: Ruiz et al., Nucleic Acids Res., 28:219-221 (2000); and Lefranc, M. P., Nucleic Acids Res., 29:207-209 (2001); MacCallum et al., J. Mol. Biol., 262:732-745 (1996); and Martin et al., Proc. Natl. Acad. Sci. USA, 86:9268-9272 (1989); Martin et al., Methods Enzymol., 203:121-153 (1991); and Rees et al., In Sternberg M. J. E. (ed.), Protein Structure Prediction, Oxford University Press, Oxford, 141-172 (1996). In a combined Kabat and Chothia numbering scheme, in some embodiments, the CDRs correspond to the amino acid residues that are part of a Kabat CDR, a Chothia CDR, or both. For example, the CDRs correspond to amino acid residues 26-35 (HC CDR1), 50-65 (HC CDR2), and 95-102 (HC CDR3) in a VH, e.g., a mammalian VH, e.g., a human VH; and amino acid residues 24-34 (LC CDR1), 50-56 (LC CDR2), and 89-97 (LC CDR3) in a VL, e.g., a mammalian VL, e.g., a human VL.

The term "hypervariable region" means the amino acid residues of an antibody that are responsible for antigen-binding. The hypervariable region comprises amino acid residues from a "CDR" (i.e., VL-CDR1, VL-CDR2 and VL-CDR3 in the light chain variable domain and VH-CDR1, VH-CDR2 and VH-CDR3 in the heavy chain variable domain). See, Kabat et al. (1991) Sequences of Proteins of Immunological Interest, 5th Ed. Public Health Service, National Institutes of Health, Bethesda, Md. (defining the CDR regions of an antibody by sequence); see also Chothia and Lesk (1987) J. Mol. Biol. 196: 901-917 (defining the CDR regions of an antibody by structure). The term "framework" or "FR" residues means those variable domain residues other than the hypervariable region residues defined herein as CDR residues.

Unless otherwise indicated, an "antigen-binding fragment" means antigen-binding fragments of antibodies, i.e. antibody fragments that retain the ability to bind specifically to the antigen bound by the full-length antibody, e.g. fragments that retain one or more CDR regions. Examples of antigen-binding fragments include, but not limited to, Fab, Fab', F(ab')2, and Fv fragments; diabodies; linear antibodies; single-chain antibody molecules, e.g., single chain Fv (ScFv); nanobodies and multispecific antibodies formed from antibody fragments.

An antibody "specifically binds" to a target protein, meaning the antibody exhibits preferential binding to that target as compared to other proteins, but this specificity does not require absolute binding specificity. An antibody is considered "specific" for its intended target if its binding is determinative of the presence of the target protein in a sample, e.g. without producing undesired results such as false positives. Antibodies or antigen-binding fragments thereof, useful in the current disclosure will bind to the target protein with an affinity that is at least two fold greater, preferably at least 10-times greater, more preferably at least 20-times greater, and most preferably at least 100-times greater than the affinity with non-target proteins. An antibody herein is said to bind specifically to a polypeptide comprising a given amino acid sequence, e.g. the amino acid sequence of a human OX40 molecule, if it binds to polypeptides comprising that sequence but does not bind to proteins lacking that sequence.

The term "human antibody" herein means an antibody that comprises human immunoglobulin protein sequences only. A human antibody can contain murine carbohydrate chains if produced in a mouse, in a mouse cell, or in a hybridoma derived from a mouse cell. Similarly, "mouse antibody" or "rat antibody" mean an antibody that comprises only mouse or rat immunoglobulin protein sequences, respectively.

The term "humanized antibody" means forms of antibodies that contain sequences from non-human (e.g., murine) antibodies as well as human antibodies. Such antibodies contain minimal sequence derived from non-human immunoglobulin. In general, the humanized antibody will comprise substantially all of at least one, and typically two, variable domains, in which all or substantially all of the hypervariable loops correspond to those of a non-human immunoglobulin and all or substantially all of the FR regions are those of a human immunoglobulin sequence. The humanized antibody optionally also will comprise at least a portion of an immunoglobulin constant region (Fc), typically that of a human immunoglobulin. The prefix "hum," "hu," "Hu," or "h" is added to antibody clone designations when necessary to distinguish humanized antibodies from parental rodent antibodies. The humanized forms of rodent antibodies will generally comprise the same CDR sequences of the parental rodent antibodies, although certain amino acid substitutions can be included to increase affinity, increase stability of the humanized antibody, remove a post-translational modification or for other reasons.

The term "corresponding human germline sequence" refers to the nucleic acid sequence encoding a human variable region amino acid sequence or subsequence that shares the highest determined amino acid sequence identity with a reference variable region amino acid sequence or subsequence in comparison to all other known variable region amino acid sequences encoded by human germline immunoglobulin variable region sequences. The corresponding human germline sequence can also refer to the human variable region amino acid sequence or subsequence with the highest amino acid sequence identity with a reference variable region amino acid sequence or subsequence in comparison to all other evaluated variable region amino acid sequences. The corresponding human germline sequence can be framework regions only, complementarity determining regions only, framework and complementary determining regions, a variable segment (as defined above), or other combinations of sequences or subsequences that comprise a variable region. Sequence identity can be determined using the methods described herein, for example, aligning two sequences using BLAST, ALIGN, or another alignment algorithm known in the art. The corresponding human germline nucleic acid or amino acid sequence can have at least about 90%, 91, 92%, 93%, 94%, 95%, 96%, 97%, 98%, 99%, or 100% sequence identity with the reference variable region nucleic acid or amino acid sequence.

The term "equilibrium dissociation constant ($K_D$, M)" refers to the dissociation rate constant (kd, time$^{-1}$) divided by the association rate constant (ka, time$^{-1}$, M$^{-1}$). Equilibrium dissociation constants can be measured using any known method in the art. The antibodies of the present disclosure generally will have an equilibrium dissociation constant of less than about 10$^{-7}$ or 10$^{-8}$ M, for example, less than about 10$^{-9}$ M or 10$^{-10}$ M, in some aspects, less than about 10$^{-11}$ M, 10$^{-12}$ M or 10$^{-13}$ M.

The terms "cancer" or "tumor" herein has the broadest meaning as understood in the art and refers to the physiological condition in mammals that is typically characterized by unregulated cell growth. In the context of the present disclosure, the cancer is not limited to certain type or location.

The term "combination therapy" refers to the administration of two or more therapeutic agents to treat a therapeutic condition or disorder described in the present disclosure. Such administration encompasses co-administration of these therapeutic agents in a substantially simultaneous manner. Such administration also encompasses co-administration in multiple, or in separate containers (e.g., capsules, powders, and liquids) for each active ingredient. Powders and/or liquids can be reconstituted or diluted to a desired dose prior to administration. In addition, such administration also encompasses use of each type of therapeutic agent in a sequential manner, either at approximately the same time or at different times. In either case, the treatment regimen will provide beneficial effects of the drug combination in treating the conditions or disorders described herein.

In the context of the present disclosure, when reference is made to an amino acid sequence, the term "conservative substitution" means substitution of the original amino acid by anew amino acid that does not substantially alter the chemical, physical and/or functional properties of the antibody or fragment, e.g. its binding affinity to OX40. Specifically, common conservative substations of amino acids are shown in following table and are well known in the art.

| Exemplary Conservative Amino Acid Substitutions | | |
|---|---|---|
| Original amino acid residue | One-letter and three-letter codes | Conservative substitution |
| Alanine | A or Ala | Gly; Ser |
| Arginine | R or Arg | Lys; His |
| Asparagine | N or Asn | Gln; His |
| Aspartic acid | D or Asp | Gln; Asn |
| Cysteine | C or Cys | Ser; Ala |
| Glutamine | Q or Gln | Asn |
| Glutamic acid | E or Glu | Asp; Gln |
| Glycine | G or Gly | Ala |
| Histidine | H or His | Asn; Gln |
| Isoleucine | I or Ile | Leu; Val |
| Leucine | L or Leu | Ile; val |
| Lysine | K or Lys | Arg; His |
| Methionine | M or Met | Leu; Ile; Tyr |
| Phenylalanine | F or Phe | Tyr; Met; Leu |
| Proline | P or Pro | Ala |
| Serine | S or Ser | Thr |
| Threonine | T or Thr | Ser |
| Tryptophan | W or Trp | Tyr; Phe |
| Tyrosine | Y or Tyr | Trp; Phe |
| Valine | V or Val | Ile; Leu |

Examples of algorithms that are suitable for determining percent sequence identity and sequence similarity are the BLAST algorithms, which are described in Altschul et al, Nuc. Acids Res. 25:3389-3402, 1977; and Altschul et al., J. Mol. Biol. 215:403-410, 1990, respectively. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold. These initial neighborhood word hits act as values for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word length (W) of 11, an expectation (E) or 10, M=5, N=-4 and a comparison of both strands. For amino acid sequences, the BLAST program uses as defaults a word length of 3, and expectation (E) of 10, and the BLOSUM62 scoring matrix (see Henikoff and Henikoff, (1989) Proc. Natl. Acad. Sci. USA 89: 10915) alignments (B) of 50, expectation (E) of 10, M=5, N=-4, and a comparison of both strands.

The BLAST algorithm also performs a statistical analysis of the similarity between two sequences (see, e.g., Karlin and Altschul, Proc. Natl. Acad. Sci. USA 90:5873-5787, 1993). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

The percent identity between two amino acid sequences can also be determined using the algorithm of E. Meyers and W. Miller, Comput. Appl. Biosci. 4: 11-17, (1988), which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch, J. Mol. Biol. 48:444-453, (1970), algorithm which has been incorporated into the GAP program in the GCG software package using either a BLOSUM62 matrix or a PAM250 matrix, and a gap weight of 16, 14, 12, 10, 8, 6, or 4 and a length weight of 1, 2, 3, 4, 5, or 6.

The term "nucleic acid" is used herein interchangeably with the term "polynucleotide" and refers to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

The term "operably linked" in the context of nucleic acids refers to a functional relationship between two or more polynucleotide (e.g., DNA) segments. Typically, it refers to the functional relationship of a transcriptional regulatory sequence to a transcribed sequence. For example, a promoter or enhancer sequence is operably linked to a coding sequence if it stimulates or modulates the transcription of the coding sequence in an appropriate host cell or other expression system. Generally, promoter transcriptional regulatory sequences that are operably linked to a transcribed sequence are physically contiguous to the transcribed sequence, i.e., they are cis-acting. However, some transcriptional regulatory sequences, such as enhancers, need not be physically contiguous or located in close proximity to the coding sequences whose transcription they enhance.

In some aspects, the present disclosure provides compositions, e.g., pharmaceutically acceptable compositions, which include an anti-OX40 antibody described herein, formulated together with at least one pharmaceutically acceptable excipient. As used herein, the term "pharmaceutically acceptable excipient" includes any and all solvents, dispersion media, isotonic and absorption delaying agents, and the like that are physiologically compatible. The excipient can be suitable for intravenous, intramuscular, subcutaneous, parenteral, rectal, spinal or epidermal administration (e.g. by injection or infusion).

The compositions disclosed herein can be in a variety of forms. These include, for example, liquid, semi-solid and solid dosage forms, such as liquid solutions (e.g., injectable and infusion solutions), dispersions or suspensions, liposomes, and suppositories. A suitable form depends on the intended mode of administration and therapeutic application. Typical suitable compositions are in the form of injectable or infusion solutions. One suitable mode of administration is parenteral (e.g., intravenous, subcutaneous, intraperitoneal, intramuscular). In some embodiments, the antibody is administered by intravenous infusion or injection. In certain embodiments, the antibody is administered by intramuscular or subcutaneous injection.

The term "therapeutically effective amount" as herein used, refers to the amount of an antibody that, when administered to a subject for treating a disease, or at least one of the clinical symptoms of a disease or disorder, is sufficient to effect such treatment for the disease, disorder, or symptom. The "therapeutically effective amount" can vary with the antibody, the disease, disorder, and/or symptoms of the disease or disorder, severity of the disease, disorder, and/or symptoms of the disease or disorder, the age of the subject to be treated, and/or the weight of the subject to be treated. An appropriate amount in any given instance can be apparent to those skilled in the art or can be determined by routine experiments. In the case of combination therapy, the "therapeutically effective amount" refers to the total amount of the combination objects for the effective treatment of a disease, a disorder or a condition.

DETAILED DESCRIPTION

The present disclosure provides for antibodies, antigen-binding fragments, that specifically bind human OX40. Furthermore, the present disclosure provides antibodies that have desirable pharmacokinetic characteristics and other desirable attributes, and thus can be used for reducing the likelihood of or treating cancer. The present disclosure further provides pharmaceutical compositions comprising the antibodies and methods of making and using such pharmaceutical compositions for the prevention and treatment of cancer and associated disorders.

Anti-OX40 Antibodies

The present disclosure provides for antibodies or antigen-binding fragments thereof that specifically bind to OX40. Antibodies or antigen-binding fragments of the present disclosure include, but are not limited to, the antibodies or antigen-binding fragments thereof, generated as described, below.

The present disclosure provides antibodies or antigen-binding fragments that specifically bind to OX40, wherein said antibodies or antibody fragments (e.g., antigen-binding fragments) comprise a VH domain having an amino acid sequence of SEQ ID NO:14, 20 or 26 (Table 3). The present disclosure also provides antibodies or antigen-binding fragments that specifically bind OX40, wherein said antibodies or antigen-binding fragments comprise a VH CDR having an amino acid sequence of any one of the VH CDRs listed in Table 3. In one aspect, the present disclosure provides antibodies or antigen-binding fragments that specifically bind to OX40, wherein said antibodies comprise (or alternatively, consist of) one, two, three, or more VH CDRs having an amino acid sequence of any of the VH CDRs listed in Table 3.

The present disclosure provides for antibodies or antigen-binding fragments that specifically bind to OX40, wherein said antibodies or antigen-binding fragments comprise a VL domain having an amino acid sequence of SEQ ID NO:16, 22 or 28 (Table 3). The present disclosure also provides antibodies or antigen-binding fragments that specifically bind to OX40, wherein said antibodies or antigen-binding fragments comprise a VL CDR having an amino acid sequence of any one of the VL CDRs listed in Table 3. In particular, the disclosure provides for antibodies or antigen-binding fragments that specifically bind to OX40, said antibodies or antigen-binding fragments comprise (or alternatively, consist of) one, two, three or more VL CDRs having an amino acid sequence of any of the VL CDRs listed in Table 3.

Other antibodies or antigen-binding fragments thereof of the present disclosure include amino acids that have been mutated, yet have at least 60%, 70%, 80%, 90%, 95% or 99% percent identity in the CDR regions with the CDR regions depicted in the sequences described in Table 3. In some aspects, it includes mutant amino acid sequences wherein no more than 1, 2, 3, 4 or 5 amino acids have been mutated in the CDR regions when compared with the CDR regions depicted in the sequence described in Table 3.

Other antibodies of the present disclosure include those where the amino acids or nucleic acids encoding the amino acids have been mutated; yet have at least 60%, 70%, 80%, 90%, 95% or 99% percent identity to the sequences described in Table 3. In some aspects, it includes mutant amino acid sequences wherein no more than 1, 2, 3, 4 or 5 amino acids have been mutated in the variable regions when compared with the variable regions depicted in the sequence described in Table 3, while retaining substantially the same therapeutic activity.

The present disclosure also provides nucleic acid sequences that encode VH, VL, the full length heavy chain, and the full length light chain of the antibodies that specifically bind to OX40. Such nucleic acid sequences can be optimized for expression in mammalian cells.

Identification of Epitopes and Antibodies that Bind to the Same Epitope

The present disclosure provides antibodies and antigen-binding fragments thereof that bind to an epitope of human OX40. In certain aspects the antibodies and antigen-binding fragments can bind to the same epitope of OX40.

The present disclosure also provides for antibodies and antigen-binding fragments thereof that bind to the same epitope as do the anti-OX40 antibodies described in Table 3. Additional antibodies and antigen-binding fragments thereof can therefore be identified based on their ability to cross-compete (e.g., to competitively inhibit the binding of, in a statistically significant manner) with other antibodies in binding assays. The ability of a test antibody to inhibit the binding of antibodies and antigen-binding fragments thereof of the present disclosure to OX40 demonstrates that the test antibody can compete with that antibody or antigen-binding fragments thereof for binding to OX40. Such an antibody can, without being bound to any one theory, bind to the same or a related (e.g., a structurally similar or spatially proximal) epitope on OX40 as the antibody or antigen-binding fragments thereof with which it competes. In a certain aspect, the antibody that binds to the same epitope on OX40 as the antibodies or antigen-binding fragments thereof of the present disclosure is a human or humanized monoclonal antibody. Such human or humanized monoclonal antibodies can be prepared and isolated as described herein.

Further Alteration of the Framework of Fc Region

In yet other aspects, the Fc region is altered by replacing at least one amino acid residue with a different amino acid residue to alter the effector functions of the antibody. For example, one or more amino acids can be replaced with a different amino acid residue such that the antibody has an altered affinity for an effector ligand but retains the antigen-binding ability of the parent antibody. The effector ligand to which affinity is altered can be, for example, an Fc receptor or the C1 component of complement. This approach is described in, e.g., U.S. Pat. Nos. 5,624,821 and 5,648,260, both by Winter et al.

In another aspect, one or more amino acid residues can be replaced with one or more different amino acid residues such that the antibody has altered C1q binding and/or reduced or abolished complement dependent cytotoxicity (CDC). This approach is described in, e.g., U.S. Pat. No. 6,194,551 by Idusogie et al.

In yet another aspect, one or more amino acid residues are altered to thereby alter the ability of the antibody to fix complement. This approach is described in, e.g., the PCT Publication WO 94/29351 by Bodmer et al. In a specific aspect, one or more amino acids of an antibody or antigen-binding fragment thereof of the present disclosure are replaced by one or more allotypic amino acid residues, for the IgG1 subclass and the kappa isotype. Allotypic amino acid residues also include, but are not limited to, the constant region of the heavy chain of the IgG1, IgG2, and IgG3 subclasses as well as the constant region of the light chain of the kappa isotype as described by Jefferis et al., MAbs. 1:332-338 (2009).

In another aspect, the Fc region is modified to increase the ability of the antibody to mediate antibody dependent cellular cytotoxicity (ADCC) and/or to increase the affinity of the antibody for an Fcγ receptor by modifying one or more amino acids. This approach is described in, e.g., the PCT Publication WO 00/42072 by Presta. Moreover, the binding sites on human IgG1 for FcγRI, FcγRII, FcγRIII and FcRn have been mapped and variants with improved binding have been described (see Shields et al., J. Biol. Chem. 276:6591-6604, 2001).

In still another aspect, the glycosylation of an antibody is modified. For example, an aglycosylated antibody can be made (i.e., the antibody lacks or has reduced glycosylation). Glycosylation can be altered to, for example, increase the affinity of the antibody for "antigen." Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation can increase the affinity of the antibody for antigen. Such an approach is described in, e.g., U.S. Pat. Nos. 5,714,350 and 6,350,861 by Co et al.

Additionally, or alternatively, an antibody can be made that has an altered type of glycosylation, such as a hypofucosylated antibody having reduced amounts of fucosyl residues or an antibody having increased bisecting GlcNac structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies to thereby produce an antibody with altered glycosylation. For example, EP 1,176,195 by Hang et al. describes a cell line with a functionally disrupted FUT8 gene, which encodes a fucosyl transferase, such that antibodies expressed in such a cell line exhibit hypofucosylation. PCT Publication WO 03/035835 by Presta describes a variant CHO cell line, Lec13 cells, with reduced ability to attach fucose to Asn (297)-linked carbohydrates, also resulting in hypofucosylation of antibodies expressed in that host cell (see also Shields et al., (2002) J. Biol. Chem. 277:26733-26740). PCT Publication WO 99/54342 by Umana et al., describes cell lines engineered to express glycoprotein-modifying glycosyl transferases (e.g., beta(1,4)-N acetylglucosaminyltransferase III (GnTIII)) such that antibodies expressed in the engineered cell lines exhibit increased bisecting GlcNac structures which results in increased ADCC activity of the antibodies (see also Umana et al., Nat. Biotech. 17:176-180, 1999).

In another aspect, if a reduction of ADCC is desired, human antibody subclass IgG4 was shown in many previous reports to have only modest ADCC and almost no CDC effector function (Moore G L, et al. 2010 MAbs, 2:181-189). On the other hand, natural IgG4 was found less stable in stress conditions such as in acidic buffer or under increasing temperature (Angal, S. 1993 Mol Immunol, 30:105-108; Dall'Acqua, W. et al, 1998 Biochemistry, 37:9266-9273; Aalberse et al. 2002 Immunol, 105:9-19). Reduced ADCC can be achieved by operably linking the antibody to IgG4 engineered with combinations of alterations to have reduced or null FcγR binding or C1q binding activities, thereby reducing or eliminating ADCC and CDC effector functions. Considering physicochemical properties of antibody as a biological drug, one of the less desirable, intrinsic properties of IgG4 is dynamic separation of its two heavy chains in solution to form half antibody, which lead to bi-specific antibodies generated in vivo via a process called "Fab arm exchange" (Van der Neut Kolfschoten M, et al. 2007 Science, 317:1554-157). The mutation of serine to proline at position 228 (EU numbering system) appeared inhibitory to the IgG4 heavy chain separation (Angal, S. 1993 Mol Immunol, 30:105-108; Aalberse et al. 2002 Immunol, 105: 9-19). Some of the amino acid residues in the hinge and γFc region were reported to have impact on antibody interaction with Fcγ receptors (Chappel S M, et al. 1991 Proc. Natl. Acad. Sci. USA, 88:9036-9040; Mukherjee, J. et al., 1995 FASEB J, 9:115-119; Armour, K. L. et al. 1999 Eur J Immunol, 29:2613-2624; Clynes, R. A. et al, 2000 Nature Medicine, 6:443-446; Arnold J. N., 2007 Annu Rev immunol, 25:21-50). Furthermore, some rarely occurring IgG4 isoforms in human population can also elicit different physicochemical properties (Brusco, A. et al. 1998 Eur J Immunogenet, 25:349-55; Aalberse et al. 2002 Immunol, 105:9-19). To generate OX40 antibodies with low ADCC, CDC and instability, it is possible to modify the hinge and Fc region of human IgG4 and introduce a number of alterations. These modified IgG4 Fc molecules can be found in SEQ ID NOs: 83-88, U.S. Pat. No. 8,735,553 to Li et al.

OX40 Antibody Production

Anti-OX40 antibodies and antigen-binding fragments thereof can be produced by any means known in the art, including but not limited to, recombinant expression, chemical synthesis, and enzymatic digestion of antibody tetramers, whereas full-length monoclonal antibodies can be obtained by, e.g., hybridoma or recombinant production. Recombinant expression can be from any appropriate host cells known in the art, for example, mammalian host cells, bacterial host cells, yeast host cells, insect host cells, etc.

The disclosure further provides polynucleotides encoding the antibodies described herein, e.g., polynucleotides encoding heavy or light chain variable regions or segments comprising the complementarity determining regions as described herein. In some aspects, the polynucleotide encoding the heavy chain variable regions has at least 85%, 89%, 90%, 91%, 92%, 93%, 94%, 95%, 96%, 97%, 98%, 99%, or 100% nucleic acid sequence identity with a polynucleotide selected from the group consisting of SEQ ID NOs: 15, 21 or 27. In some aspects, the polynucleotide encoding the light chain variable regions has at least 85%, 89%, 90%, 91%, 92%, 93%, 94%, 95%, 96%, 97%, 98%, 99%, or 100% nucleic acid sequence identity with a polynucleotide selected from the group consisting of SEQ ID NOs:17, 23, or 29.

The polynucleotides of the present disclosure can encode the variable region sequence of an anti-OX40 antibody. They can also encode both a variable region and a constant region of the antibody. Some of the polynucleotide sequences encode a polypeptide that comprises variable regions of both the heavy chain and the light chain of one of the exemplified anti-OX40 antibodies. Some other polynucleotides encode two polypeptide segments that respectively are substantially identical to the variable regions of the heavy chain and the light chain of one of the murine antibodies.

Also provided in the present disclosure are expression vectors and host cells for producing the anti-OX40 antibodies. The choice of expression vector depends on the intended host cells in which the vector is to be expressed. Typically, the expression vectors contain a promoter and other regulatory sequences (e.g., enhancers) that are operably linked to the polynucleotides encoding an anti-OX40 antibody chain or antigen-binding fragment. In some aspects, an inducible promoter is employed to prevent expression of inserted sequences except under the control of inducing conditions. Inducible promoters include, e.g., arabinose, lacZ, metallothionein promoter or a heat shock promoter. Cultures of transformed organisms can be expanded under non-inducing conditions without biasing the population for coding sequences whose expression products are better tolerated by the host cells. In addition to promoters, other regulatory elements can also be required or desired for efficient expression of an anti-OX40 antibody or antigen-binding fragment. These elements typically include an ATG initiation codon and adjacent ribosome binding site or other sequences. In addition, the efficiency of expression can be enhanced by the inclusion of enhancers appropriate to the cell system in use (see, e.g., Scharf et al., Results Probl. Cell Differ. 20:125, 1994; and Bittner et al., Meth. Enzymol., 153:516, 1987). For example, the SV40 enhancer or CMV enhancer can be used to increase expression in mammalian host cells.

The host cells for harboring and expressing the anti-OX40 antibody chains can be either prokaryotic or eukaryotic. *E. coli* is one prokaryotic host useful for cloning and expressing the polynucleotides of the present disclosure. Other microbial hosts suitable for use include bacilli, such as *Bacillus subtilis*, and other enterobacteriaceae, such as *Salmonella, Serratia*, and various *Pseudomonas* species. In these prokaryotic hosts, one can also make expression vectors, which typically contain expression control sequences compatible with the host cell (e.g., an origin of replication). In addition, any number of a variety of well-known promoters will be present, such as the lactose promoter system, a tryptophan (trp) promoter system, a beta-lactamase promoter system, or a promoter system from phage lambda. The promoters typically control expression, optionally with an operator sequence, and have ribosome binding site sequences and the like, for initiating and completing transcription and translation. Other microbes, such as yeast, can also be employed to express anti-OX40 polypeptides. Insect cells in combination with baculovirus vectors can also be used.

In other aspects, mammalian host cells are used to express and produce the anti-OX40 polypeptides of the present disclosure. For example, they can be either a hybridoma cell line expressing endogenous immunoglobulin genes or a mammalian cell line harboring an exogenous expression vector. These include any normal mortal or normal or abnormal immortal animal or human cell. For example, a number of suitable host cell lines capable of secreting intact immunoglobulins have been developed, including the CHO cell lines, various COS cell lines, HEK 293 cells, myeloma cell lines, transformed B-cells and hybridomas. The use of mammalian tissue cell culture to express polypeptides is discussed generally in, e.g., Winnacker, From Genes to Clones, VCH Publishers, NY, N.Y., 1987. Expression vectors for mammalian host cells can include expression control sequences, such as an origin of replication, a promoter, and an enhancer (see, e.g., Queen et al., Immunol. Rev. 89:49-68, 1986), and necessary processing information sites, such as ribosome binding sites, RNA splice sites, polyadenylation sites, and transcriptional terminator sequences. These expression vectors usually contain promoters derived from mammalian genes or from mammalian viruses. Suitable promoters can be constitutive, cell type-specific, stage-specific, and/or modulatable or regulatable. Useful promoters include, but are not limited to, the metallothionein promoter, the constitutive adenovirus major late promoter, the dexamethasone-inducible MMTV promoter, the SV40 promoter, the MRP polIII promoter, the constitutive MPSV promoter, the tetracycline-inducible CMV promoter (such as the human immediate-early CMV promoter), the constitutive CMV promoter, and promoter-enhancer combinations known in the art.

Methods of Detection and Diagnosis

The antibodies or antigen-binding fragments of the present disclosure are useful in a variety of applications including, but not limited to, methods for the detection of OX40. In one aspect, the antibodies or antigen-binding fragments are useful for detecting the presence of OX40 in a biological sample. The term "detecting" as used herein includes quantitative or qualitative detection. In certain aspects, a biological sample comprises a cell or tissue. In other aspects, such tissues include normal and/or cancerous tissues that express OX40 at higher levels relative to other tissues.

In one aspect, the present disclosure provides a method of detecting the presence of OX40 in a biological sample. In certain aspects, the method comprises contacting the biological sample with an anti-OX40 antibody under conditions permissive for binding of the antibody to the antigen and detecting whether a complex is formed between the antibody and the antigen. The biological sample can include, without limitation, urine or blood samples.

Also included is a method of diagnosing a disorder associated with expression of OX40. In certain aspects, the method comprises contacting a test cell with an anti-OX40 antibody; determining the level of expression (either quantitatively or qualitatively) of OX40 in the test cell by detecting binding of the anti-OX40 antibody to the OX40 polypeptide; and comparing the level of expression in the test cell with the level of OX40 expression in a control cell (e.g., a normal cell of the same tissue origin as the test cell or a non-OX40 expressing cell), wherein a higher level of OX40 expression in the test cell as compared to the control cell indicates the presence of a disorder associated with expression of OX40.

Methods of Treatment

The antibodies or antigen-binding fragments of the present disclosure are useful in a variety of applications including, but not limited to, methods for the treatment of an OX40-associated disorder or disease. In one aspect, the OX40-associated disorder or disease is a cancer.

In one aspect, the present disclosure provides a method of treating cancer. In certain aspects, the method comprises administering to a patient in need an effective amount of an anti-OX40 antibody or antigen-binding fragment. The cancer can include, without limitation, breast cancer, head and neck cancer, gastric cancer, kidney cancer, liver cancer, small cell lung cancer, non-small cell lung cancer, ovarian cancer, skin cancer, mesothelioma, lymphoma, leukemia, myeloma and sarcoma.

An antibody or antigen-binding fragment of the invention can be administered by any suitable means, including parenteral, intrapulmonary, and intranasal, and, if desired for local treatment, intralesional administration. Parenteral infusions include intramuscular, intravenous, intraarterial, intraperitoneal, or subcutaneous administration. Dosing can be by any suitable route, e.g. by injections, such as intravenous or subcutaneous injections, depending in part on whether the administration is brief or chronic. Various dosing schedules including but not limited to single or multiple administrations over various time-points, bolus administration, and pulse infusion are contemplated herein.

Antibodies or antigen-binding fragments of the invention would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The antibody need not be, but is optionally formulated with one or more agents currently used to prevent or treat the disorder in question. The effective amount of such other agents depends on the amount of antibody present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of an antibody or antigen-binding fragment of the invention will depend on the type of disease to be treated, the type of antibody, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments. Depending on the type and severity of the disease, about 1 µg/kg to 100 mg/kg of antibody can be an initial candidate dosage for administration to the patient, whether, for example, by one or more separate administrations, or by continuous infusion. One typical daily dosage might range from about 1 µg/kg to 100 mg/kg or more, depending on the factors mentioned above. For repeated administrations over several days or longer, depending on the condition, the treatment would generally be sustained until a desired suppression of disease symptoms occurs. Such doses can be administered intermittently, e.g. every week or every three weeks (e.g. such that the patient receives from about two to about twenty, or e.g. about six doses of the antibody). An initial higher loading dose, followed by one or more lower doses can be administered. However, other dosage regimens can be useful. The progress of this therapy is easily monitored by conventional techniques and assays.

Combination Therapy

In one aspect, OX40 antibodies of the present disclosure can be used in combination with other therapeutic agents. Other therapeutic agents that can be used with the OX40 antibodies of the present disclosure include: but are not limited to, a chemotherapeutic agent (e.g., paclitaxel or a paclitaxel agent; (e.g. Abraxane®), docetaxel; carboplatin; topotecan; cisplatin; irinotecan, doxorubicin, lenalidomide, 5-azacytidine, ifosfamide, oxaliplatin, pemetrexed disodium, cyclophosphamide, etoposide, decitabine, fludarabine, vincristine, bendamustine, chlorambucil, busulfan, gemcitabine, melphalan, pentostatin, mitoxantrone, pemetrexed disodium), tyrosine kinase inhibitor (e.g., EGFR inhibitor (e.g., erlotinib), multikinase inhibitor (e.g., MGCD265, RGB-286638), CD-20 targeting agent (e.g., rituximab, ofatumumab, R05072759, LFB-R603), CD52 targeting agent (e.g., alemtuzumab), prednisolone, darbepoetin alfa, lenalidomide, Bcl-2 inhibitor (e.g., oblimersen sodium), aurora kinase inhibitor (e.g., MLN8237, TAK-901), proteasome inhibitor (e.g., bortezomib), CD-19 targeting agent (e.g., MEDI-551, MOR208), MEK inhibitor (e.g., ABT-348), JAK-2 inhibitor (e.g., INCB018424), mTOR inhibitor (e.g., temsirolimus, everolimus), BCR/ABL inhibitor (e.g., imatinib), ET-A receptor antagonist (e.g., ZD4054), TRAIL receptor 2 (TR-2) agonist (e.g., CS-1008), HGF/SF inhibitor (e.g., AMG 102), EGEN-001, Polo-like kinase 1 inhibitor (e.g., BI 672).

Pharmaceutical Compositions and Formulations

Also provided are compositions, including pharmaceutical formulations, comprising an anti-OX40 antibody or antigen-binding fragment, or polynucleotides comprising sequences encoding an anti-OX40 antibody or antigen-binding fragment. In certain embodiments, compositions comprise one or more antibodies or antigen-binding fragments that bind to OX40, of on or more polynucleotides comprising sequences encoding one or more antibodies or antigen-binding fragments that bind to OX40. These compositions can further comprise suitable carriers, such as pharmaceutically acceptable excipients including buffers, which are well known in the art.

Pharmaceutical formulations of an OX40 antibody or antigen-binding fragment as described herein are prepared by mixing such antibody or antigen-binding fragment having the desired degree of purity with one or more optional pharmaceutically acceptable carriers (Remington's Pharmaceutical Sciences 16th edition, Osol, A Ed. (1980)), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) poly peptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Exemplary pharmaceutically acceptable carriers herein further include interstitial drug dispersion agents such as soluble neutral-active by hyaluronidase glycoproteins (sHASEGP), for example, human soluble PH-20 hyaluronidase glycoproteins, such as rHuPH20 (HYLENEX®, Baxter International, Inc.). Certain exemplary sHASEGPs and methods of use, including rHuPH20, are described in US Patent Nos. U.S. Pat. No. 7,871,607 and 2006/0104968. In one aspect, a sHASEGP is combined with one or more additional glycosaminoglycanases such as chondroitinases.

Exemplary lyophilized antibody formulations are described in U.S. Pat. No. 6,267,958. Aqueous antibody formulations include those described in U.S. Pat. No. 6,171,586 and WO2006/044908, the latter formulations including a histidine-acetate buffer.

Sustained-release preparations can be prepared. Suitable examples of sustained-release preparations include semipermeable matrices of solid hydrophobic polymers containing the antibody, which matrices are in the form of shaped articles, e.g. films, or microcapsules.

The formulations to be used for in vivo administration are generally sterile. Sterility can be readily accomplished, e.g., by filtration through sterile filtration membranes.

EXAMPLES

Example 1: Generation of Anti-OX40 Monoclonal Antibody

Anti-OX40 monoclonal antibodies were generated based on conventional hybridoma fusion technology (de StGroth and Sheidegger, 1980 J Immunol Methods 35:1; Mechetner, 2007 Methods Mol Biol 378:1) with minor modifications. The antibodies with high binding activity in enzyme-linked immunosorbent assay (ELISA) and fluorescence-activated cell sorting (FACS) assay were selected for further characterization.

OX40 Recombinant Proteins for Immunization and Binding Assays

The cDNA coding for the full-length human OX40 (SEQ ID NO: 1) was synthesized by Sino Biological (Beijing, China) based on the GenBank sequence (Accession No: X75962.1). The coding region of signal peptide and extracellular domain (ECD) consisting of amino acid (AA) 1-216 of OX-40 (SEQ ID NO: 2) was PCR-amplified, and cloned into in-house developed expression vectors with C-terminus fused to the Fc domain of mouse IgG2a, the Fc domain of human IgG1 wild type heavy chain or a His-tag, which resulted in three recombinant fusion protein expression plasmids, OX40-mIgG2a, OX40-huIgG1 and OX40-His, respectively. The schematic presentation of OX40 fusion proteins is shown in FIG. 1. For the recombinant fusion protein production, OX40-mIgG2a, OX40-huIgG1 and OX40-His expression plasmids were transiently transfected into 293G cells and cultured for 7 days in a $CO_2$ incubator equipped with rotating shaker. The supernatant containing the recombinant protein was collected and cleared by centrifugation. OX40-mIgG2a and OX40-huIgG1 were purified using a Protein A column (Cat: 17-5438-02, GE Life Sciences). OX40-His was purified using Ni sepharose column (Cat: 17-5318-02, GE Life Science). OX40-mIgG2a, OX40-huIgG and OX40-His proteins were dialyzed against phosphate buffered saline (PBS) and stored in an −80° C. freezer in small aliquots.

Stable Expression Cell Lines

To generate stable cell lines that express full-length human OX40 (OX40) or cynomolgus OX40 (cynoOX40), these genes were cloned into retroviral vector pFB-Neo (Cat: 217561, Agilent, USA). Retroviral transduction was performed based on a protocol described previously (Zhang et al., 2005). HuT78 and HEK293 cells were retrovirally transduced with virus containing human OX40 or cynoOX40, respectively, to generate HuT78/OX40, HEK293/OX40 and HuT78/cynoOX40 cell lines.

Immunization, Hybridoma Fusion and Cloning

Eight to twelve-week-old Balb/c mice (from HFK BIO-SCIENCE CO., LTD, Beijing, China) were immunized intraperitoneally with 200 µL of mixture antigen containing 10 µg of OX40-mIgG2a and Quick-Antibody Immuno-Adjuvant (Cat: KX0210041, KangBiQuan, Beijing, China). The procedure was repeated in three weeks. Two weeks after the $2^{nd}$ immunization, mouse sera were evaluated for OX40 binding by ELISA and FACS. Ten days after serum screening, the mice with highest anti-OX40 antibody serum titers were boosted via i.p. injection with 10 µg of OX40-mIgG2a. Three days after boosting, the splenocytes were isolated and fused to the murine myeloma cell line, SP2/0 cells (ATCC, Manassas VA), using the standard techniques (Somat Cell Genet, 1977 3:231).

Assessment of OX40 Binding Activity of Antibodies by ELISA and FACS

The supernatants of hybridoma clones were initially screened by ELISA as described in (Methods in Molecular Biology (2007) 378:33-52) with some modifications. Briefly, OX40-His protein was coated in 96-well plates at 4° C. overnight. After washing with PBS/0.05% Tween-20, plates were blocked by PBS/3% BSA for 2 hours at room temperature. Subsequently, plates were washed with PBS/0.05% Tween-20 and incubated with cell supernatants at room temperature for 1 hour. The HRP-linked anti-mouse IgG antibody (Cat: 115035-008, Jackson ImmunoResearch Inc, Peroxidase AffiniPure Goat Anti-Mouse IgG, Fcγ fragment specific) and substrate (Cat: 00-4201-56, eBioscience, USA) were used to develop the color absorbance signal at the wavelength of 450 nm, which was measured by using a plate reader (SpectraMax Paradigm, Molecular Devices/PHERAstar, BMG LABTECH). Positive parental clones were picked up from fusion screening with indirect ELISA. The ELISA-positive clones were further verified by FACS using HuT78/OX40 and HuT78/cynoOX40 cells described above. OX40-expressing cells ($10^5$ cells/well) were incubated with ELISA-positive hybridoma supernatants, followed by binding with Anti-Mouse IgG eFluor® 660 antibodies (Cat: 50-4010-82, eBioscience, USA). Cell fluorescence was quantified using a flow cytometer (Guava easyCyte 8HT, Merck-Millipore, USA).

The conditioned media from the hybridomas that showed positive signals in both ELISA and FACS screening were subjected to functional assays to identify antibodies with good functional activity in human immune cell-based assays (see following sections). The antibodies with desired functional activities were further sub-cloned and characterized.

Subcloning and Adaptation of Hybridomas to Serum-Free or Low Serum Medium

After primary screening by ELISA, FACS and functional assays as described above, the positive hybridoma clones were sub-cloned by the limiting dilution to ensure clonality. The top antibody subclones were verified by functional assays and adapted for growth in the CDM4MAb medium (Cat: SH30801.02, Hyclone, USA) with 3% FBS.

Expression and Purification of Monoclonal Antibodies

Hybridoma cells expressing the top antibody clones were cultured in CDM4MAb medium (Cat: SH30801.02, Hyclone) and incubated in a $CO_2$ incubator for 5 to 7 days at 37° C. The conditioned medium was collected through centrifugation and filtrated by passing a 0.22 µm membrane before purification. Murine antibodies in the supernatants were applied and bound to a Protein A column (Cat: 17-5438-02, GE Life Sciences) following the manufacturer's guide. The procedure usually yielded antibodies at purity above 90%. The Protein A-affinity purified antibodies were either dialyzed against PBS or if necessary, further purified using a HiLoad 16/60 Superdex 200 column (Cat: 28-9893-35, GE Life Sciences) to remove aggregates. Protein concentrations were determined by measuring absorbance at 280 nm. The final antibody preparations were stored in aliquots in an −80° C. freezer.

Example 2: Cloning and Sequence Analysis of Anti-OX40 Antibodies

Murine hybridoma clones were harvested to prepare total cellular RNAs using Ultrapure RNA kit (Cat: 74104, QIAGEN, Germany) based on the manufacturer's protocol. The $1^{st}$ strand cDNAs were synthesized using a cDNA synthesis kit from Invitrogen (Cat: 18080-051) and PCR amplification of the VH and VL of the hybridoma antibodies was performed using a PCR kit (Cat: CW0686, CWBio, Beijing, China). The oligo primers used for antibody cDNAs cloning of heavy chain variable region (VH) and light chain variable region (VL) were synthesized by Invitrogen (Beijing, China) based on the sequences reported previously (Brocks et al. 2001 Mol Med 7:461). PCR products were used directly for sequencing or subcloned into the pEASY-Blunt cloning vector (Cat: CB101 TransGen, China) then sequenced by Genewiz (Beijing, China). The amino acid sequences of VH and VL regions were deduced from the DNA sequencing results.

Complementarity determinant regions (CDRs) of the murine antibodies were defined based on the Kabat (Wu and Kabat 1970 J. Exp. Med. 132:211-250) system by sequence annotation and by computer program sequence analysis. The amino acid sequences of a representative top clone Mu445 (VH and VL) were listed in Table 1 (SEQ ID NOs. 9 and 11). The CDR sequences of Mu445 were listed in Table 2 (SEQ ID NOs. 3-8).

TABLE 1

Amino acid sequences of Mu445 VH and VL regions

| | | |
|---|---|---|
| Mu445 VH | SEQ ID NO: 9 | EVQLQQSGPELVKPGASVKMSCKASGYK FTSYIIHWVKQKPGQGLEWIGYINPYND GTRYNEKFKGKATLTSDKSSSTAYMEYS SLTSEDSAVYYCARGYYGSSYAMDYWGQ GTSVTVSS |
| Mu445 VL | SEQ ID NO: 11 | DIQMTQTTSSLSASLGDRVTISCSASQG ISNYLNWYQQKPDGTIKLLIYDTSTLYS GVPSRFSGSGSGTDYFLTISNLEPEDIA TYYCQQYSKLPYTFGGGTKLEKK |

TABLE 2

CDR sequences (amino acids) of mouse monoclonal antibody Mu445 VH and VL regions

| Antibody | SEQ ID NO | CDR | Sequence |
|---|---|---|---|
| Mu445 | SEQ ID NO: 3 | HCDR1 (Kabat) | SYIIH |
| | SEQ ID NO: 4 | HCDR2 (Kabat) | YINPYNDGTRYNEKFKG |

TABLE 2-continued

CDR sequences (amino acids) of mouse monoclonal antibody Mu445 VH and VL regions

| Antibody | SEQ ID NO | CDR | Sequence |
|---|---|---|---|
| | SEQ ID NO: 5 | HCDR3 (Kabat) | GYYGSSYAMDY |
| | SEQ ID NO: 6 | LCDR1 (Kabat) | SASQGISNYLN |
| | SEQ ID NO: 7 | LCDR2 (Kabat) | DTSTLYS |
| | SEQ ID NO: 8 | LCDR3 (Kabat) | QQYSKLPYT |

Example 3: Humanization of the Murine Anti-Human OX40 Antibody 445 Antibody Humanization and Engineering For humanization of Mu445, human germline IgG genes were searched for sequences that share high degrees of homology to the cDNA sequences of Mu445 variable regions by sequence comparison against the human immunoglobulin gene database in IMGT. The human IGHV and IGKV genes that are present in human antibody repertoires with high frequencies (Glanville et al., 2009 PNAS 106: 20216-20221) and highly homologous to Mu445 were selected as the templates for humanization.

Humanization was carried out by CDR-grafting (Methods in Molecular Biology, Antibody Engineering, Methods and Protocols, Vol 248: Humana Press) and the humanized antibodies were engineered as human IgG1 wild type format by using an in-house developed expression vector. In the initial round of humanization, mutations from murine to human amino acid residues in framework regions were guided by the simulated 3D structure analysis, and the murine framework residues with structural importance for maintaining the canonical structures of CDRs were retained in the first version of the humanized antibody 445 (see 445-1, Table 3). The six CDRs of 445-1 have amino acid sequences of HCDR1 (SEQ ID NO: 3), HCDR2 (SEQ ID NO:13), HCDR3 (SEQ ID NO:5) and LCDR1 (SEQ ID NO: 6), LCDR2 (SEQ ID NO:7), and LCDR3 (SEQ ID NO: 8). The heavy chain variable region of 445-1 has an amino acid sequence of (VH) SEQ ID NO: 14 that is encoded by a nucleotide sequence of SEQ ID NO: 15, and the light chain variable region has an amino acid sequence of (VL) SEQ ID NO: 16 that is encoded by a nucleotide sequence of SEQ ID NO: 17. Specifically, LCDRs of Mu445 (SEQ ID NO: 6-8) were grafted into the framework of human germline variable gene IGVK1-39 with two murine framework residues (I44 and Y71) retained (SEQ ID NO: 16). HCDR1 (SEQ ID NO: 3), HCDR2 (SEQ ID NO: 13) and HCDR3 (SEQ ID NO: 5) were grafted into the framework of human germline variable gene IGHV1-69 with two murine framework ($L_{70}$ and $S_{72}$) residues retained (SEQ ID NO: 14). In the 445 humanization variants (445-1), only the N-terminal half of Kabat HCDR2 was grafted, as only the N-terminal half was predicted to be important for antigen-binding according to the simulated 3D structure.

445-1 was constructed as a humanized full-length antibody using in-house developed expression vectors that contain constant regions of a human wildtype IgG1 (IgG1wt) and kappa chain, respectively, with easy adapting subcloning sites. 445-1 antibody was expressed by co-transfection of the above two constructs into 293G cells and purified using a protein A column (Cat: 17-5438-02, GE Life Sciences). The purified antibody was concentrated to 0.5-10 mg/mL in PBS and stored in aliquots in −80° C. freezer.

Using the 445-1 antibody, several single amino acid changes were made, converting the retained murine residues in framework region of the VH and VL to corresponding human germline residues, such as 144P and Y71F in the VL and L70I and S72A in VH. In addition, several single amino acid changes were made in the CDRs to reduce potential isomerization risk and to increase the humanization level. For example, the alterations of T51A and D50E were made in LCDR2 and the alterations D56E, G57A and N61A were made in HCDR2. All humanization changes were made using primers containing mutations at specific positions and a site directed mutagenesis kit (Cat: AP231-11, TransGen, Beijing, China). The desired changes were verified by sequencing.

The amino acid changes in the 445-1 antibody were evaluated for their binding to OX40 and thermal stability. Antibody 445-2 comprising HCDR1 of SEQ ID NO: 3, HCDR2 of SEQ ID NO: 18, HCDR3 of SEQ ID NO: 5, LCDR1 of SEQ ID NO: 6, LCDR2 of SEQ ID NO: 19 and LCDR3 of SEQ ID NO: 8) (see Table 3) was constructed from the combination of specific changes described above. In comparing the two antibodies the results showed that both antibodies 445-2 and 445-1 exhibited comparable binding affinity (see below in Table 4 and Table 5).

Beginning with the 445-2 antibody, several additional amino acid changes in the framework region of the VL were made to further improve binding affinity/kinetics, for example, the alteration of amino acids G41D and K42G. In addition, several single-amino acid changes in the CDRs of both the VH and VL were made in order to lower immunogenicity risk and increase thermal stability, for example, S24R in LCDR1 and A61N in HCDR2. The resulting changes showed either improved binding activities or thermal stability as compared to 445-2.

Humanized 445 antibodies were further engineered by introducing specific amino acid changes in CDRs and framework regions to improve molecular and biophysical properties for therapeutic use in humans. The considerations included removing deleterious post translational modifications, improved heat stability ($T_m$), surface hydrophobicity and isoelectronic points (pIs) while maintaining binding activities.

The humanized monoclonal antibody, 445-3, comprising HCDR of SEQ ID NO: 3, HCDR2 of SEQ ID NO: 24, HCDR 3 of SEQ ID NO: 5, LCDR1 of SEQ ID NO: 25, LCDR2 of SEQ ID NO: 19, and LCDR3 of SEQ ID NO: 8 (see Table 3), was constructed from the maturation process described above, and characterized in detail. Antibody 445-3 was also made into an IgG2 version (445-3 IgG2) comprising the Fc domain of wild-type heavy chain of human IgG2, and an IgG4 version comprising the Fc domain of human IgG4 with S228P and R409K mutations (445-3 IgG4). The results showed that 445-3 and 445-2 exhibited comparable binding affinity (see Table 4 and Table 5).

TABLE 3

445 antibody sequences

| Antibody | SEQ ID NO | | SEQUENCE |
|---|---|---|---|
| 445-1 | SEQ ID NO: 3 | HCDR1 (Kabat) | SYIIH |
| | SEQ ID NO: 13 | HCDR2 (Kabat) | YINPYNDGTRYNQKFQG |
| | SEQ ID NO: 5 | HCDR3 (Kabat) | GYYGSSYAMDY |
| | SEQ ID NO: 6 | LCDR1 (Kabat) | SASQGISNYLN |
| | SEQ ID NO: 7 | LCDR2 (Kabat) | DTSTLYS |
| | SEQ ID NO: 8 | LCDR3 (Kabat) | QQYSKLPYT |
| | SEQ ID NO: 14 | VH | QVQLVQSGAEVKKPGSSVKVSCKASGYKFTSYIIHWVRQAPGQGLEWMGYINPYNDGTRYNQKFQGRVTLTSDKSTSTAYMELSSLRSEDTAVYYCARGYYGSSYAMDYWGQGTTVTVSS |
| | SEQ ID NO: 16 | VL | DIQMTQSPSSLSASVGDRVTITCSASQGISNYLNWYQQKPGKAIKLLIYDTSTLYSGVPSRFSGSGSGTDYTLTISSLQPEDFATYYCQQYSKLPYTFGGGTKVEIK |
| 445-2 | SEQ ID NO: 3 | HCDR1 (Kabat) | SYIIH |
| | SEQ ID NO: 18 | HCDR2 (Kabat) | YINPYNEGTRYAQKFQG |
| | SEQ ID NO: 5 | HCDR3 (Kabat) | GYYGSSYAMDY |
| | SEQ ID NO: 6 | LCDR1 (Kabat) | SASQGISNYLN |
| | SEQ ID NO: 19 | LCDR2 (Kabat) | DASTLYS |
| | SEQ ID NO: 8 | LCDR3 (Kabat) | QQYSKLPYT |
| | SEQ ID NO: 20 | VH | QVQLVQSGAEVKKPGSSVKVSCKASGYKFTSYIIHWVRQAPGQGLEWMGYINPYNEGTRYAQKFQGRVTLTADKSTSTAYMELSSLRSEDTAVYYCARGYYGSSYAMDYWGQGTTVTVSS |
| | SEQ ID NO: 22 | VL | DIQMTQSPSSLSASVGDRVTITCSASQGISNYLNWYQQKPGKAIKLLIYDASTLYSGVPSRFSGSGSGTDFTLTISSLQPEDFATYYCQQYSKLPYTFGGGTKVEIK |
| 445-3 | SEQ ID NO: 3 | HCDR1 (Kabat) | SYIIH |
| | SEQ ID NO: 24 | HCDR2 (Kabat) | YINPYNEGTRYNQKFQG |
| | SEQ ID NO: 5 | HCDR3 (Kabat) | GYYGSSYAMDY |
| | SEQ ID NO: 25 | LCDR1 (Kabat) | RASQGISNYLN |
| | SEQ ID NO: 19 | LCDR2 (Kabat) | DASTLYS |
| | SEQ ID NO: 8 | LCDR3 (Kabat) | QQYSKLPYT |
| | SEQ ID NO: 26 | VH | QVQLVQSGAEVKKPGSSVKVSCKASGYKFTSYIIHWVRQAPGQGLEWMGYINPYNEGTRYNQKFQGRVTLTADKSTSTAYMELSSLRSEDTAVYYCARGYYGSSYAMDYWGQGTTVTVSS |
| | SEQ ID NO: 28 | VL | DIQMTQSPSSLSASVGDRVTITCRASQGISNYLNWYQQKPDGAIKLLIYDASTLYSGVPSRFSGSGSGTDFTLTISSLQPEDFATYYCQQYSKLPYTFGGGTKVEIK |

Figure 2:
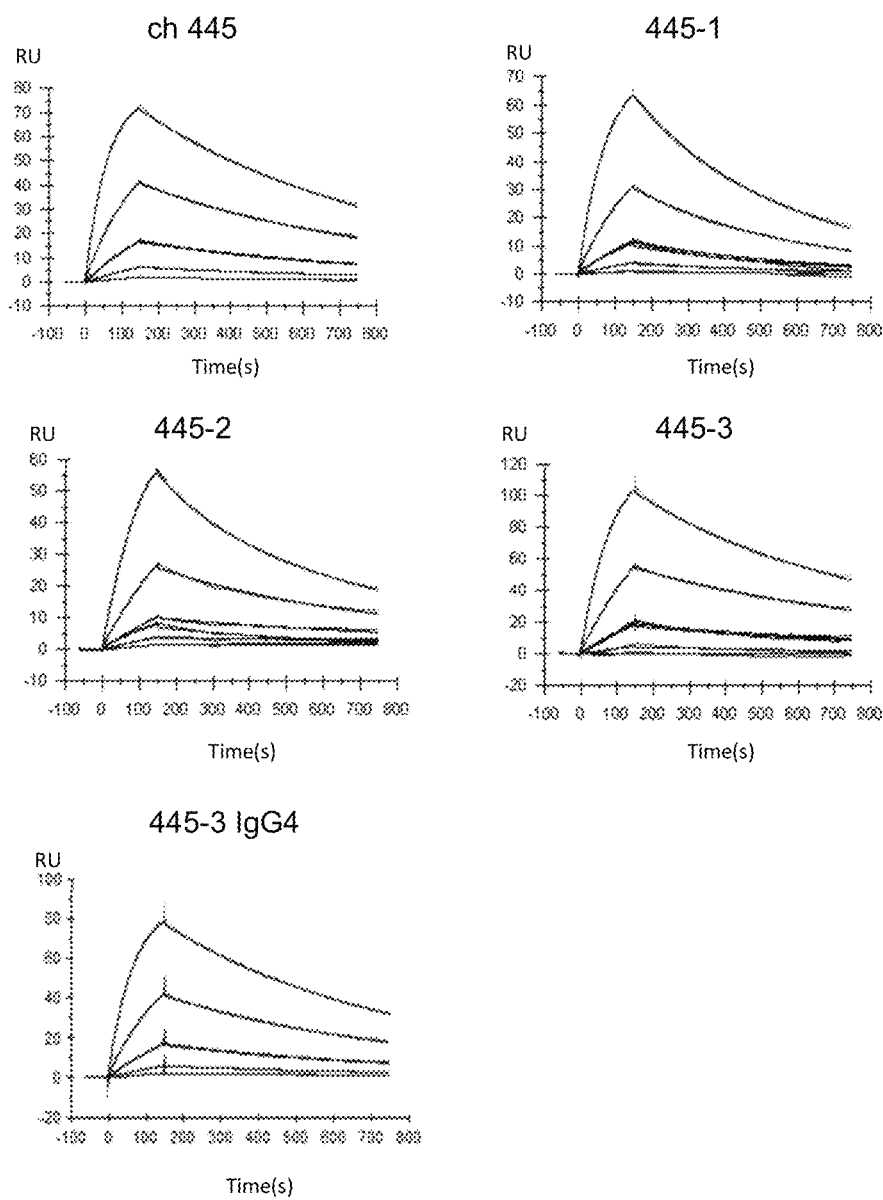
FIG. 2 shows the affinity determination of purified chimeric (ch445) and humanized (445-1, 445-2, 445-3 and 445-3 IgG4) anti-OX40 antibodies by surface plasmon resonance (SPR).

Example 4: Binding Kinetics and Affinity Determination of Anti-OX40 Antibodies by SPR The anti-OX40 antibodies were characterized for their binding kinetics and affinity by SPR assays using BIAcore™ T-200 (GE Life Sciences). Briefly, anti-human IgG antibody was immobilized on an activated CM5 biosensor chip (Cat: BR100530, GE Life Sciences). An antibody with human IgG Fc region was flowed over the chip surface and captured by anti-human IgG antibody. Then a serial dilution of recombinant OX40 protein with a His tag (Cat: 10481-H08H, Sino Biological) was flowed over the chip surface and changes in surface plasmon resonance signals were analyzed to calculate the association rates (ka) and dissociation rates (kd) by using the one-to-one Langmuir binding model (BIA Evaluation Software, GE Life Sciences). The equilibrium dissociation constant ($K_D$) was calculated as the ratio kd/ka. The results of SPR-determined binding profiles of anti-OX40 antibodies are summarized in FIG. 2 and Table 4. The binding profile with average $K_D$ of antibody 445-3 (9.47 nM) was slightly better than antibody 445-2 (13.5 nM) and 445-1 (17.1 nM), and similar to that of ch445. The binding profile of 445-3 IgG4 was similar to 445-3 (with IgG1 Fc), indicating that the change in Fc between IgG4 and IgG1 did not alter the specific binding of the 445-3 antibody.

TABLE 4

Binding affinities of anti-OX40 antibodies by SPR

| Test Parameters | ch445* | 445-1 | 445-2 | 445-3 | 445-3 IgG4 |
|---|---|---|---|---|---|
| Test 1 ka ($M^{-1}s^{-1}$) | $1.74 \times 10^5$ | $1.56 \times 10^5$ | $2.76 \times 10^5$ | $1.82 \times 10^5$ | $1.61 \times 10^5$ |
| kd ($s^{-1}$) | $1.43 \times 10^{-3}$ | $2.77 \times 10^{-3}$ | $3.90 \times 10^{-3}$ | $1.67 \times 10^{-3}$ | $1.61 \times 10^{-3}$ |
| $K_D$ (nM) | 8.26 | 17.8 | 14.2 | 9.16 | 10.0 |
| $K_A$ ($M^{-1}$) | $1.22 \times 10^8$ | $0.56 \times 10^8$ | $0.71 \times 10^8$ | $1.09 \times 10^8$ | $1.00 \times 10^8$ |
| Test 2 ka ($M^{-1}s^{-1}$) | $2.65 \times 10^5$ | $2.37 \times 10^5$ | $2.06 \times 10^5$ | $1.63 \times 10^5$ | — |
| kd ($s^{-1}$) | $1.67 \times 10^{-3}$ | $3.89 \times 10^{-3}$ | $2.64 \times 10^{-3}$ | $1.59 \times 10^{-3}$ | — |
| $K_D$ (nM) | 6.3 | 16.4 | 12.8 | 9.77 | — |
| $K_A$ ($M^{-1}$) | $1.59 \times 10^8$ | $0.61 \times 10^8$ | $0.78 \times 10^8$ | $1.03 \times 10^8$ | — |

TABLE 4-continued

Binding affinities of anti-OX40 antibodies by SPR

| Test Parameters | ch445* | 445-1 | 445-2 | 445-3 | 445-3 IgG4 |
|---|---|---|---|---|---|
| Mean $K_D$(nM) | 7.28 | 17.1 | 13.5 | 9.47 | 10.0 |
| $K_A$ ($M^{-1}$) | $1.41 \times 10^8$ | $0.59 \times 10^8$ | $0.75 \times 10^8$ | $1.06 \times 10^8$ | $1.00 \times 10^8$ |

*ch445 is comprised of Mu445 variable domains fused to human IgG1wt/kappa constant regions

Figure 3:
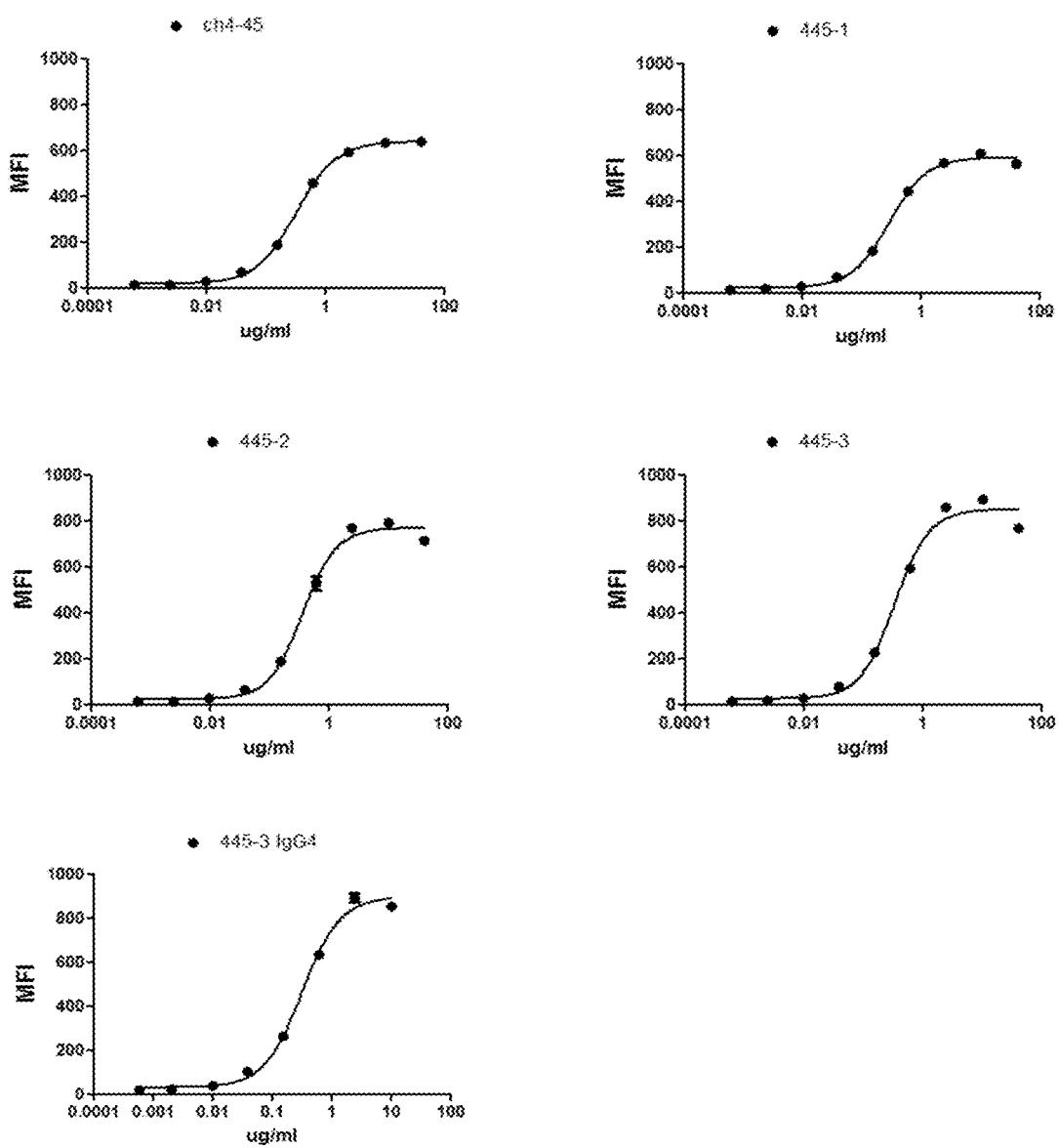
FIG. 3 demonstrates determination of OX40 binding by flow cytometry. OX40-positive HuT78/OX40 cells were incubated with various anti-OX40 antibodies (antibodies ch445, 445-1, 445-2, 445-3 and 445-3 IgG4) and subjected to FACS analysis. The result is shown by mean fluorescence intensity (MFI, Y-axis).

Example 5: Determining the Binding Affinity of Anti-OX40 Antibodies to OX40 Expressed on HuT78 Cells To evaluate the binding activity of anti-OX40 antibodies to bind OX40 expressed on the surface of live cells, HuT78 cells were transfected with human OX40 as described in Example 1 to create an OX40 expressing line. Live HuT78/OX40 cells were seeded in 96-well plate and were incubated with a serial dilution of various anti-OX40 antibodies. Goat anti-Human IgG-FITC (Cat: A0556, Beyotime) was used as a secondary antibody to detect antibody binding to the cell surface. $EC_{50}$ values for dose-dependent binding to human OX40 were determined by fitting the dose-response data to the four-parameter logistic model with GraphPad Prism. As shown in FIG. 3 and Table 5, the OX40 antibodies had high affinity to OX40. It was also found that the OX40 antibodies of the current disclosure had a relatively higher top level of fluorescence intensity measured by flow cytometry (see the last column of Table 5), indicating a slower dissociation of the antibody from OX40, which is a more desirable binding profile.

TABLE 5

$EC_{50}$ of dose-dependent binding of humanized 445 variants to OX40

| Antibody | $EC_{50}$ (µg/mL) | | | Top (MFI) |
| | Test 1 | Test 2 | Mean | Mean |
|---|---|---|---|---|
| ch445 | 0.321 | 0.277 | 0.299 | 725 |
| 445-1 | 0.293 | 0.278 | 0.285 | 525 |
| 445-2 | 0.323 | 0.363 | 0.343 | 620 |
| 445-3 | 0.337 | 0.319 | 0.328 | 910 |
| 445-3 IgG4 | 0.263 | N/A | 0.263 | 892 |

Example 6: Determining the Cross Reactivity of Anti-OX40 Antibodies

Figure 4:
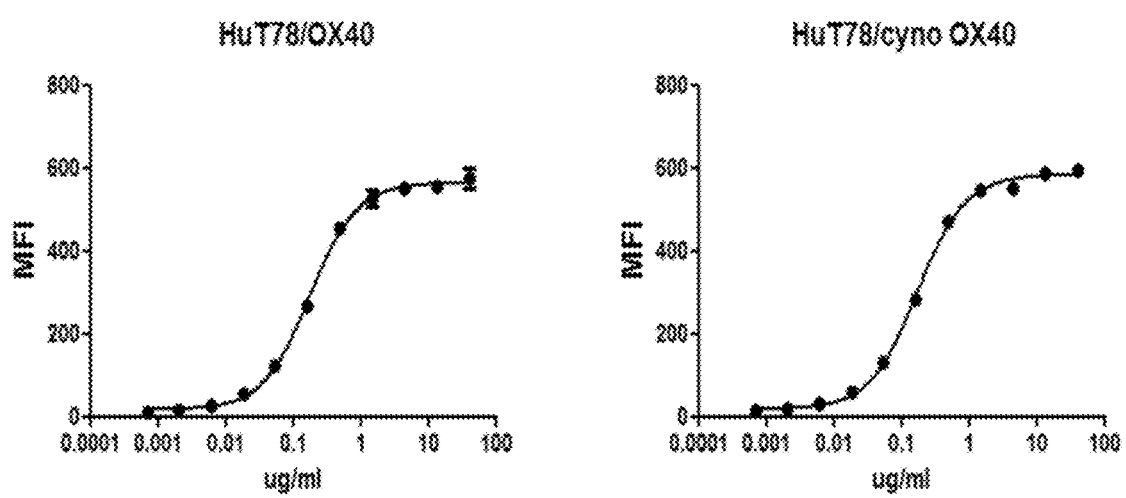
FIG. 4 shows the binding of OX40 antibodies by flow cytometry. HuT78/OX40 and HuT78/cynoOX40 cells were stained with antibody 445-3 and mean fluorescence intensity (MFI, shown in the Y-axis) was determined by flow cytometry.

To evaluate the cross reactivity of antibody 445-3 to human and cynomolgus (cyno) monkey OX40, cells expressing human OX40 (HuT78/OX40) and cyno OX40 (HuT78/cynoOX40) were seeded in 96-well plates and incubated with a series of dilutions of OX40 antibodies. Goat anti-Human IgG-FITC (Cat: A0556, Beyotime) was used as a secondary antibody for detection. $EC_{50}$ values for dose-dependent binding to human and cynomolgus monkey native OX40s were determined by fitting the dose-response data to the four-parameter logistic model with GraphPad Prism. The result is shown in FIG. 4 and Table 6 below. Antibody 445-3 cross-reacts with both human and cynomolgus monkey OX40, with similar $EC_{50}$ values as shown below.

TABLE 6

$EC_{50}$ of antibody 445-3 binding to human and cynomolgus monkey OX40

| Cell line | $EC_{50}$ µg/mL of 445-3 | Top (MFI) |
|---|---|---|
| HuT78/OX40 | 0.174 | 575 |
| HuT78/cynoOX40 | 0.171 | 594 |

Example 7: Co-Crystallization and Structural Determination of OX40 with a 445-3 Fab To understand the binding mechanism of OX40 to antibodies of the present disclosure, the co-crystal structure of OX40 and Fab of 445-3 were solved. Mutations at residues T148 and N160 were introduced to block the glycosylation of OX40 and to improve the homogeneity of the protein. The DNA encoding the mutant human OX40 (residues M1-D170 with the two mutated sites, T148A and N160A) was cloned into an expression vector with the inclusion of a hexa-His tag, and this construct was transiently transfected into 293G cells for protein expression at 37° C. for 7 days. The cells were harvested, and the supernatant was collected and incubated with His tag affinity resin at 4° C. for 1 hour. The resin was rinsed three times with a buffer containing 20 mM Tris, pH 8.0, 300 mM NaCl and 30 mM imidazole. The OX40 protein was then eluted with a buffer containing 20 mM Tris, pH 8.0, 300 mM NaCl and 250 mM imidazole, followed by further purification with Superdex 200 (GE Healthcare) in a buffer containing 20 mM Tris, pH 8.0, 100 mM NaCl.

The coding sequences of heavy chain and light chain of 445-3 Fab were cloned into an expression vector with the inclusion of a hexa-His tag at the C-terminal of the heavy chain, and these were transiently co-transfected into 293G cells for protein expression at 37° C. for 7 days. The purification steps of the 445-3 Fab were the same as used for the mutant OX40 protein above.

Purified OX40 and 445-3 Fab were mixed with a molar ratio of 1:1 and incubated for 30 minutes on ice, followed by further purification with Superdex 200 (GE Healthcare) in a buffer containing 20 mM Tris, pH 8.0, 100 mM NaCl. The complex peak was collected and concentrated to approximately 30 mg/ml.

The co-crystal screen was performed by mixing the protein complex with reservoir solution by a volume ratio of 1:1. The co-crystals were obtained from hanging drops cultured at 20° C. by vapor diffusion with a reservoir solution containing 0.1 M HEPES, pH 7.0, 1% PEG 2,000 MME and 0.95 M sodium succinate.

Nylon loops were used to harvest the co-crystals and the crystals were immersed in reservoir solution supplemented with 20% glycerol for 10 seconds. Diffraction data was collected at BL17U1, Shanghai Synchrotron Radiation Facility, and were processed with XDS program. The phase was solved with program PHASER using a structure of IgG Fab (chains C and D of PDB: 5CZX) and the structure of OX40 (chain R of PDB: 2HEV) as the molecular replacement searching models. The Phenix.refine graphical interface was used to perform rigid body, TLS, and restrained refinement against X-ray data, followed by adjustment with the COOT program and further refinement in Phenix.refine program. The X-ray data collection and refinement statistics are summarized in Table 7.

TABLE 7

Data collection and refinement statistics

| Data collection | |
| --- | --- |
| Beamline | BL17U1, SSRF |
| Space group | P 31 2 1 |
| Cell dimensions (Å) | a = 183.96 |
| | b = 183.96 |
| | c = 79.09 |
| Angles (°) | α = 90.00 |
| | β = 90.00 |
| | γ = 120.00 |
| Resolution (Å) | 159.3-2.55 |
| | (2.63-2.55) |
| Total number of reflections | 988771 |
| | (81305) |
| Number of unique reflections | 50306 |
| | (4625) |
| Completeness (%) | 99.9 |
| | (99.9) |
| Average redundancy | 19.7 |
| | (17.6) |
| Rmerge$^a$ | 0.059 |
| | (0.962) |
| I/sigma (I) | 29.4 |
| | (3.5) |
| Wilson B factor (Å) | 73.9 |
| Refinement | |
| Resolution (Å) | 60.22-2.55 |
| Number of reflections | 50008 |
| rmsd bond lengths (Å) | 0.010 |
| rmsd bond angles (°) | 0.856 |
| Rwork$^b$ (%) | 19.27 |
| Rfree$^c$ (%) | 21.60 |
| Average B-factors of protein | 97.10 |
| Ramachandran plot (%) | |
| Favored | 96.34 |
| Allowed | 3.48 |
| Outliers | 0.17 |

Values in parentheses refer to the highest resolution shell.

$^a$Rmerge = Σ Σ$_j$|I(h)$_j$ − ⟨I(h)⟩|/Σ Σ$_j$|I(h)$_j$|, where ⟨I(h)⟩ is the mean intensity of equivalent.
$^b$R$_{work}$ = Σ|Fo − Fc|/Σ|Fo|, where Fo and Fc are the observed and calculated structure factor amplitudes, respectively.
$^c$R$_{free}$ = Σ|Fo − Fc|/Σ|Fo|, calculated using a test data set, 5% of total data randomly selected from the observed reflections.

Example 8: Epitope Identification of Antibody 445-3 by SPR

Guided by the co-crystal structure of OX40 and antibody 445-3 Fab, we selected and generated a series of single mutations in human OX40 protein to further identify the key epitopes of anti-OX40 antibodies of the present disclosure. The single point mutations were made to a human OX40/IgG1 fusion construct with a site-directed mutagenesis kit (Cat: AP231-11, TransGen). The desired mutations were verified by sequencing. Expression and preparation of the OX40 mutants were achieved by transfection into 293G cells and purified using a protein A column (Cat: 17-5438-02, GE Life Sciences).

Figure 5:
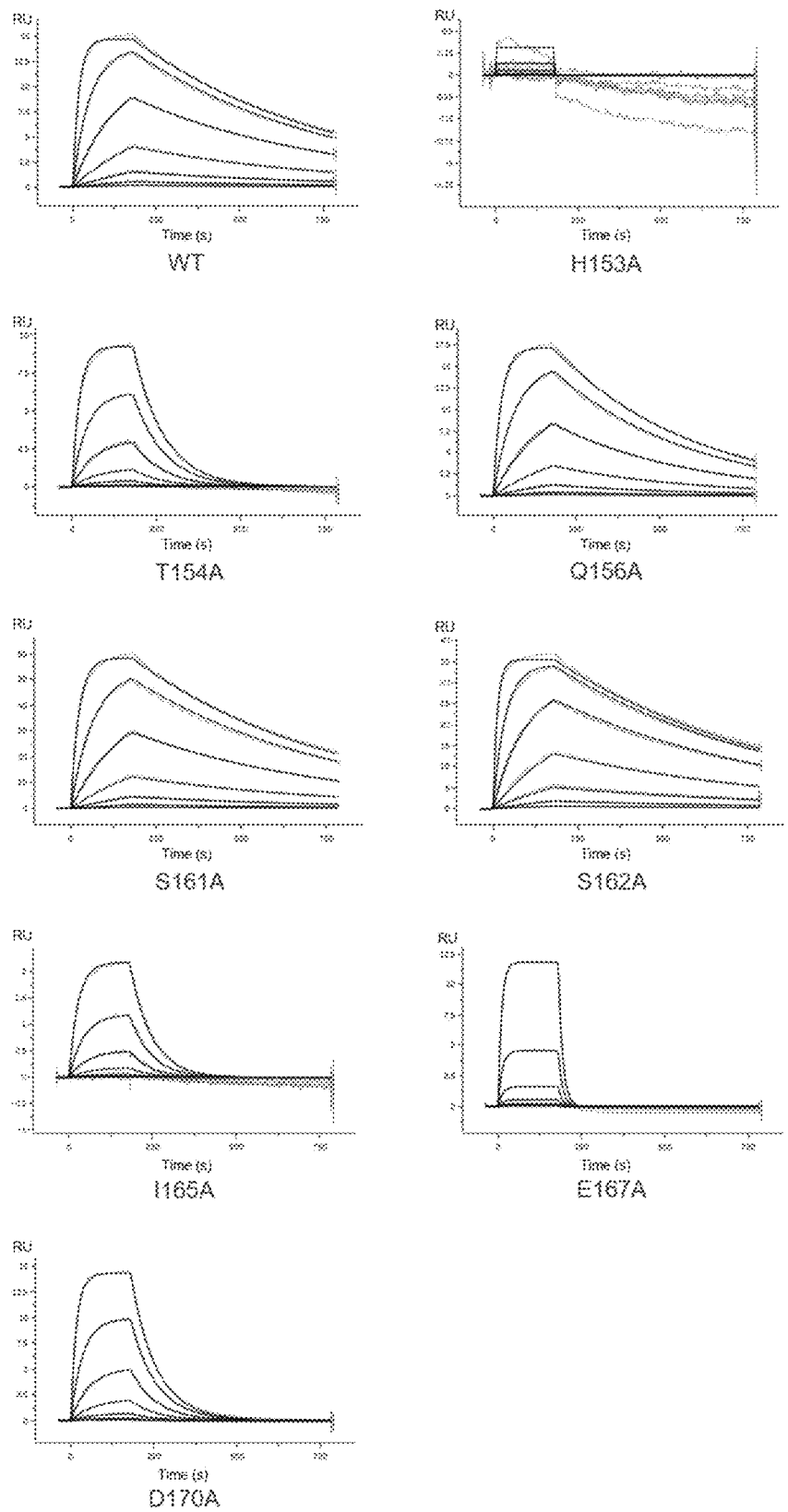
FIG. 5 depicts the affinity determination of a 445-3 Fab against OX40 wild type and point mutants by surface plasmon resonance (SPR).

Binding affinity of the OX40 point mutants to a 445-3 Fab were characterized by SPR assays using BIACORE™ 8K (GE Life Sciences). Briefly, OX40 mutants and wild type OX40 were immobilized on a CM5 biosensor chip (Cat: BR100530, GE Life Sciences) using EDC and NHS. Then a serial dilution of 445-3 Fab in HBS-EP+ buffer (Cat: BR-1008-26, GE Life Sciences) was flowed over the chip surface using a contact time of 180 s and a dissociation time of 600 s at 30 μl/min. The changes in surface plasmon resonance signals were analyzed to calculate the association rates (ka) and dissociation rates (kd) by using the one-to-one Langmuir binding model (BIA Evaluation Software, GE Life Sciences). The equilibrium dissociation constant ($K_D$) was calculated as the ratio kd/ka. The $K_D$ shift fold of mutant was calculated as the ratio Mutant $K_D$/WT $K_D$. The profiles of epitope identification determined by SPR are summarized in FIG. 5 and Table 8. The results indicated that mutation of residues H153, I165 and E167 to alanine in OX40 significantly reduced antibody 445-3 binding to OX40, and the mutation of residues T154 and D170 to alanine had moderate reduction of antibody 445-3 binding to OX40.

Figure 6:
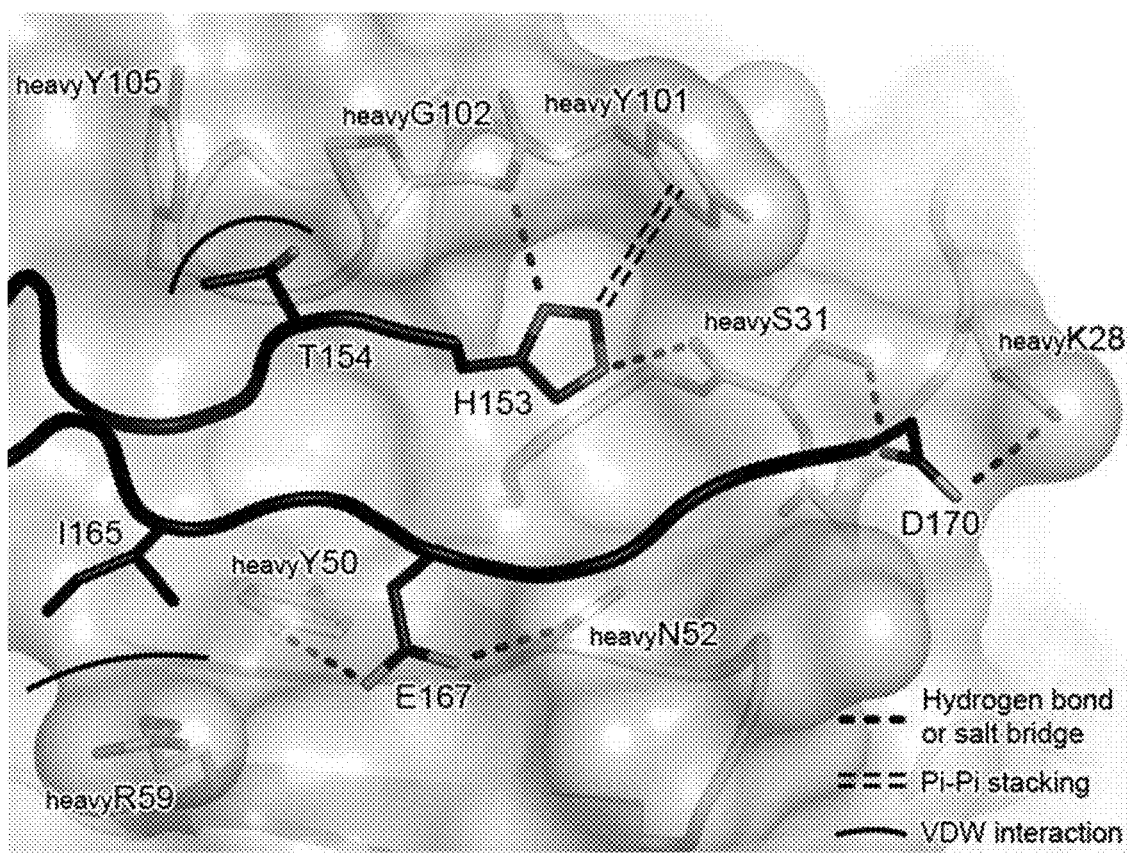
FIG. 6 shows the detailed interactions between antibody 445-3 and its epitopes on OX40. Antibody 445-3 and OX40 are depicted in pale gray and black, respectively. Hydrogen bonds or salt bridge, pi-pi stacking and Van der Waals (VDW) interaction are indicated with dashed, double dashed and solid lines, respectively.

The detailed interactions between antibody 445-3 and residues H153, T154, I165, E167 and D170 of OX40 are shown in FIG. 6. The side chain of H153 on OX40 was surrounded by a small pocket of 445-3 on the interaction interface, forming hydrogen bonds with $_{heavy}$S31 and $_{heavy}$G102 and pi-pi stacking with $_{heavy}$Y101. The side chain of E167 formed hydrogen bonds with $_{heavy}$Y50 and $_{heavy}$N52, while D170 formed a hydrogen bond and a salt bridge with $_{heavy}$S31 and $_{heavy}$K28, respectively, which can further stabilize the complex. Van der Waals (VDW) interactions between T154 and $_{heavy}$Y105, I165 and $_{heavy}$R59 contributed to a high affinity of antibody 445-3 to OX40.

In conclusion, residues H153, I165 and E167 of OX40 were identified as important residues to interact with antibody 445-3. In addition, amino acids T154 and D170 of OX40 are also important contact residues for antibody 445-3. This data indicated that the epitopes of antibody 445-3 are residues H153, T154, I165, E167 and D170 of OX40. These epitopes reside in the sequence <u>H</u>TLQPASNSSD<u>A</u>I<u>CEDRD</u> (SEQ ID NO:30) with the important contact residues bolded and underlined.

TABLE 8

Epitope identification of antibody 445-3 determined by SPR

| Mutants | Mutant $K_D$/WT $K_D$ |
| --- | --- |
| H153A | No binding was detected |
| T154A | 8 |
| Q156A | 1.9 |
| S161A | 1.1 |
| S162A | 0.6 |
| I165A | 28 |
| E167A | 135 |
| D170A | 8 |

Significant impact: No binding was detected, or the value of Mutant $K_D$/WT $K_D$ was larger than 10.
Moderate impact: Mutant $K_D$/WT $K_D$ was valued between 5 and 10. Non-significant impact: The value of Mutant $K_D$/WT $K_D$ was smaller than 5.

Example 9: Anti-OX40 Antibody 445-3 does not Block OX40-OX40L Interaction

To determine whether antibody 445-3 interferes with OX40-OX40L interaction, a cell-based flow cytometry assay was established. In this assay, antibody 445-3, reference antibody 1A7.gr1, control huIgG or medium alone was pre-incubated with a human OX40 fusion protein with murine IgG2a Fc (OX40-mIgG2a). The antibody and fusion protein complex was then added to OX40L-expressing HEK293 cells. If an OX40 antibody does not interfere with OX40-OX40L interaction, then the OX40 antibody-OX40 mIgG2a complex will still bind to surface OX40L, and this interaction is detectable using an anti-mouse Fc secondary antibody.

Figure 7:
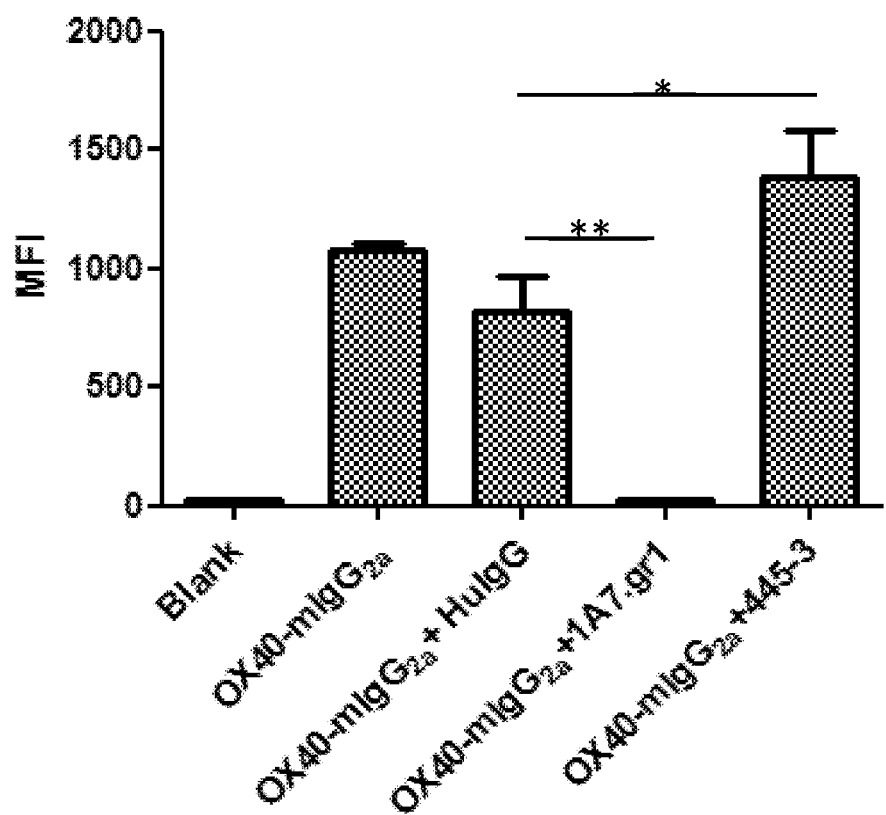
FIG. 7 demonstrates that antibody 445-3 does not interfere with OX40L binding. Prior to staining HEK293/OX40L cells, OX40-mouse IgG2a (OX40-mIgG2a) fusion protein was pre-incubated with human IgG (+HuIgG), antibody 445-3 (+445-3) or antibody 1A7.gr1 (+1A7.gr1, see US 2015/0307617), at a molar ratio of 1:1. Binding of OX40L to OX40-mIgG2a/anti-OX40 antibody complex was determined by co-incubation of HEK293/OX40L cells and OX40-mIgG2a/anti-OX40 antibody complex followed by reaction with anti-mouse IgG secondary Ab and flow cytometry. Results were shown in mean±SD of duplicates. Statistical significance: *: P<0.05; **: P<0.01.

As shown in FIG. 7, antibody 445-3, even at high concentration, did not reduce the binding of OX40 to OX40L, indicating that 445-3 does not interfere with the OX40-OX40L interaction. This indicates that 445-3 does not bind at the OX40L binding site or bind close enough to sterically hinder OX40L binding. In contrast, positive control antibody, 1A7.gr1 completely blocks OX40 binding to OX40L as shown in FIG. 7.

Figure 8:
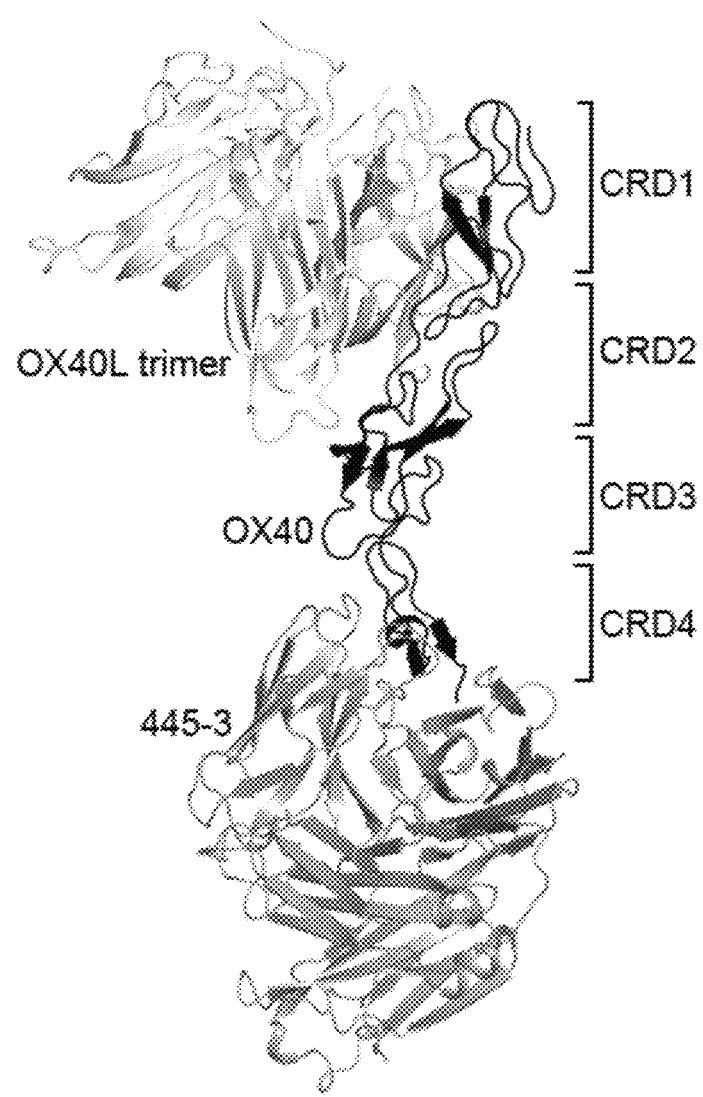
FIG. 8 shows the structural alignment of OX40/445-3 Fab with the reported OX40/OX40L complex (PDB code: 2HEV). The OX40L is shown in white, 445-3 Fab, shown in grey and OX40 is shown in black.

In addition, the co-crystal structure of OX40 in complex with 445-3 Fab was solved and aligned with the OX40/OX40L complex (PDB code: 2HEV) as shown in FIG. 8. The OX40 ligand trimer interacts with OX40 mostly through CRD1 (cysteine rich domain), CRD2 and partial CRD3 regions of the OX40 (Compaan and Hymowitz, 2006), while antibody 445-3 interacts with OX40 only through the CRD4 region. In summary, the 445-3 antibody and the OX40L trimer bind at different respective regions of OX40 and antibody 445-3 does not interfere with OX40/OX40L interaction. This result correlates with the epitope mapping data described in the Examples above. CRD4 of OX40 is at amino acids 127-167, and the epitope of antibody 445-3 partially overlaps with this region. The sequence of the OX40 CRD4 (amino acids 127-167) is shown below, and the partial overlap of the 445-3 epitope is bolded and underlined: PCPPGHFSPGDNQACKPWTNCT-LAGKHTLQPASNSSDAICE (SEQ ID NO:31).

Example 10: Agonistic Activity of Anti-OX40 Antibody 445-3

Figure 9:
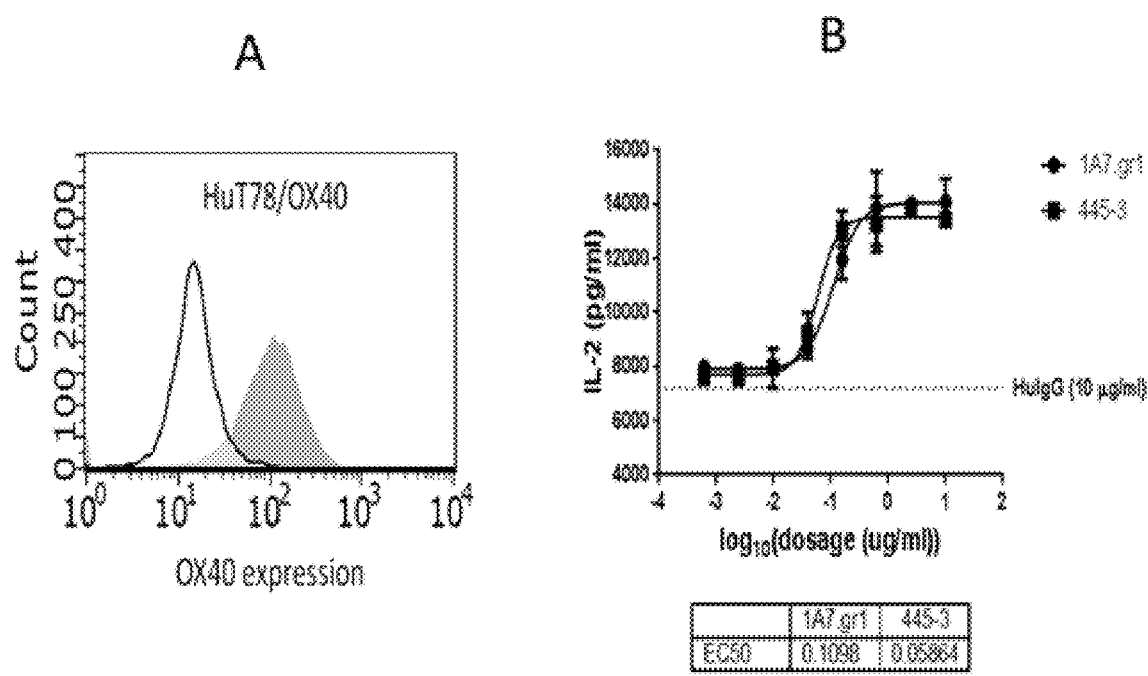
FIG. 9A-B shows that anti-OX40 antibody 445-3 induces IL-2 production in conjunction with TCR stimulation. OX40-positive HuT78/OX40 cells (FIG. 9A) were co-cultured with an artificial antigen-presenting cell (APC) line (HEK293/OS8$^{Low}$-FcγRI) in the presence of anti-OX40 antibodies overnight and IL-2 production was used as readout for T-cell stimulation (FIG. 9B). IL-2 in the culture supernatant was detected by ELISA. Results are shown in mean±SD of triplicates.

To investigate the agonistic functions of antibody 445-3, an OX40-positive T-cell line, HuT78/OX40 was co-cultured with an artificial antigen-presenting cell (APC) line (HEK293/OS8$^{low}$-FcγRI) in the presence or absence of 445-3 or 1A7.gr1 overnight and IL-2 production was used as readout for T-cell stimulation. In HEK293/OS8$^{Low}$-FcγRI cells, genes coding for the membrane-bound anti-CD3 antibody OKT3 (OS8) (as disclosed in U.S. Pat. No. 8,735,553) and human FcγRI (CD64) were stably co-transduced into HEK293 cells. Since anti-OX40 antibody-induced immune activation depends on antibody crosslinking (Voo et al., 2013), FcγRI on HEK293/OS8$^L$ow-FcγRI provides the foundation for anti-OX40 antibody-mediated cross-linking of OX40 upon the dual engagement of anti-OX40 antibody to both OX40 and FcγRI. As shown in FIG. 9, anti-OX40 antibody 445-3 was highly potent in enhancing TCR signaling in a dose-dependent manner with $EC_{50}$ at 0.06 ng/ml. Slightly weaker activities of the reference Ab 1A7.gr1 was also observed. In contrast, control human IgG (10 μg/mL) or blank showed no effect on IL-2 production.

Example 11: Anti-OX40 Antibody 445-3 Promoted Immune Responses in Mixed Lymphocyte Reaction (MLR) Assay To determine if antibody 445-3 can stimulate T cell activation, a mixed lymphocyte reaction (MLR) assay was set up as described previously (Tourkova et al., 2001). In brief, mature DCs were induced from human PBMC-derived CD14$^+$ myeloid cells by culture with GM-CSF and IL-4, followed by LPS stimulation. Next, mitomycin C-treated DCs were co-cultured with allogenic CD4$^+$ T cells in the presence of anti-OX40 445-3 antibody (0.1-10 μg/ml) for 2 days. IL-2 production in the co-culture was detected by ELISA as the readout of MLR response.

Figure 10:
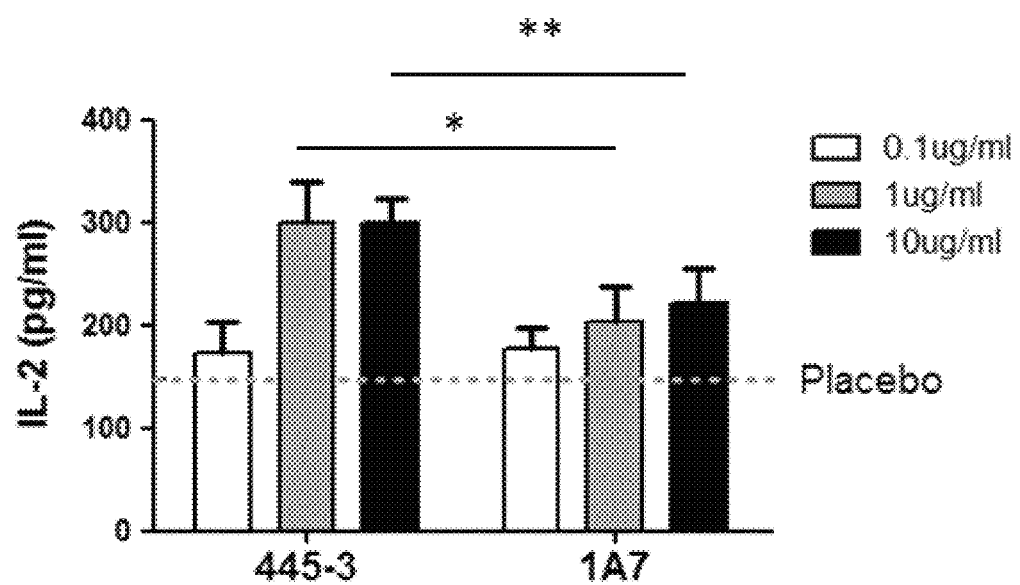
FIG. 10 indicates that anti-OX40 antibodies enhance MLR responses. In vitro differentiated dendritic cells (DC) were co-cultured with allogeneic CD4$^+$ T cells in the presence of anti-OX40 antibodies (0.1-10 μg/ml) for 2 days. IL-2 in the supernatant was detected by ELISA. All tests were performed in quadruplicates and results were shown as mean SD. Statistical significance: *: P<0.05; **: P<0.01.

As shown in FIG. 10, antibody 445-3 significantly promoted IL-2 production, indicating the ability of 445-3 to activate CD4$^+$ T-cells. In contrast, the reference antibody 1A7.gr1 showed significantly ($P<0.05$) weaker activities in MLR assay.

Example 12: Anti-OX40 Antibody 445-3 Showed ADCC Activity

A lactate dehydrogenase (LDH) release-based ADCC assay was set up to investigate whether antibody 445-3 could kill OX40$^{Hi}$ expressing target cells. NK92MI/CD16V cell line was generated as the effector cells by co-transducing CD16v158 (V158 allele) and FcRγ genes into an NK cell line, NK92MI (ATCC, Manassas VA). An OX40-expressing T-cell line, HuT78/OX40, was used as the target cells. Equal numbers ($3\times10^4$) of target cells and effector cells were co-cultured for 5 hours in the presence of an anti-OX40 antibody (0.004-3 μg/ml) or control Abs. Cytotoxicity was evaluated by LDH release using the CytoTox 96 Non-Radioactive Cytotoxicity Assay kit (Promega, Madison, WI). Specific lysis was calculated by the formula shown below.

$$\% \text{ Specific lysis} = \frac{\text{Experimental} - \text{Effector Spontaneous} - \text{Target Spontaneous}}{\text{Target Maximum} - \text{Target Spontaneous}} \times 100$$

Figure 11:
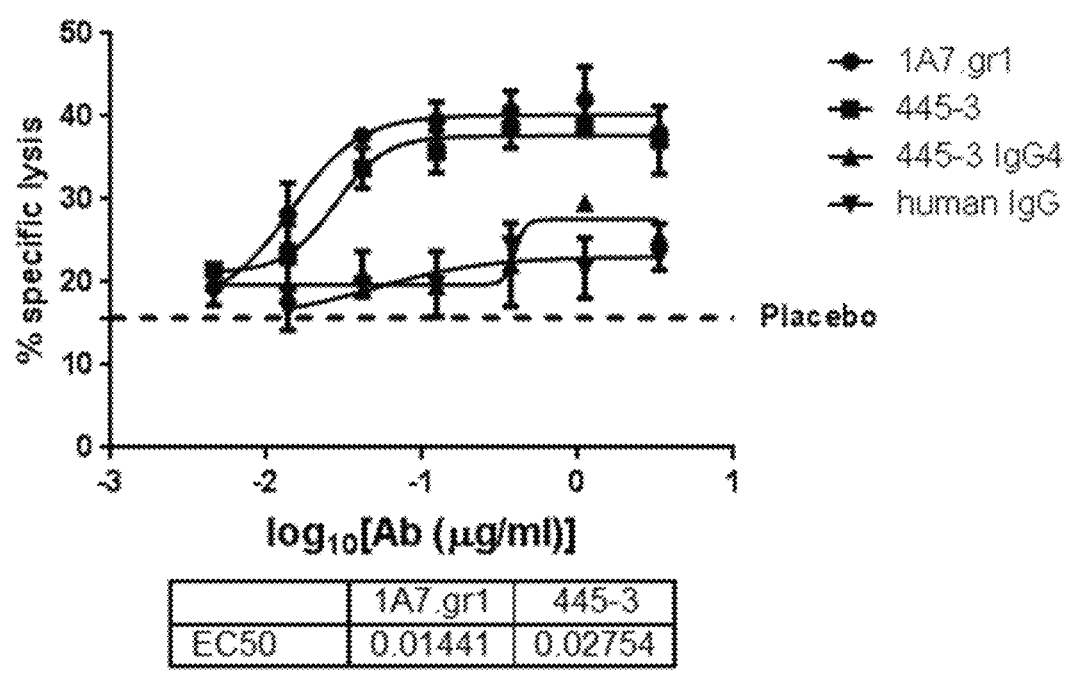
FIG. 11 demonstrates that anti-OX40 antibody 445-3 induces ADCC. ADCC assay was performed using NK92MI/CD16V cells as the effector cells and HuT78/OX40 cells as the target cells in the presence of anti-OX40 antibodies (0.004-3 μg/ml) or controls. Equal numbers of effector cells and target cells were co-cultured for 5 hours before detecting lactate dehydrogenase (LDH) release. Percentage of cytotoxicity (Y-axis) was calculated based on manufacturer's protocol as described in Example 12. Results are shown in mean±SD of triplicates.

As shown in FIG. 11, antibody 445-3 showed high potency in killing OX40$^{Hi}$ targets via ADCC in a dose-dependent manner ($EC_{50}$: 0.027 μg/mL). The ADCC effect of antibody 445-3 was similar to that of the 1A7.gr1 control antibody. In contrast, 445-3 with IgG4 Fc format with S228P and R409K mutations (445-3-IgG4) did not show any significant ADCC effects, as compared with control human IgG or blank. The results are consistent with previous findings that IgG4 Fc is weak or silent for ADCC (An Z, et al. mAbs 2009).

Example 13: Anti-OX40 Antibody 445-3 Preferentially Depletes CD4$^+$ Tregs and Increase CD8$^+$ Teff/Treg Ratios In Vitro It has been shown in several animal tumor models that anti-OX40 antibodies could deplete tumor-infiltrating OX40$^{Hi}$ Tregs and increase the ratios of CD8$^+$ T cells to Tregs (Bulliard et al., 2014; Carboni et al., 2003; Jacquemin et al., 2015; Marabelle et al., 2013b). Consequently, immune response was enhanced, leading to tumor regression and improved survival.

Figures 12A, 12B, 12C:
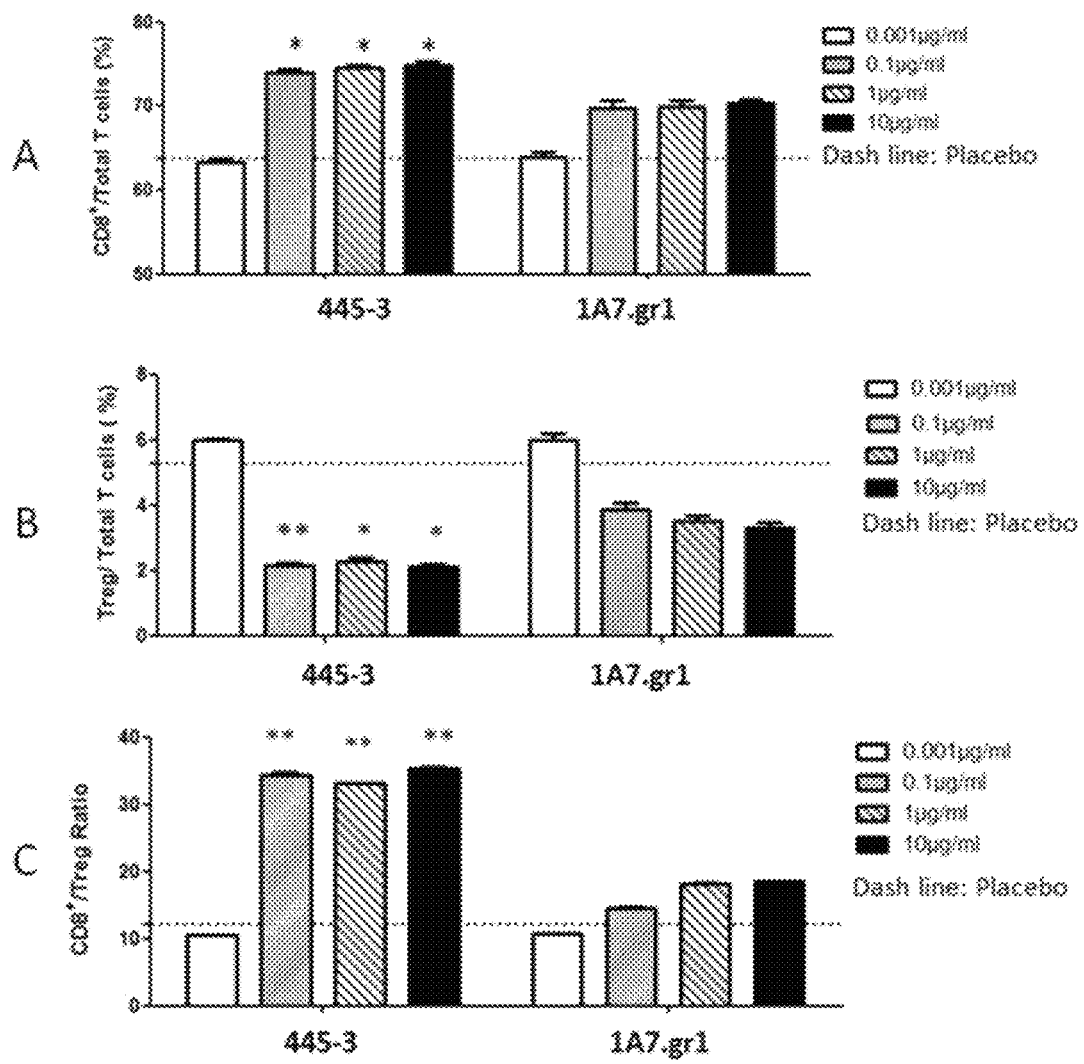
FIG. 12A-12C show that anti-OX40 antibody 445-3 in combination with NK cells increases the ratios of CD8$^+$ effector T cells to Tregs in activated PBMCs in vitro. Human PBMCs were pre-activated by PHA-L (1 μg/ml) and then co-cultured with NK92MI/CD16V cells in the presence of anti-OX40 antibodies or control. The percentages of different T-cell subsets were determined by flow cytometry. The ratios of CD8$^+$ effector T cells to Tregs were further calculated.

Given the fact that in vitro activated or intra-tumoral CD4$^+$Foxp3$^+$ Tregs preferentially express OX40 than other T-cell subsets (Lai et al., 2016; Marabelle et al., 2013b; Montler et al., 2016; Soroosh et al., 2007; Timperi et al., 2016), a human PBMC-based assay was set up to investigate the ability of antibody 445-3 to kill OX40$^{Hi}$ cells, particularly Tregs. In brief, PBMCs were pre-activated for 1 day by PHA-L (1 μg/mL) for the induction of OX40 expression and were used as target cells. Effector NK92MI/CD16V cells (as described in Example 12, 5×10⁴) were then co-cultured with equal number of target cells in the presence of anti-OX40 antibodies (0.001-10 µg/mL) or placebo overnight. The percentages of each T-cell subsets were determined by flow cytometry. As shown in FIGS. 12A and 12B, treatment with antibody 445-3 induced an increase in the percentage of CD8⁺ T cells and a decrease in the percentage of CD4⁺ Foxp3⁺ Tregs in a dose-dependent manner. As a result, the ratios of CD8⁺ T cells to Tregs were greatly improved (FIG. 12C). Weaker results were obtained with 1A7.gr1 treatment. This result demonstrates the therapeutic applications of 445-3 in inducing anti-tumor immunity by boosting CD8⁺ T cell functions, but limiting Treg-mediated immune tolerance.

Example 14: Anti-OX40 Antibody 445-3 Exerts Dose-Dependent Anti-Tumor Activity in a Mouse Tumor Model The efficacy of anti-OX40 antibody 445-3 was shown in a mouse tumor model. Murine MC38 colon tumor cells were subcutaneously implanted in C57 mice transgenic for human OX40 (Biocytogen, Beijing China). After implantation of tumor cells, tumor volumes were measured twice weekly and calculated in mm³ using the formula: V=0.5(a×b²) where a and b were the long and short diameters of the tumor, respectively. When tumors reached a mean volume of approximately 190 mm³ in size, mice were randomly allocated into 7 groups, and injected intraperitoneally with either 445-3 or 1A7.gr1 antibody once a week for three weeks. Human IgG was administered as isotype control. Partial regression (PR) was defined as tumor volume smaller than 50% of the starting tumor volume on the first day of dosing in three consecutive measurements. Tumor growth inhibition (TGI) was calculated using the following formula:

$$\% \text{ growth inhibition} = 100 \times \left(1 - \left(\frac{(\text{treated } t) - (\text{treated } t_0)}{(\text{placebo } t) - (\text{placebo } t_0)}\right)\right)$$

treated t=treated tumor volume at time t
treated t₀=treated tumor volume at time 0
placebo t=placebo tumor volume at time t
placebo t₀=placebo tumor volume at time 0

Figure 13A:
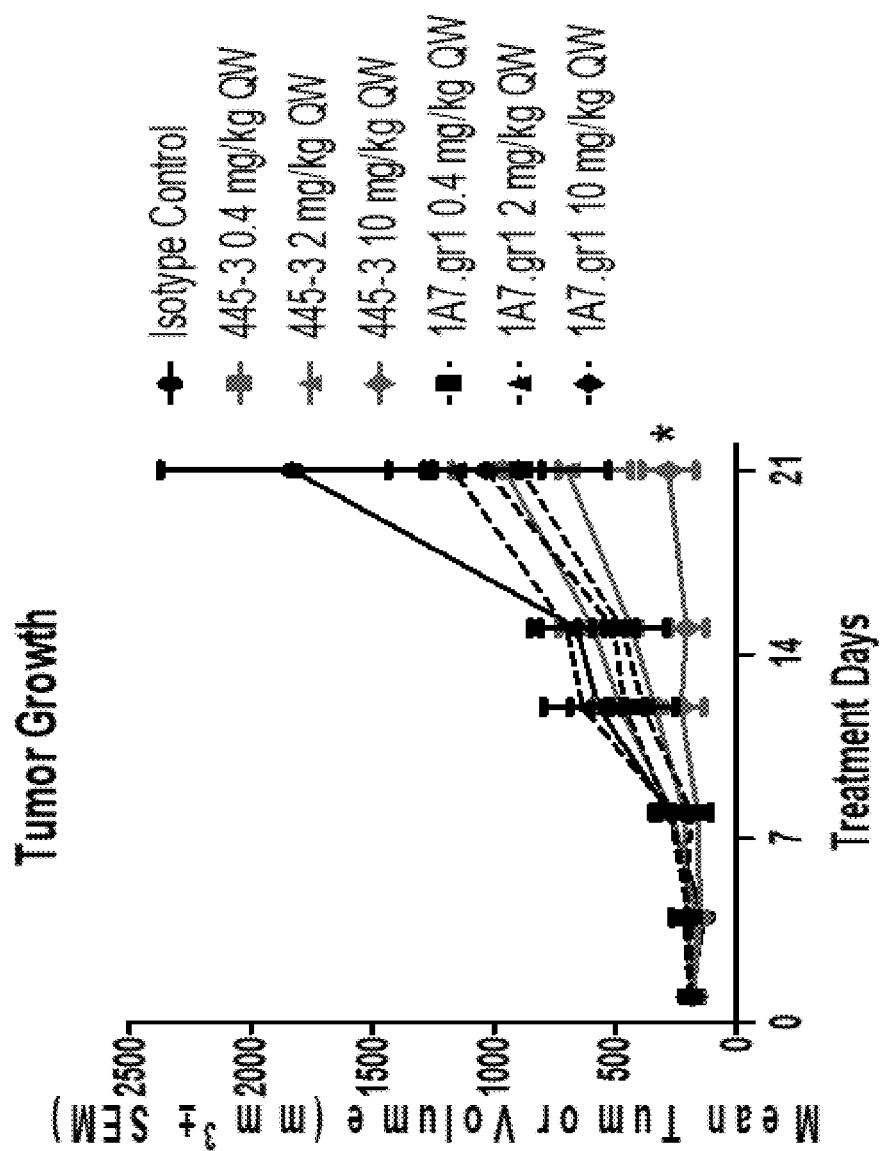
FIG. 13A-13B show that anti-OX40 antibody 445-3, but not 1A7.gr1, reveals dose-dependent anti-tumor activity in MC38 colorectal cancer syngeneic model in OX40-humanized mice. MC38 murine colon carcinoma cells (2×10$^7$) were implanted subcutaneously in female human OX40 transgenic mice. After randomization according to the tumor volume, animals were intraperitoneal injected with either anti-OX40 antibodies or isotype control once a week for three times as indicated.
Figure 13B:
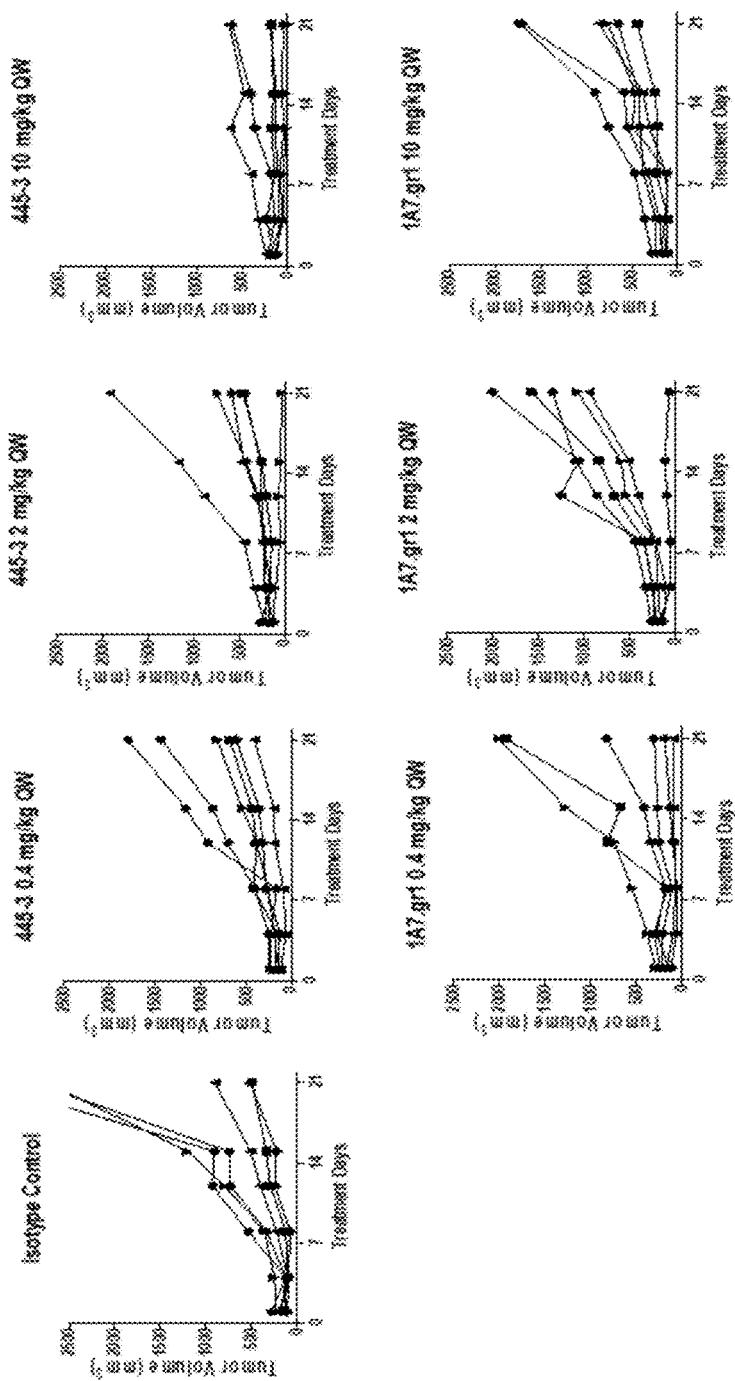

The results demonstrated that 445-3 had dose-dependent anti-tumor efficacy as an intraperitoneal injection with doses of 0.4 mg/kg, 2 mg/kg, and 10 mg/kg. Administration of 445-3 resulted in 53% (0.4 mg/kg), 69% (2 mg/kg), and 94% (10 mg/kg) tumor growth inhibition, and resulted in 0% (0.4 mg/kg), 17% (2 mg/kg), and 33% (10 mg/kg) partial regression from the baseline. In contrast, no partial regression by antibody 1A7.gr1 was observed. The in vivo data indicate that ligand-non-blocking antibody 445-3 is better suited for anti-tumor therapy than the OX40-OX40L blocking antibody 1A7.gr1 (FIGS. 13A and 13B, Table 9).

TABLE 9

The efficacy of 445-3 and 1A7.gr1 in a murine MC38 colon tumor mouse model

| Treatment | QW Dose (mg/kg) | N | Partial Regression Rate | Mean Tumor Volume on Day 21 (mm³) | TGI on Day 21 (%) |
|---|---|---|---|---|---|
| 445-3 | 0.4 | 6 | 0% | 953 | 53 |
| | 2 | 6 | 17% | 696 | 69 |
| | 10 | 6 | 33% | 280 | 94 |
| 1A7.gr1 | 0.4 | 6 | 0% | 886 | 57 |
| | 2 | 6 | 0% | 1163 | 41 |
| | 10 | 6 | 0% | 1030 | 49 |

Example 15: Amino Acid Alterations of Anti-OX40 Antibodies

Several amino acids were chosen for alteration for improvement of the OX40 antibodies. Amino acid changes were made to improve affinity, or to increase humanization. PCR primer sets were designed for the appropriate amino acid alterations, synthesized and used to modify the anti-OX40 antibodies. For example, the alteration of K28T in the heavy chain and S24R in the light chain resulted in a 1.7 fold increase to the $EC_{50}$ determined by FACS over the original 445-2 antibody. The alteration of Y27G in the heavy chain and S24R in the light chain resulted in a 1.7 fold increase to the $K_D$ determined by Biacore over the original 445-2 antibody. These changes are summarized in FIGS. 14A-14B.

REFERENCES al-Shamkhani, A., Birkeland, M. L., Puklavec, M., Brown, M. H., James, W., and Barclay, A. N. (1996). OX40 is differentially expressed on activated rat and mouse T cells and is the sole receptor for the OX40 ligand. European-journal of immunology 26, 1695-1699.

An Z, Forrest G, Moore R, Cukan M, Haytko P, Huang L, Vitelli S, Zhao J Z, Lu P, Hua J, Gibson C R, Harvey B R, Montgomery D, Zaller D, Wang F, Strohl W. (2009). IgG2m4, an engineered antibody isotype with reduced Fc function. MAbs. 1, 572-579.

Arch, R. H., and Thompson, C. B. (1998). 4-1BB and Ox40 are members of a tumor necrosis factor (TNF)-nerve growth factor receptor subfamily that bind TNF receptor-associated factors and activate nuclear factor kappaB. Molecular and cellular biology 18, 558-565.

Aspeslagh, S., Postel-Vinay, S., Rusakiewicz, S., Soria, J. C., Zitvogel, L., and Marabelle, A. (2016). Rationale for anti-OX40 cancer immunotherapy. Eur J Cancer 52, 50-66.

Bulliard, Y., Jolicoeur, R., Zhang, J., Dranoff, G., Wilson, N. S., and Brogdon, J. L. (2014). OX40 engagement depletes intratumoral Tregs via activating FcgammaRs, leading to antitumor efficacy. Immunology and cell biology 92, 475-480.

Calderhead, D. M., Buhlmann, J. E., van den Eertwegh, A. J., Claassen, E., Noelle, R. J., and Fell, H. P. (1993). Cloning of mouse Ox40: a T cell activation marker that may mediate T-B cell interactions. J Immunol 151, 5261-5271.

Carboni, S., Aboul-Enein, F., Waltzinger, C., Killeen, N., Lassmann, H., and Pena-Rossi, C. (2003). CD134 plays a crucial role in the pathogenesis of EAE and is upregulated in the CNS of patients with multiple sclerosis. Journal of neuroimmunology 145, 1-11.

Compaan, D. M., and Hymowitz, S. G. (2006). The crystal structure of the costimulatory OX40-OX40L complex. Structure 14, 1321-1330.

Croft, M. (2010). Control of immunity by the TNFR-related molecule OX40 (CD134). Annual review of immunology 28, 57-78.

Croft, M., So, T., Duan, W., and Soroosh, P. (2009). The significance of OX40 and OX40L to T-cell biology and immune disease. Immunological reviews 229, 173-191.

Curti, B. D., Kovacsovics-Bankowski, M., Morris, N., Walker, E., Chisholm, L., Floyd, K., Walker, J., Gonzalez, I., Meeuwsen, T., Fox, B. A., et al. (2013). OX40 is a potent immune-stimulating target in late-stage cancer patients. Cancer research 73, 7189-7198.

Durkop, H., Latza, U., Himmelreich, P., and Stein, H. (1995). Expression of the human OX40 (hOX40) antigen in normal and neoplastic tissues. British journal of haematology 91, 927-931.

Gough, M. J., and Weinberg, A. D. (2009). OX40 (CD134) and OX40L. Advances in experimental medicine and biology 647, 94-107.

Gramaglia, I., Weinberg, A. D., Lemon, M., and Croft, M. (1998). Ox-40 ligand: a potent costimulatory molecule for sustaining primary CD4 T cell responses. J Immunol 161, 6510-6517.

Guo, Z., Cheng, D., Xia, Z., Luan, M., Wu, L., Wang, G., and Zhang, S. (2013). Combined TIM-3 blockade and CD137 activation affords the long-term protection in a murine model of ovarian cancer. Journal of translational medicine 11, 215.

Hori, S., Nomura, T., and Sakaguchi, S. (2003). Control of regulatory T cell development by the transcription factor Foxp3. Science 299, 1057-1061.

Huddleston, C. A., Weinberg, A. D., and Parker, D. C. (2006). OX40 (CD134) engagement drives differentiation of $CD4^+$ T cells to effector cells. European journal of immunology 36, 1093-1103.

Ito, T., Amakawa, R., Inaba, M., Hori, T., Ota, M., Nakamura, K., Takebayashi, M., Miyaji, M., Yoshimura, T., Inaba, K., and Fukuhara, S. (2004). Plasmacytoid dendritic cells regulate Th cell responses through OX40 ligand and type I IFNs. J Immunol 172, 4253-4259.

Ito, T., Wang, Y. H., Duramad, O., Hanabuchi, S., Perng, O. A., Gilliet, M., Qin, F. X., and Liu, Y. J. (2006). OX40 ligand shuts down IL-10-producing regulatory T cells. Proceedings of the National Academy of Sciences of the United States of America 103, 13138-13143.

Jacquemin, C., Schmitt, N., Contin-Bordes, C., Liu, Y., Narayanan, P., Seneschal, J., Maurouard, T., Dougall, D., Davizon, E. S., Dumortier, H., et al. (2015). OX40 Ligand Contributes to Human Lupus Pathogenesis by Promoting T Follicular Helper Response. Immunity 42, 1159-1170.

Kjaergaard, J., Tanaka, J., Kim, J. A., Rothchild, K., Weinberg, A., and Shu, S. (2000). Therapeutic efficacy of OX-40 receptor antibody depends on tumor immunogenicity and anatomic site of tumor growth. Cancer research 60, 5514-5521.

Ladanyi, A., Somlai, B., Gilde, K., Fejos, Z., Gaudi, I., and Timar, J. (2004). T-cell activation marker expression on tumor-infiltrating lymphocytes as prognostic factor in cutaneous malignant melanoma. Clinical cancer research: an official journal of the American Association for Cancer Research 10, 521-530.

Lai, C., August, S., Albibas, A., Behar, R., Cho, S. Y., Polak, M. E., Theaker, J., MacLeod, A. S., French, R. R., Glennie, M. J., et al. (2016). OX40+ Regulatory T Cells in Cutaneous Squamous Cell Carcinoma Suppress Effector T-Cell Responses and Associate with Metastatic Potential. Clinical cancer research: an official journal of the American Association for Cancer Research 22, 4236-4248.

Marabelle, A., Kohrt, H., and Levy, R. (2013a). Intratumoral anti-CTLA-4 therapy: enhancing efficacy while avoiding toxicity. Clinical cancer research: an official journal of the American Association for Cancer Research 19, 5261-5263.

Marabelle, A., Kohrt, H., Sagiv-Barfi, I., Ajami, B., Axtell, R. C., Zhou, G., Rajapaksa, R., Green, M. R., Torchia, J., Brody, J., et al. (2013b). Depleting tumor-specific Tregs at a single site eradicates disseminated tumors. The Journal of clinical investigation 123, 2447-2463.

Montler, R., Bell, R. B., Thalhofer, C., Leidner, R., Feng, Z., Fox, B. A., Cheng, A. C., Bui, T. G., Tucker, C., Hoen, H., and Weinberg, A. (2016). OX40, PD-1 and CTLA-4 are selectively expressed on tumor-infiltrating T cells in head and neck cancer. Clinical & translational immunology 5, e70.

Morris, N. P., Peters, C., Montler, R., Hu, H. M., Curti, B. D., Urba, W. J., and Weinberg, A. D. (2007). Development and characterization of recombinant human Fc: OX40L fusion protein linked via a coiled-coil trimerization domain. Molecular immunology 44, 3112-3121.

Ohshima, Y., Tanaka, Y., Tozawa, H., Takahashi, Y., Maliszewski, C., and Delespesse, G. (1997). Expression and function of OX40 ligand on human dendritic cells. J Immunol 159, 3838-3848.

Petty, J. K., He, K., Corless, C. L., Vetto, J. T., and Weinberg, A. D. (2002). Survival in human colorectal cancer correlates with expression of the T-cell costimulatory molecule OX-40 (CD134). American journal of surgery 183, 512-518.

Redmond, W. L., and Weinberg, A. D. (2007). Targeting OX40 and OX40L for the treatment of autoimmunity and cancer. Critical reviews in immunology 27, 415-436.

Rogers, P. R., Song, J., Gramaglia, I., Killeen, N., and Croft, M. (2001). OX40 promotes Bcl-xL and Bcl-2 expression and is essential for long-term survival of CD4 T cells. Immunity 15, 445-455.

Ruby, C. E., and Weinberg, A. D. (2009). OX40-enhanced tumor rejection and effector T cell differentiation decreases with age. J Immunol 182, 1481-1489.

Sarff, M., Edwards, D., Dhungel, B., Wegmann, K. W., Corless, C., Weinberg, A. D., and Vetto, J. T. (2008). OX40 (CD134) expression in sentinel lymph nodes correlates with prognostic features of primary melanomas. American journal of surgery 195, 621-625; discussion 625.

Sato, T., Ishii, N., Murata, K., Kikuchi, K., Nakagawa, S., Ndhlovu, L. C., and Sugamura, K. (2002). Consequences of OX40-OX40 ligand interactions in langerhans cell function: enhanced contact hypersensitivity responses in OX40L-transgenic mice. European journal of immunology 32, 3326-3335.

Smyth, M. J., Ngiow, S. F., and Teng, M. W. (2014). Targeting regulatory T cells in tumor immunotherapy. Immunology and cell biology 92, 473-474.

Song, A., Tang, X., Harms, K. M., and Croft, M. (2005a). OX40 and Bcl-xL promote the persistence of CD8 T cells to recall tumor-associated antigen. J Immunol 175, 3534-3541.

Song, J., So, T., Cheng, M., Tang, X., and Croft, M. (2005b). Sustained survivin expression from OX40 costimulatory signals drives T cell clonal expansion. Immunity 22, 621-631.

Song, J., So, T., and Croft, M. (2008). Activation of NF-kappaB1 by OX40 contributes to antigen-driven T cell expansion and survival. J Immunol 180, 7240-7248.

Soroosh, P., Ine, S., Sugamura, K., and Ishii, N. (2007). Differential requirements for OX40 signals on generation of effector and central memory CD4+ T cells. J Immunol 179, 5014-5023.

St Rose, M. C., Taylor, R. A., Bandyopadhyay, S., Qui, H. Z., Hagymasi, A. T., Vella, A. T., and Adler, A. J. (2013). CD134/CD137 dual costimulation-elicited IFN-gamma maximizes effector T-cell function but limits Treg expansion. Immunology and cell biology 91, 173-183.

Stuber, E., Neurath, M., Calderhead, D., Fell, H. P., and Strober, W. (1995). Cross-linking of OX40 ligand, a member of the TNF/NGF cytokine family, induces proliferation and differentiation in murine splenic B cells. Immunity 2, 507-521.

Szypowska, A., Stelmaszczyk-Emmel, A., Demkow, U., and Luczynski, W. (2014). High expression of OX40 (CD134) and 4-1BB (CD137) molecules on CD4(+)CD25(high) cells in children with type 1 diabetes. Advances in medical sciences 59, 39-43.

Timperi, E., Pacella, I., Schinzari, V., Focaccetti, C., Sacco, L., Farelli, F., Caronna, R., Del Bene, G., Longo, F., Ciardi, A., et al. (2016). Regulatory T cells with multiple suppressive and potentially pro-tumor activities accumulate in human colorectal cancer. Oncoimmunology 5, e1175800.

Tourkova, I. L., Yurkovetsky, Z. R., Shurin, M. R., and Shurin, G. V. (2001). Mechanisms of dendritic cell-induced T cell proliferation in the primary MLR assay. Immunology letters 78, 75-82.

Vetto, J. T., Lum, S., Morris, A., Sicotte, M., Davis, J., Lemon, M., and Weinberg, A. (1997). Presence of the T-cell activation marker OX-40 on tumor infiltrating lymphocytes and draining lymph node cells from patients with melanoma and head and neck cancers. American journal of surgery 174, 258-265.

Voo, K. S., Bover, L., Harline, M. L., Vien, L. T., Facchinetti, V., Arima, K., Kwak, L. W., and Liu, Y. J. (2013). Antibodies targeting human OX40 expand effector T cells and block inducible and natural regulatory T cell function. J Immunol 191, 3641-3650.

Weinberg, A. D., Rivera, M. M., Prell, R., Morris, A., Ramstad, T., Vetto, J. T., Urba, W. J., Alvord, G., Bunce, C., and Shields, J. (2000). Engagement of the OX-40 receptor in vivo enhances antitumor immunity. J Immunol 164, 2160-2169.

Weinberg, A. D., Wegmann, K. W., Funatake, C., and Whitham, R. H. (1999). Blocking OX-40/OX-40 ligand interaction in vitro and in vivo leads to decreased T cell function and amelioration of experimental allergic encephalomyelitis. J Immunol 162, 1818-1826.

Willoughby, J., Griffiths, J., Tews, I., and Cragg, M. S. (2017). OX40: Structure and function—What questions remain? Molecular immunology 83, 13-22.

Zander, R. A., Obeng-Adjei, N., Guthmiller, J. J., Kulu, D. I., Li, J., Ongoiba, A., Traore, B., Crompton, P. D., and Butler, N. S. (2015). PD-1 Co-inhibitory and OX40 Co-stimulatory Crosstalk Regulates Helper T Cell Differentiation and Anti-*Plasmodium* Humoral Immunity. Cell host & microbe 17, 628-641.

Zhang, T., Lemoi, B. A., and Sentman, C. L. (2005). Chimeric NK-receptor-bearing T cells mediate antitumor immunotherapy. Blood 106, 1544-1551.

The invention claimed is:

1. An antibody or antigen-binding fragment thereof, which specifically binds to human OX40 and comprises:
   (i) a heavy chain variable region that comprises: (a) a HCDR (Heavy Chain Complementarity Determining Region) 1 of SEQ ID NO: 3, (b) a HCDR2 of SEQ ID NO: 24, (c) and a HCDR3 of SEQ ID NO: 5 and a light chain variable region that comprises: (d) a LCDR (Light Chain Complementarity Determining Region) 1 of SEQ ID NO: 25, (e) a LCDR2 of SEQ ID NO: 19, and (f) a LCDR3 of SEQ ID NO: 8;
   (ii) a heavy chain variable region that comprises: (a) a HCDR1 of SEQ ID NO: 3, (b) a HCDR2 of SEQ ID NO: 18, and (c) a HCDR3 of SEQ ID NO: 5; and a light chain variable region that comprises: (d) a LCDR1 of SEQ ID NO: 6, (e) a LCDR2 of SEQ ID NO: 19, and (f) a LCDR3 of SEQ ID NO: 8;
   (iii) a heavy chain variable region that comprises: (a) a HCDR1 of SEQ ID NO: 3, (b) a HCDR2 of SEQ ID NO: 13, and (c) a HCDR3 of SEQ ID NO: 5; and a light chain variable region that comprises: (d) a LCDR1 of SEQ ID NO: 6, (e) a LCDR2 of SEQ ID NO: 7, and (f) a LCDR3 of SEQ ID NO: 8; or
   (iv) a heavy chain variable region that comprises: (a) a HCDR1 of SEQ ID NO: 3, (b) a HCDR2 of SEQ ID NO: 4, and (c) a HCDR3 of SEQ ID NO: 5; and a light chain variable region that comprises: (d) a LCDR1 of SEQ ID NO: 6, (e) a LCDR2 of SEQ ID NO: 7, and (f) a LCDR3 of SEQ ID NO: 8,
   wherein said human OX40 comprises SEQ ID NO: 2.

2. The antibody or antigen-binding fragment of claim 1, wherein:
   (i) when the heavy chain variable region (VH) comprises HCDRs comprising SEQ ID NOs: 3, 24, and 5 and the light chain variable region (VL) comprises LCDRs comprising SEQ ID NOs: 25, 19, and 8, the heavy chain variable region (VH) comprises an amino acid sequence at least 90, 91, 92, 93, 94, 95, 96, 97, 98 or 99% identical to SEQ ID NO:26, and the light chain variable region (VL) region comprises an amino acid sequence at least 90, 91, 92, 93, 94, 95, 96, 97, 98 or 99% identical to SEQ ID NO: 28;
   (ii) when the heavy chain variable region (VH) comprises HCDRs comprising SEQ ID NOs: 3, 18, and 5 and the light chain variable region (VL) comprises LCDRs comprising SEQ ID NOs: 6, 19, and 8, the heavy chain variable region (VH) comprises an amino acid sequence at least 90, 91, 92, 93, 94, 95, 96, 97, 98 or 99% identical to SEQ ID NO: 20, and the light chain variable region (VL) comprises an amino acid sequence at least 90, 91, 92, 93, 94, 95, 96, 97, 98 or 99% identical to SEQ ID NO: 22;

(iii) when the heavy chain variable region (VH) comprises HCDRs comprising SEQ ID NOs: 3, 13, and 5 and the light chain variable region (VL) comprises LCDRs comprising SEQ ID NOs: 6, 7, and 8, the heavy chain variable region (VH) comprises an amino acid sequence at least 90, 91, 92, 93, 94, 95, 96, 97, 98 or 99% identical to SEQ ID NO: 14, and the light chain variable region (VL) comprises an amino acid sequence at least 90, 91, 92, 93, 94, 95, 96, 97, 98 or 99% identical to SEQ ID NO: 16; or (iv) when the heavy chain variable region (VH) comprises HCDRs comprising SEQ ID NOs: 3, 4, and 5 and the light chain variable region (VL) comprises LCDRs comprising SEQ ID NOs: 6, 7, and 8, the heavy chain variable region (VH) comprises an amino acid sequence at least 90, 91, 92, 93, 94, 95, 96, 97, 98 or 99% identical to SEQ ID NO: 9, and the light chain variable region (VL) comprises an amino acid sequence at least 90, 91, 92, 93, 94, 95, 96, 97, 98 or 99% identical to SEQ ID NO: 11.

3. The antibody or antigen-binding fragment of claim 1, that comprises:

(i) a heavy chain variable region (VH) that comprises SEQ ID NO: 26, and a light chain variable region (VL) that comprises SEQ ID NO: 28;

(ii) a heavy chain variable region (VH) that comprises SEQ ID NO: 20, and a light chain variable region (VL) that comprises SEQ ID NO: 22;

(iii) a heavy chain variable region (VH) that comprises SEQ ID NO: 14, and a light chain variable region (VL) that comprises SEQ ID NO: 16; or (iv) a heavy chain variable region (VH) that comprises SEQ ID NO: 9, and a light chain variable region (VL) that comprises SEQ ID NO: 11.

4. The antibody or antigen-binding fragment of claim 1, which is a monoclonal antibody, a chimeric antibody, a humanized antibody, a single chain antibody (scFv), a Fab fragment, a Fab' fragment, or a F(ab')2 fragment.

5. The antibody or antigen-binding fragment of claim 4, wherein the antibody or antigen-binding fragment thereof comprises an Fc domain and has antibody dependent cellular cytotoxicity (ADCC) or complement dependent cytotoxicity (CDC).

6. The antibody or antigen-binding fragment of claim 1, wherein the antibody or antigen-binding fragment thereof comprises an Fc domain and has reduced glycosylation or no glycosylation or is hypofucosylated.

7. The antibody or antigen-binding fragment of claim 1, wherein the antibody or antigen-binding fragment thereof comprises an Fc domain and increased bisecting GlcNac structures.

8. The antibody or antigen-binding fragment of claim 1, wherein the antibody or antigen-binding fragment thereof comprises an Fc domain and the Fc domain is of an IgG1.

9. The antibody or antigen-binding fragment of claim 1, wherein the antibody or antigen-binding fragment thereof comprises an Fc domain and the Fc domain is of a human IgG4.

10. The antibody or antigen-binding fragment of claim 9, wherein the human IgG4 has an S228P substitution (according to EU numbering system).

11. The antibody or antigen-binding fragment of claim 10, wherein the human IgG4 has S228P and R409K substitutions (according to EU numbering system).

12. A pharmaceutical composition comprising the antibody or antigen-binding fragment thereof of claim 1, further comprising a pharmaceutically acceptable carrier.

13. A method of treating cancer comprising administering to a human patient who has cancer an effective amount of the antibody or antigen-binding fragment of claim 1.

14. The method of claim 13, wherein the cancer is selected from the group consisting of breast cancer, head and neck cancer, gastric cancer, kidney cancer, liver cancer, small cell lung cancer, non-small cell lung cancer, ovarian cancer, skin cancer, mesothelioma, lymphoma, leukemia, myeloma, and sarcoma.

15. The method of claim 14, wherein the antibody or antigen-binding fragment is administered in combination with another therapeutic agent.

16. The method of claim 15, wherein the therapeutic agent is paclitaxel, docetaxel, topotecan, irinotecan, doxorubicin, lenalidomide or 5-azacytidine.

17. The method of claim 15, wherein the therapeutic agent is paclitaxel, lenalidomide or 5-azacytidine.

* * * * *

UNITED STATES PATENT AND TRADEMARK OFFICE
CERTIFICATE OF CORRECTION

| | | |
|---|---|---|
| PATENT NO. | : 12,103,974 B2 | Page 1 of 1 |
| APPLICATION NO. | : 17/055267 | |
| DATED | : October 1, 2024 | |
| INVENTOR(S) | : Ye Liu et al. | |

It is certified that error appears in the above-identified patent and that said Letters Patent is hereby corrected as shown below:

In the Claims

Claim 1, Column 61, Line 48, delete "(c) and" and replace with -- and (c) --

Claim 9, Column 64, Line 15, delete "an Fe domain and the Fe domain" and replace with -- an Fc domain and the Fc domain --

Claim 16, Column 64, Line 40, delete "paclitaxel, docetaxel, topotecan, irinotecan, doxorubicin," and replace with -- paclitaxel, docetaxel, carboplatin, topotecan, cisplatin, irinotecan, doxorubicin, --

Signed and Sealed this
Seventeenth Day of December, 2024

Derrick Brent
*Acting Director of the United States Patent and Trademark Office*